US010660676B2

(12) United States Patent
Lintula et al.

(10) Patent No.: US 10,660,676 B2
(45) Date of Patent: May 26, 2020

(54) IMPLANTS, DEVICES, INSTRUMENTS, SYSTEMS AND METHODS OF FORMING AND IMPLANTING

(71) Applicant: PARAGON 28, INC., Englewood, CO (US)

(72) Inventors: Eric Lintula, Parker, CO (US); Laura Zagrocki Brinker, Denver, CO (US); Jens Cole, Golden, CO (US); Albert DaCosta, Lone Tree, CO (US)

(73) Assignee: PARAGON 28, INC., Englewood, CO (US)

(*) Notice: Subject to any disclaimer, the term of this patent is extended or adjusted under 35 U.S.C. 154(b) by 96 days.

(21) Appl. No.: 15/900,528

(22) Filed: Feb. 20, 2018

(65) Prior Publication Data
US 2018/0243018 A1  Aug. 30, 2018

Related U.S. Application Data

(63) Continuation of application No. PCT/US2018/018821, filed on Feb. 20, 2018.
(Continued)

(51) Int. Cl.
| | |
|---|---|
| *A61B 17/72* | (2006.01) |
| *A61F 2/42* | (2006.01) |
| *A61B 17/16* | (2006.01) |
| *A61B 17/88* | (2006.01) |
| *A61B 17/15* | (2006.01) |

(Continued)

(52) U.S. Cl.
CPC .......... *A61B 17/7291* (2013.01); *A61B 17/15* (2013.01); *A61B 17/1615* (2013.01); *A61B 17/1637* (2013.01); *A61B 17/1682* (2013.01); *A61B 17/8872* (2013.01); *A61B 17/8897* (2013.01); *A61F 2/4225* (2013.01); *A61B 17/1635* (2013.01); *A61B 17/17* (2013.01); *A61B 2017/00933* (2013.01); *A61F 2002/4228* (2013.01)

(58) Field of Classification Search
CPC ..... A61B 17/72; A61B 17/7291; A61B 17/15; A61B 17/1615; A61B 17/1617; A61B 17/1637; A61B 17/68
See application file for complete search history.

(56) References Cited

U.S. PATENT DOCUMENTS

| | | | |
|---|---|---|---|
| 5,593,409 A | 1/1997 | Michelson | |
| 6,008,431 A | 12/1999 | Caldarise et al. | |

(Continued)

FOREIGN PATENT DOCUMENTS

WO   2011110784   9/2011

OTHER PUBLICATIONS

International Search Report and Written Opinion of the International Searching Authority for PCT/US2018/022079, dated May 25, 2018, 11 pages.

(Continued)

*Primary Examiner* — Julianna N Harvey
*Assistant Examiner* — Christina Negrellirodriguez
(74) *Attorney, Agent, or Firm* — Heslin Rothenberg Farley & Mesiti P.C.

(57) ABSTRACT

Implants, devices, instruments, systems and methods for correcting bone deformities in the lower extremity are disclosed. Specifically, implants, devices, instruments, systems and methods used for hammertoe procedures are disclosed.

20 Claims, 64 Drawing Sheets

Related U.S. Application Data

(60) Provisional application No. 62/461,201, filed on Feb. 20, 2017.

(51) Int. Cl.
*A61B 17/17* (2006.01)
*A61B 17/00* (2006.01)

(56) References Cited

U.S. PATENT DOCUMENTS

| | | | |
|---|---|---|---|
| 6,123,705 | A | 9/2000 | Michelson |
| 6,726,722 | B2 | 4/2004 | Walkenhorst et al. |
| 7,041,106 | B1 | 5/2006 | Carver et al. |
| 8,414,583 | B2 | 4/2013 | Prandi et al. |
| 8,529,611 | B2 | 9/2013 | Champagne et al. |
| 8,597,337 | B2 | 12/2013 | Champagne |
| 8,672,986 | B2 | 3/2014 | Klaue et al. |
| 8,715,325 | B2 | 5/2014 | Weiner et al. |
| 8,715,326 | B2 | 5/2014 | Champagne et al. |
| 8,834,572 | B2 | 9/2014 | Averous et al. |
| 8,864,804 | B2 | 10/2014 | Champagne et al. |
| 9,044,287 | B2 | 6/2015 | Reed et al. |
| 9,072,562 | B2 | 7/2015 | Weiner et al. |
| 9,072,564 | B2 | 7/2015 | Reed et al. |
| 9,168,074 | B2 | 10/2015 | Prandi et al. |
| 10,058,431 | B2 | 8/2018 | Tyber et al. |
| 2003/0083689 | A1* | 5/2003 | Simonson ............ A61B 17/025 606/191 |
| 2004/0106997 | A1* | 6/2004 | Lieberson ........... A61B 17/1757 623/17.16 |
| 2007/0093841 | A1 | 4/2007 | Hoogland |
| 2007/0270711 | A1 | 11/2007 | Gil et al. |
| 2010/0266979 | A1 | 10/2010 | Karmon |
| 2011/0054545 | A1 | 3/2011 | Champagne et al. |
| 2012/0065692 | A1 | 3/2012 | Champagne et al. |
| 2012/0221049 | A1 | 8/2012 | Blain |
| 2012/0323243 | A1 | 12/2012 | Moon et al. |
| 2013/0030475 | A1 | 1/2013 | Weiner et al. |
| 2013/0060295 | A1 | 3/2013 | Reed et al. |
| 2013/0066383 | A1 | 3/2013 | Anderson et al. |
| 2013/0123862 | A1 | 5/2013 | Anderson et al. |
| 2013/0131822 | A1 | 5/2013 | Lewis et al. |
| 2013/0150965 | A1 | 6/2013 | Taylor et al. |
| 2013/0165982 | A1 | 6/2013 | Ek et al. |
| 2013/0190831 | A1 | 7/2013 | Ek et al. |
| 2013/0317559 | A1 | 11/2013 | Leavitt et al. |
| 2013/0325077 | A1 | 12/2013 | Champagne et al. |
| 2013/0338785 | A1 | 12/2013 | Wong |
| 2014/0052196 | A1 | 2/2014 | McGinley et al. |
| 2014/0107712 | A1 | 4/2014 | Fallin et al. |
| 2014/0142715 | A1 | 5/2014 | McCormick |
| 2014/0188239 | A1 | 7/2014 | Cummings |
| 2014/0222091 | A1 | 8/2014 | Champagne et al. |
| 2014/0276827 | A1 | 9/2014 | Roman et al. |
| 2014/0277183 | A1 | 9/2014 | Stalcup et al. |
| 2014/0277186 | A1 | 9/2014 | Granberry et al. |
| 2014/0277191 | A1 | 9/2014 | Evans et al. |
| 2014/0277554 | A1 | 9/2014 | Roman et al. |
| 2014/0309747 | A1 | 10/2014 | Taylor et al. |
| 2015/0032108 | A1 | 1/2015 | Roman |
| 2015/0073413 | A1 | 3/2015 | Palmer et al. |
| 2015/0094778 | A1 | 4/2015 | McCormick et al. |
| 2015/0112341 | A1 | 4/2015 | Penzimer et al. |
| 2015/0142066 | A1* | 5/2015 | Shemwell ............ A61B 17/7291 606/301 |
| 2015/0150607 | A1 | 6/2015 | Chen et al. |
| 2015/0164563 | A1 | 6/2015 | Lewis et al. |
| 2015/0190147 | A1 | 7/2015 | Ferragamo et al. |
| 2015/0305789 | A1 | 10/2015 | Weiner et al. |
| 2015/0374503 | A1 | 12/2015 | Lovick et al. |
| 2016/0015437 | A1 | 1/2016 | Elleby et al. |
| 2016/0030095 | A1 | 2/2016 | Roman et al. |
| 2016/0045324 | A1 | 2/2016 | Austin et al. |
| 2016/0287407 | A1 | 10/2016 | Patrick et al. |
| 2017/0000618 | A1 | 1/2017 | Tyber et al. |
| 2018/0021145 | A1 | 1/2018 | Seavey et al. |
| 2018/0256219 | A1 | 9/2018 | Lintula et al. |

OTHER PUBLICATIONS

International Search Report and Written Opinion of the International Searching Authority for PCT/US2018/018821, dated Jun. 22, 2018, 18 pages.

* cited by examiner

IMPLANTS, DEVICES, INSTRUMENTS, SYSTEMS AND METHODS OF FORMING AND IMPLANTING

CROSS-REFERENCE TO RELATED APPLICATION

This application is a continuation of PCT Application No. PCT/US2018/018821 filed on Feb. 20, 2018, which claims priority benefit under 35 U.S.C. § 119(e) of U.S. provisional application No. 62/461,201 filed Feb. 20, 2017, which is incorporated herein by reference in its entirety.

FIELD OF THE INVENTION

The present invention relates generally to general surgery, podiatric, and orthopaedic implants used for correcting bone deformities. More specifically, but not exclusively, the present invention relates to implants, devices, instruments, systems and methods for correcting bone deformities.

BACKGROUND OF THE INVENTION

Many currently available implants for correcting a hammer toe deformity use non-allograft or autograft materials, for example, many implants include a threaded pin, ribbed member, flexible silicone joint, or coated peg. The currently available implants may experience problems with bone integration and may be difficult to perform revision surgery on without compromising the host bone. Thus, new methods, implants and instruments are needed to provide implants made of allograft or autograft bone for easier revision surgeries.

SUMMARY OF THE INVENTION

Aspects of the present invention provide implants, devices and methods for correcting bone deformities in the foot.

In one aspect, provided herein is an implant insertion and removal system. The implant insertion system includes, at least one trocar tip guide wire, at least one trephine including an opening for receiving the at least one trocar tip guide wire, at least one reamer including an opening for receiving the at least one trocar tip guide wire, and at least one drill bit including an opening for receiving the at least one trocar tip guide wire.

In another aspect, provided herein is a method of forming an implant. The method includes, obtaining a piece of bone graft material and forming a first bone member with a first end and a second end. The method also includes reaming the second end of the first bone member to form a second bone member with a first body portion and a second body portion. In addition, the method includes forming a plurality of first grooves in a dorsal surface and a plantar surface of the second bone member. The method further includes forming a plurality of second grooves in a medial surface and a lateral surface of the second body portion of the second body member and forming a plurality of third grooves in a medial surface and a lateral surface of the first body portion of the second bone member.

In yet another aspect, provided herein is a surgical method. The surgical method includes, exposing a patient's joint and inserting a first k-wire into a base of the middle phalanx proximally. The method also includes retrograding the first k-wire from a tip of a toe, across a distal phalanx and a middle phalanx and inserting the first k-wire into a proximal phalanx. The method further includes pulling the first k-wire to position a tip of the first k-wire in the joint and inserting a second k-wire into the proximal phalanx. In addition, the method includes driving a drill across the second k-wire and into the proximal phalanx and removing the second k-wire from the patient's joint. The method also includes driving the drill over the first k-wire and into the middle phalanx and inserting an implant into the proximal phalanx and the middle phalanx. Finally, the method includes completing the procedure.

In another aspect, provided herein is an alternative surgical method. The surgical method includes, exposing a patient's joint, coupling a guide wire to a reamer, and inserting the coupled guide wire and reamer into a middle phalanx and proximal phalanx. The method also includes removing the coupled guide wire and reamer after cartilage resection is complete and coupling the guide wire to a drill. The method further includes inserting the coupled guide wire and drill into a proximal phalanx and removing the coupled guide wire and drill from the proximal phalanx. In addition, the method includes inserting the coupled guide wire and drill into the middle phalanx and removing the coupled guide wire and drill from the middle phalanx. Finally, the method includes inserting an implant into the proximal phalanx and the middle phalanx and completing the procedure.

In still another aspect, provided herein is a cutting guide. The cutting guide includes a base portion and at least one plate member with at least one implant opening, wherein the at least one plate member engages a top surface of the base portion.

In a further aspect, provided herein is an implant. The implant includes a first body portion and a second body portion. The first body portion extends from a first end toward the second body portion, the second body portion extends from a second end toward the first body portion, and the first body portion engages the second body portion at a coupling portion.

In another aspect, provided herein is another implant. The implant including a body portion with a first end and a second end, a first protrusion extending circumferentially away from the body portion, the first protrusion positioned between the first end and a central member of the body portion, and a second protrusion extending circumferentially away from the body portion, the second protrusion positioned between the central member and the second end of the body portion.

In yet another aspect, provided herein is an insertion instrument. The insertion instrument includes an opening for receiving a portion of an implant. The insertion instrument also includes a handle portion and a coupling member coupled to and extending away from an end of the handle portion.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Figure 1:
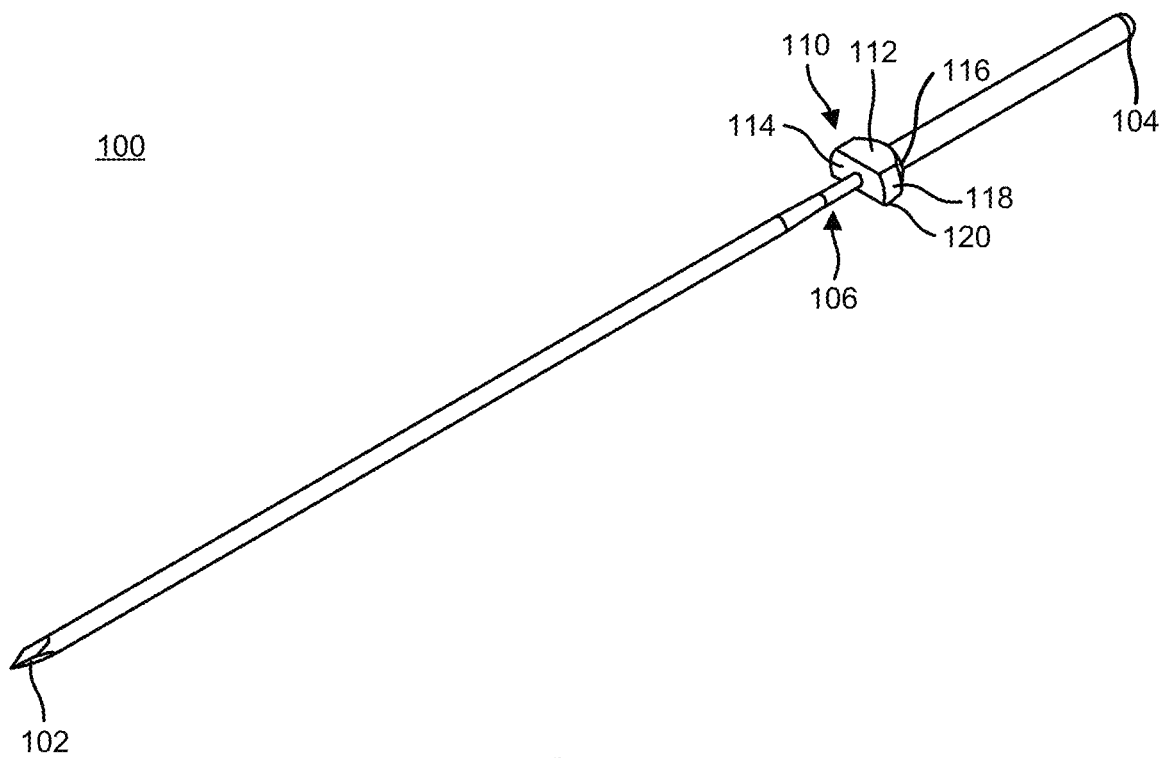
FIG. 1 is a top perspective view of one embodiment of a guide wire, in accordance with an aspect of the present invention.

Generally stated, disclosed herein are implants, devices, instruments, and systems for correcting bone deformities. Further, methods for forming implants and surgical methods for correcting bone deformities using the implants, devices, instruments and systems are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers to the bottom of the foot.

Similarly, positions or directions may be used herein with reference to anatomical structures or surfaces. For example, as the current implants, devices, instrumentation and methods are described herein with reference to use with the bones of the foot, ankle and lower leg may be used to describe the surfaces, positions, directions or orientations of the implants, devices, instrumentation and methods. Further, the implants, devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation and methods, and the aspects, components, features and the like thereof, described herein with respect to the right foot may be mirrored so that they likewise function with the left foot.

Further, the implants, devices, instrumentation and methods, and the aspects, components, features and the like thereof, disclosed herein are described with respect to the foot for brevity purposes, but it should be understood that the implants, devices, instrumentation and methods may be used with other bones of the body having similar structures.

Referring to the drawings, wherein like reference numerals are used to indicate like or analogous components throughout the several views, and with particular reference to FIGS. 1-30, there is illustrated one embodiment of an implant insertion and removal system including a first guide wire or trocar tip guide wire 100, a second guide wire or trocar tip guide wire 150, an instrument connector end 200, a hole saw or trephine 250, a reamer 300, a first drill bit 350, a second drill bit 400, and at least one implant 680, as shown in FIGS. 59-64. As shown in FIGS. 1-4, the first trocar tip guide wire, guide wire, or k-wire 100 may include a first end 102 and a second end 104. The first end 102 may be a sharp cutting end. The first guide wire 100 may also include a coupling member 110 positioned between the first end 102 and the second end 104. The coupling member 110 may be positioned near the second end 104. The first guide wire 100 may further include a tapered region 106 extending out from the coupling member 110 toward the first end 102. The tapered region 106 is sized to enable the wire 100 to flex and pop into and out of the trephine 250, reamer 300, and drill bits 350, 400.

Figure 2:
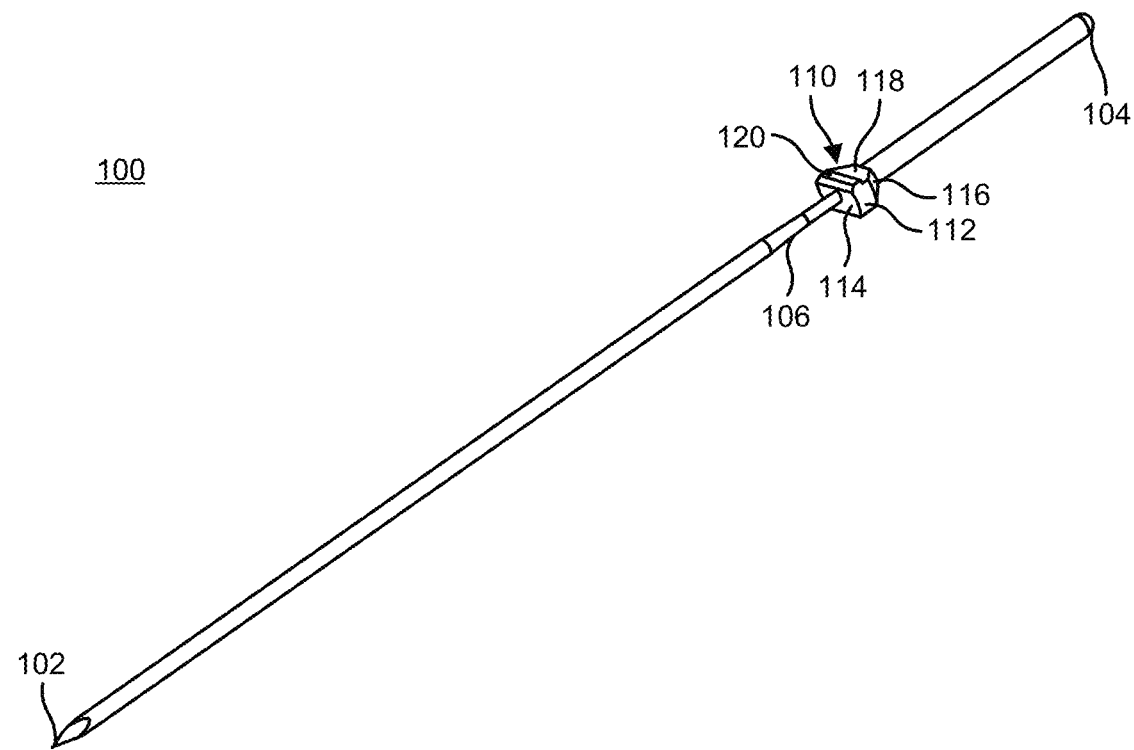
FIG. 2 is a bottom perspective view of the guide wire of FIG. 1, in accordance with an aspect of the present invention.
Figure 3:
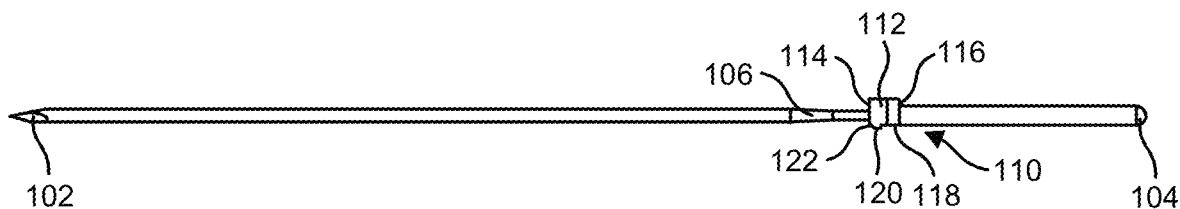
FIG. 3 is a first side view of the guide wire of FIG. 1, in accordance with an aspect of the present invention.
Figure 4:
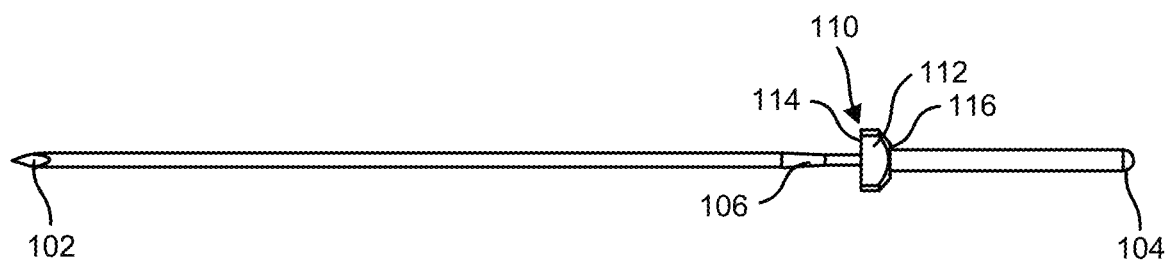
FIG. 4 is a second side view of the guide wire of FIG. 1, in accordance with an aspect of the present invention.
Figure 5:
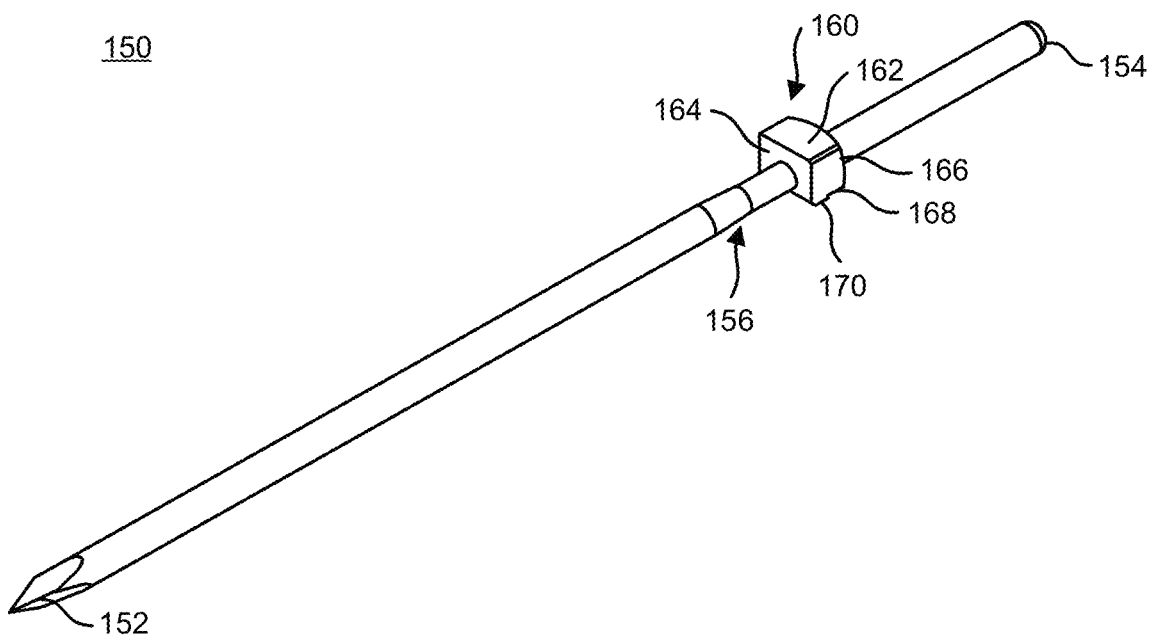
FIG. 5 is a top perspective view of another embodiment guide wire, in accordance with an aspect of the present invention.

As shown in FIGS. 2 and 3, the coupling member 110 may include a body 112 with a first end 114 and a second end 116. The first end 114 may engage the tapered region 106 of the first guide wire 100. The second end 116 may be coupled to the second end of the first guide wire 100. The second end 116 may include angled or tapered edges as the coupling member 110 extends from the body 112 to the point of attachment with the guide wire 100. The coupling member 110 may further include an engagement surface 118 and an engagement member, ridge, protrusion, snap member or lip 120 on a side of the coupling member 110. The ridge 120 may extend away from the engagement surface 118. The ridge 120 may be configured or sized and shaped to receive a correspondingly shaped engagement member, as described in greater detail below. The coupling member 110 may also include an angled or chamfered edge 122 on the first end 114 of the coupling member 110, as shown in FIG. 3.

As shown in FIGS. 5-8, the second trocar tip guide wire 150 may include a first end 152 and a second end 154. The first end 152 may be a sharp cutting end. The second guide wire 150 may also include a coupling member 160 positioned between the first end 152 and the second end 154. The coupling member 160 may be positioned near the second end 154. The second guide wire 150 may further include a tapered region 156 extending out from the coupling member 160 toward the first end 152.

Figure 6:
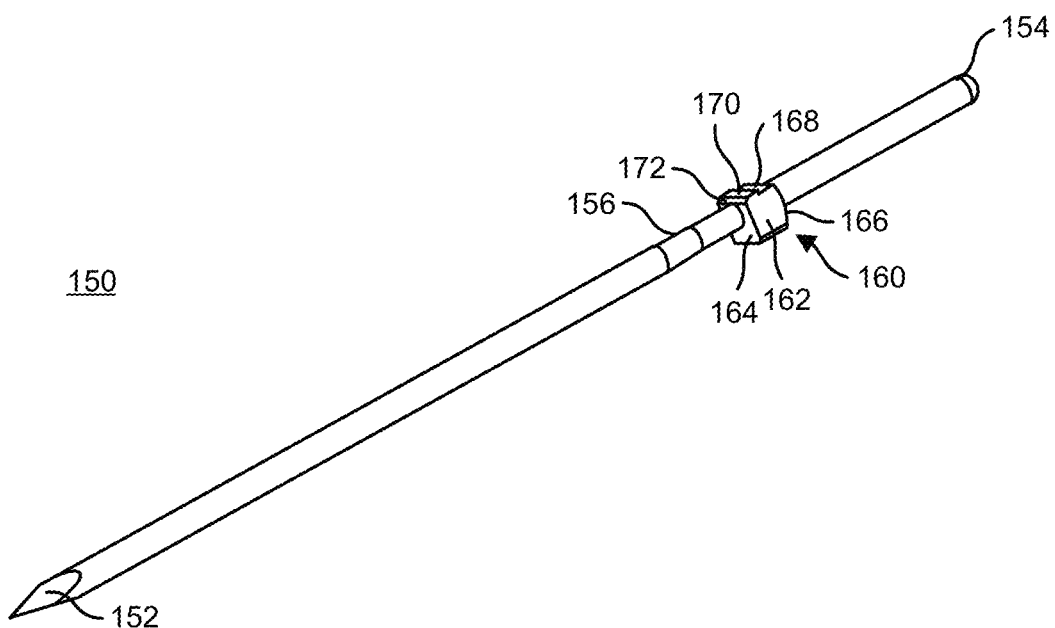
FIG. 6 is a side perspective view of the guide wire of FIG. 5, in accordance with an aspect of the present invention.
Figure 7:
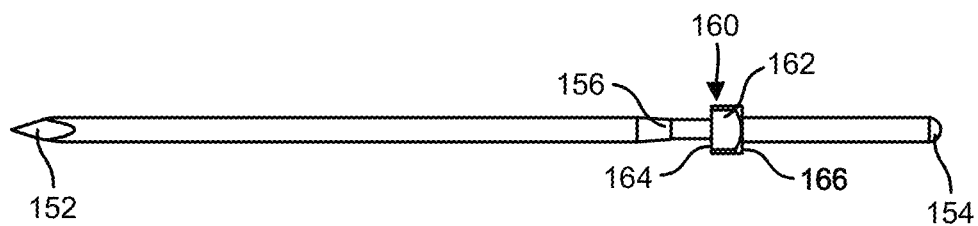
FIG. 7 is a first side view of the guide wire of FIG. 5, in accordance with an aspect of the present invention.
Figure 8:
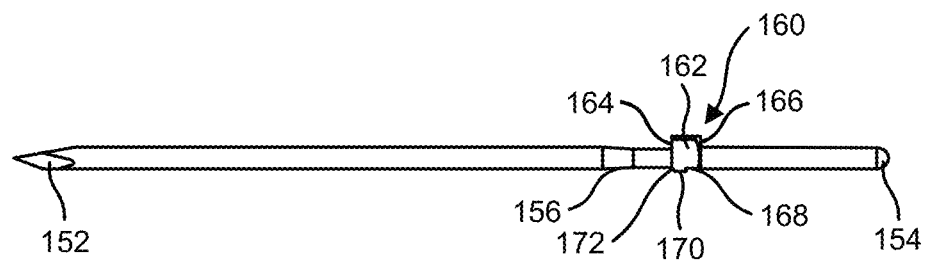
FIG. 8 is a second side view of the guide wire of FIG. 5, in accordance with an aspect of the present invention.

As shown in FIGS. 6 and 8, the coupling member 160 may include a body 162 with a first end 164 and a second end 166. The first end 164 may engage the tapered region 156 of the second guide wire 150. The second end 166 of the coupling member 160 may be coupled to the second end of the second guide wire 150. The coupling member 160 may further include an engagement surface 168 and an engagement member, ridge, protrusion, snap member or lip 170 on a side of the coupling member 160. The ridge 170 may extend away from the engagement surface 168. The ridge 170 may be configured or sized and shaped to receive a correspondingly shaped engagement member of, for example, an instrument connector end 200, as described in greater detail below. The coupling member 160 may also include an angled or chamfered edge 172 on the first end 164 of the coupling member 160, as shown in FIGS. 6 and 8. The second trocar tip guide wire 150 may have, for example, a larger diameter than the first trocar tip guide wire 100. In addition, the second guide wire 150 may have a coupling member 160 with a width, for example, smaller than the width of the coupling member 110 of the first guide wire 100.

Figure 9:
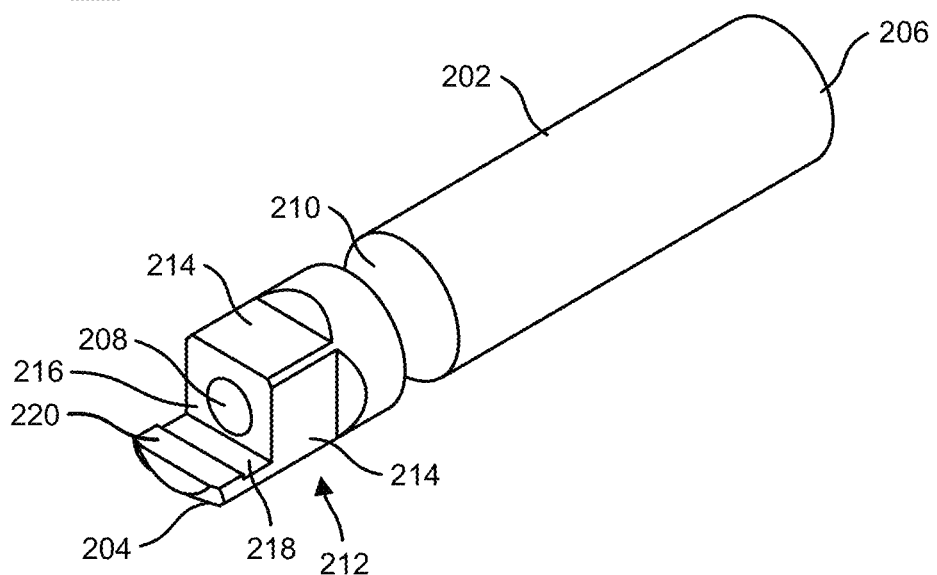
FIG. 9 is a first end perspective view of a connector end, in accordance with an aspect of the present invention.
Figure 10:
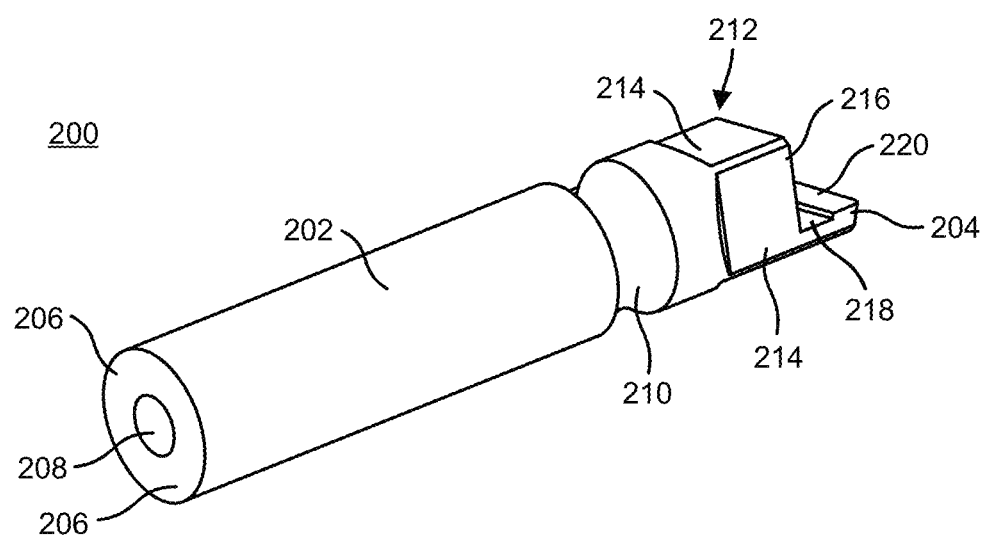
FIG. 10 is a second end perspective view of the connector end of FIG. 9, in accordance with an aspect of the present invention.
Figure 11:
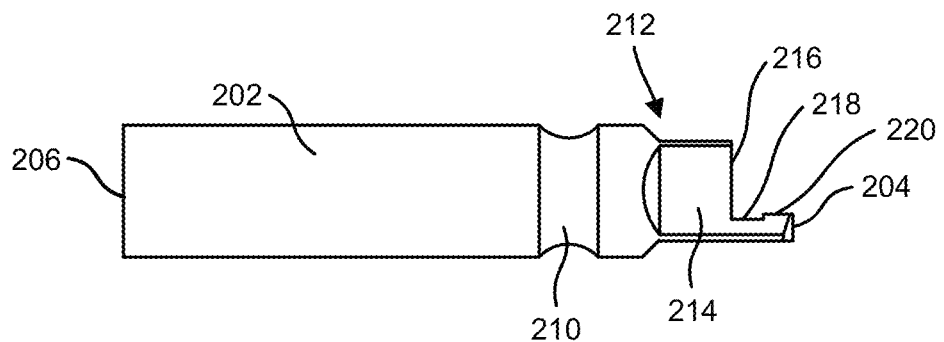
FIG. 11 is a side view of the connector end of FIG. 9, in accordance with an aspect of the present invention.
Figure 12:
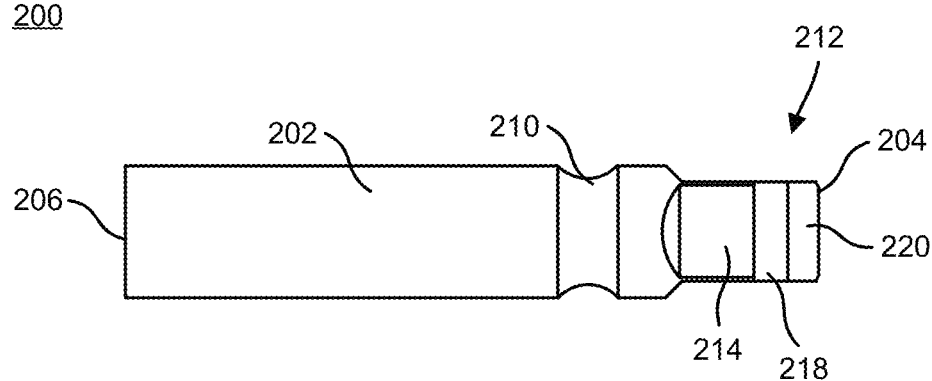
FIG. 12 is a top view of the connector end of FIG. 9, in accordance with an aspect of the present invention.
Figure 13:
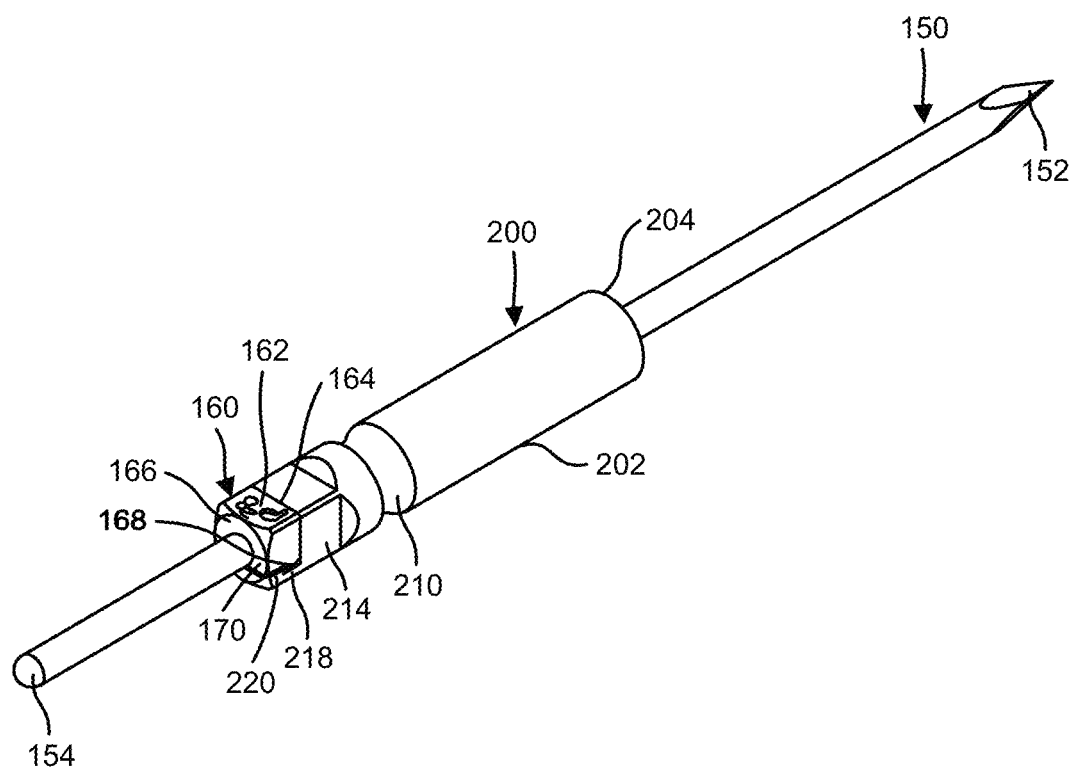
FIG. 13 is a perspective view of the assembled guide wire of FIG. 5 and the connector end of FIG. 9, in accordance with an aspect of the present invention.
Figure 14:
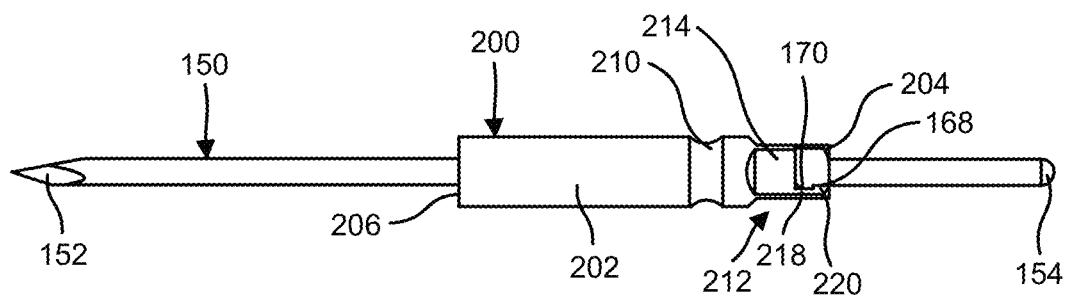
FIG. 14 is a side view of the assembled guide wire and connector end of FIG. 13, in accordance with an aspect of the present invention.

Referring now to FIGS. 9-14 an instrument connector end 200 is shown. The connector end 200 includes a body 202 with a first end 204 and a second end 206. The connector end 200 may also include a through hole 208 extending through the body 202 from the first end 204 to the second end 206. The through hole 208 may include a relief 222, as shown in FIG. 9. The body 202 may also include a groove 210 positioned circumferentially around the body 202 near the first end 204. The first end 204 may also include an engagement member 212. The engagement member 212 may include inset side surfaces 214. The inset side surfaces 214 may be, for example, positioned adjacent or in close proximity to the groove 210. The engagement member 212 may also include an end surface 216 configured or sized and shaped to receive a first end 164 of a guide wire 150. The engagement member 212 may also include an engagement surface 218 positioned adjacent and perpendicular to the end surface 216. The engagement member 212 may further include a ridge, protrusion, snap member or lip 220 extending from the engagement surface 218. The ridge 220 may be configured or sized and shaped for receiving the ridge 170 of the guide wire 150, to couple the connector end 200 to a guide wire 150, as shown in FIGS. 13 and 14. In one embodiment, the ridge 220 of the connector end 200 and the ridge 170 of the guide wire 150 may be, for example, undercut to enable the connector end 200 to snap into engagement with the guide wire 150. The coupling member 160 may bend at the tapered region 156 to engage with and disengage from the engagement member 212 and the relief 222 in the through hole 208 may provide the space to allow for the second trocar 150 to bend. The second end 206 may extend to include, for example, a trephine, drill, and/or reamer (not shown) extending away from the second end 206 of the connector end 200.

Figure 15:
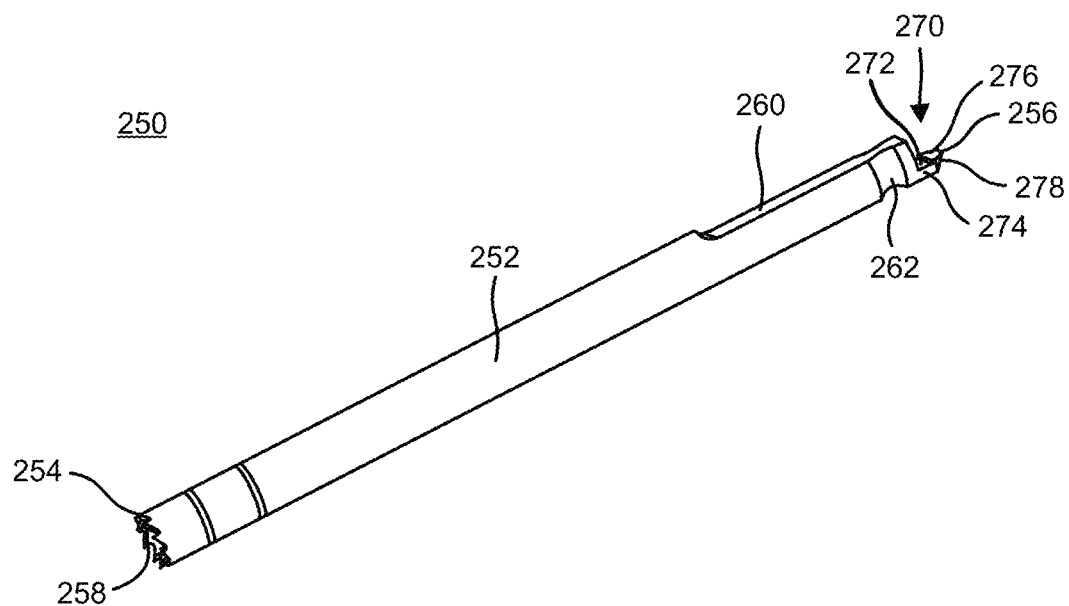
FIG. 15 is a side perspective view of a cannulated trephine, in accordance with an aspect of the present invention.
Figure 16:
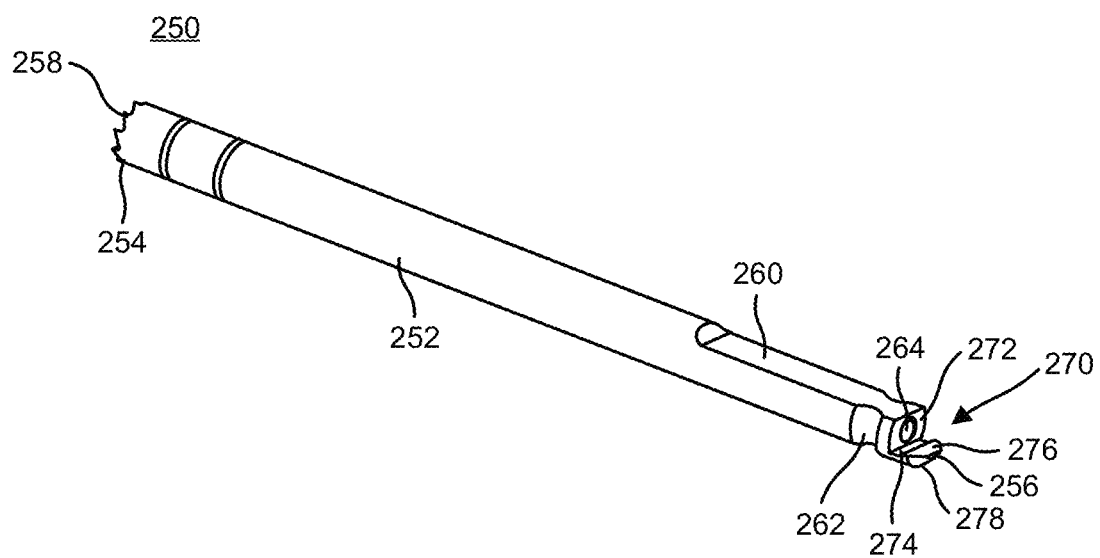
FIG. 16 is an end perspective view of the cannulated trephine of FIG. 15, in accordance with an aspect of the present invention.
Figure 17:
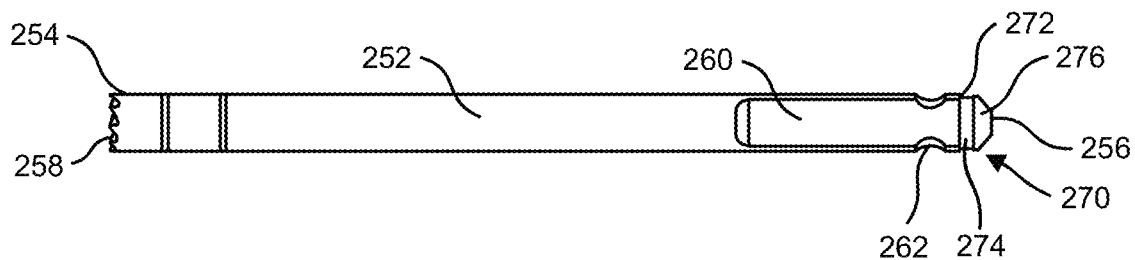
FIG. 17 is a top view of the cannulated trephine of FIG. 15, in accordance with an aspect of the present invention.
Figure 18:
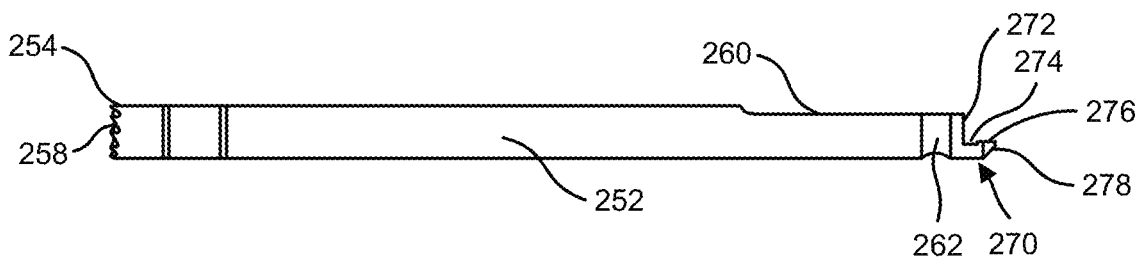
FIG. 18 is a side view of the cannulated trephine FIG. 15, in accordance with an aspect of the present invention.
Figure 19:
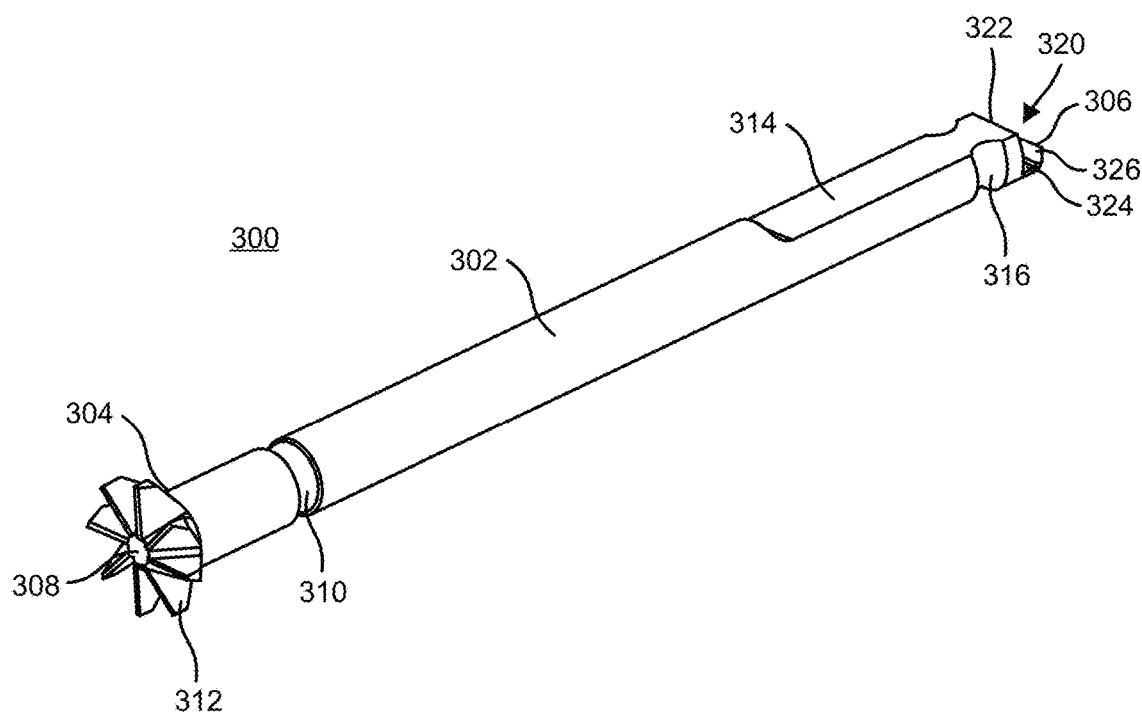
FIG. 19 is a first end perspective view of a cannulated reamer, in accordance with an aspect of the present invention.

The hole saw or trephine 250 is shown in FIGS. 15-18, for cutting to remove a circular piece of bone. The trephine 250 may include, for example, a body 252 with a first end 254 and a second end 256. The body 252 may also include an opening 264 extending from the first end 254 to the second end 256, as shown in FIG. 16. The opening 264 may be configured or sized and shaped to receive a guide wire 100. The opening 308 may include a relief 280, as shown in FIG. 16, at the second end 256 to allow for the trocar guide wire 100 to flex as it enters the opening 308 and engages the reamer 300. The first end 254 may include a plurality of teeth 258 forming a cutting edge at the first end 254 of the trephine 250. The second end 256 may include an alignment portion 260 for insertion into an instrument for rotation (not shown). Although the trephine 250 is shown as an AO mini handle it is also contemplated that the trephine 250 could have a distal end that is configured to engage alternative handles or instruments for use. The second end 256 may also include a groove 262 positioned circumferentially around the exterior surface of the body 252. Further, the second end 256 may include a coupling member 270. The coupling member 270 may include an end surface 272, an engagement surface 274 and an engagement member, ridge, protrusion, snap member or lip 276. The engagement surface 274 may be positioned adjacent and perpendicular to the end surface 272. The ridge 276 may extend away from the engagement surface 274. The ridge 276 may also be configured or sized and shaped to receive the correspondingly shaped engagement member 120 of the guide wire 100 to couple the trephine 250 to a guide wire 100. The coupling member 270 may also include an angled or chamfered edge 278 on the second end 256 of the trephine 250, as shown in FIGS. 15 and 18.

Figure 20:
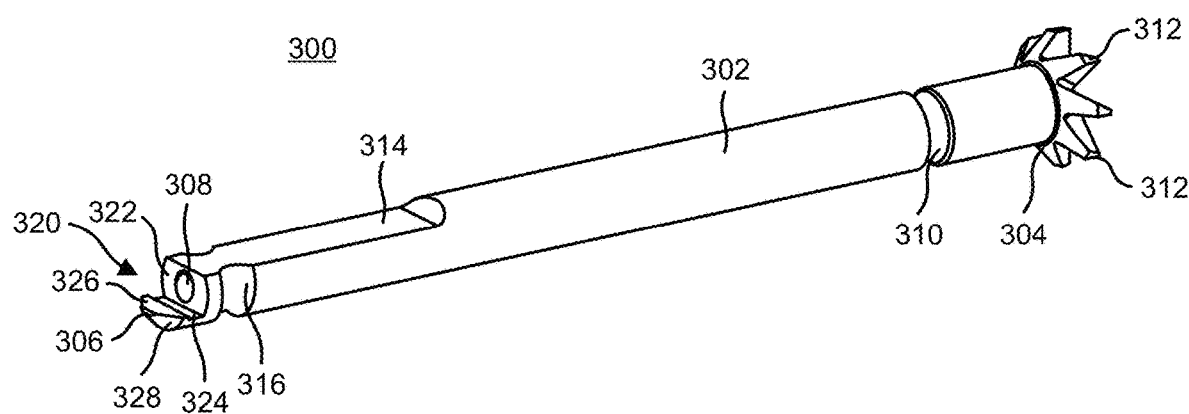
FIG. 20 is a second end perspective view of the cannulated reamer of FIG. 19, in accordance with an aspect of the present invention.
Figure 21:
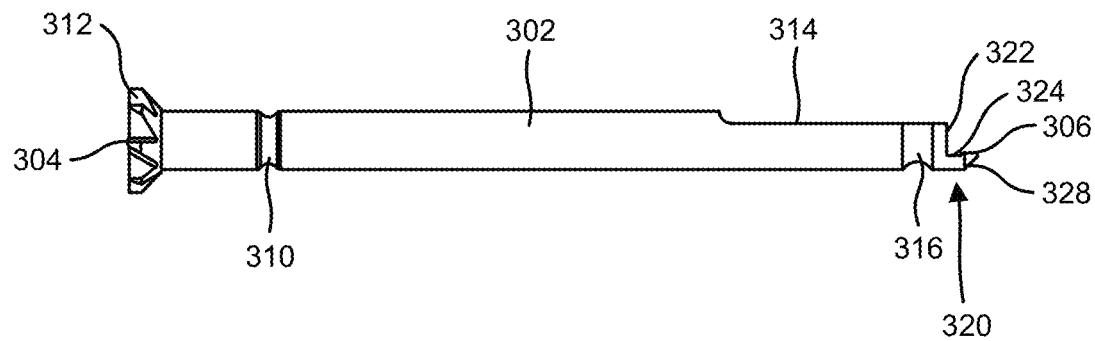
FIG. 21 is side view of the cannulated reamer of FIG. 19, in accordance with an aspect of the present invention.
Figure 22:
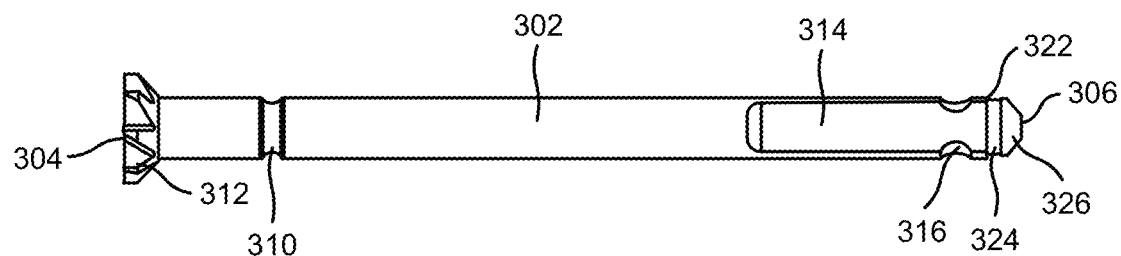
FIG. 22 is a top view of the cannulated reamer of FIG. 19, in accordance with an aspect of the present invention.

Referring now to FIGS. 19-22, a reamer or planer 300 for removing cartilage on the end of a patient's bone is shown. The reamer 300 may include a body 302 with a first end 304 and a second end 306. The reamer 300 may also include an opening 308 extending through the body 302 from the first end 304 to the second end 306. The opening 308 may be configured or sized and shaped to receive a guide wire 100. The opening 308 may also include a relief 330, as shown in FIG. 20, to allow for entry of the trocar guide wire 100 as it flexes to engage the reamer 300. The body 302 may further include a first groove 310 positioned circumferentially around the exterior surface of the body 302 near the first end 304. The first end 304 may also include a plurality of cutting members or blades 312 to ream the cartilage of a patient's bone for providing a flat bone surface for fusion of the bones. The second end 306 may include an alignment portion 314 for coupling to an instrument for rotation (not shown). Although the reamer 300 is shown as an AO mini handle it is also contemplated that the reamer 300 could have a distal end that is configured to engage alternative handles or instruments for use. The second end 306 may also include a second groove 316 positioned circumferentially around the exterior surface of the body 302. Further, the second end 306 may include a coupling member 320. The coupling member 320 may include an end surface 322, an engagement surface 324 and an engagement member, ridge, protrusion, snap member or lip 326. The engagement surface 324 may be positioned adjacent and perpendicular to the end surface 322. The ridge 326 may extend away from the engagement surface 324. The ridge 326 may also be configured or sized and shaped to receive the correspondingly shaped engagement member 120 of the guide wire 100 to couple the reamer 300 to a guide wire 100. The coupling member 320 may also include an angled or chamfered edge 328 on the second end 306 of the reamer 300, as shown in FIG. 21.

Figure 23:
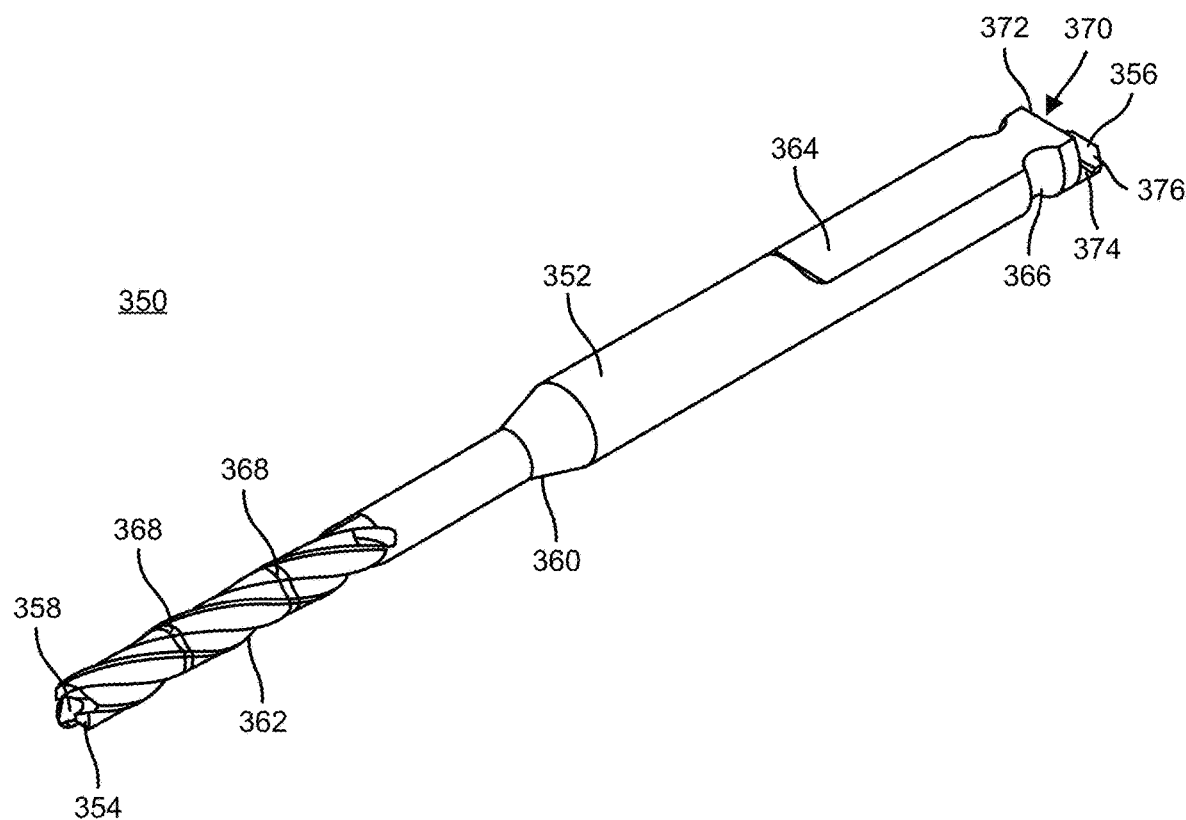
FIG. 23 is a first end, perspective view of a cannulated drill bit, in accordance with an aspect of the present invention.
Figure 24:
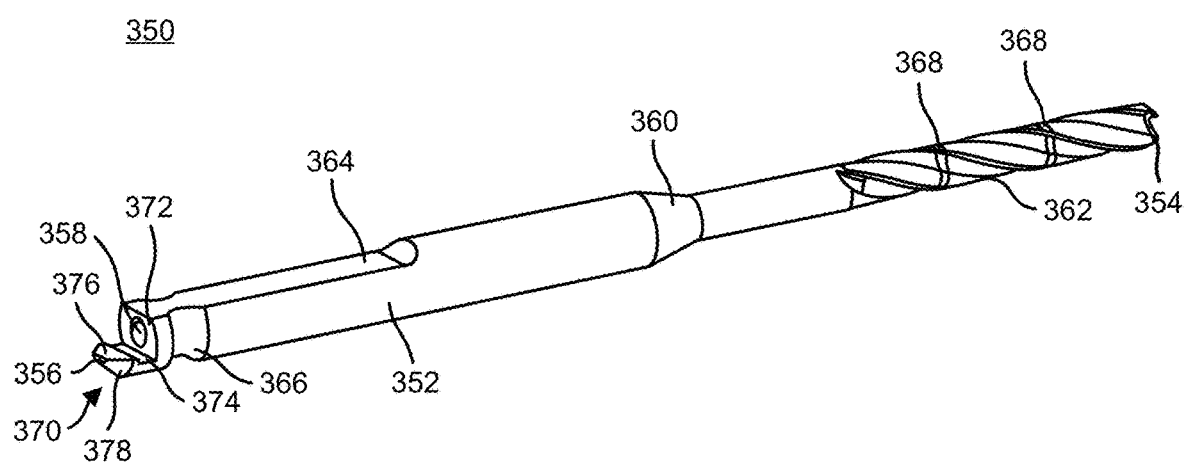
FIG. 24 is a second end, perspective view of the cannulated drill bit of FIG. 23, in accordance with an aspect of the present invention.
Figure 25:
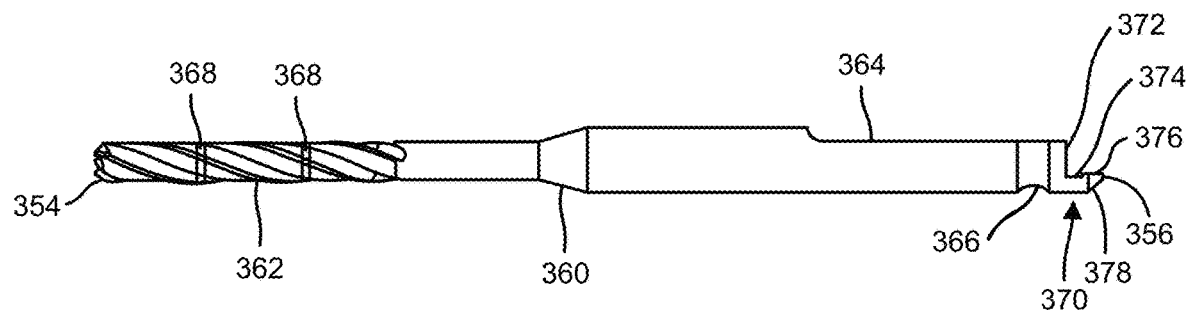
FIG. 25 is a side view of the cannulated drill bit of FIG. 23, in accordance with an aspect of the present invention.
Figure 26:
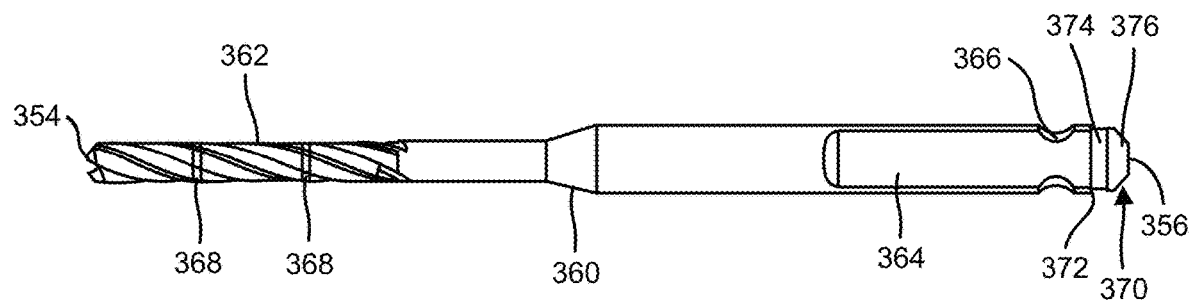
FIG. 26 is a top view of the cannulated drill bit of FIG. 23, in accordance with an aspect of the present invention.

As shown in FIGS. 23-26, a first drill bit 350 for drilling an opening in the bone is shown. The first drill bit 350 may include a body 352 with a first end 354 and a second end 356. The body 352 may also include an opening 358 extending from the first end 354 to the second end 356 through the body 352, as shown in FIGS. 23 and 24. The body 352 may have a neck portion 360 that tapers from a central portion to the first end 354 of the body 352. The first end 354 may also include cutting edges 362. The first end 354 may further include at least one laser marking 368. In the depicted embodiment, the at least one laser marking 368 is, for example, two laser markings spaced equally apart from the distal end 354 of the body 352 on the cutting edges 362. The second end 356 may include an alignment portion 364 for coupling to an instrument for rotation (not shown). Although the first drill bit 350 is shown as an AO mini handle it is also contemplated that the first drill bit 350 could have a distal end that is configured to engage alternative handles or instruments for use. The second end 356 may also include a groove 366 positioned circumferentially around the exterior surface of the body 352. Further, the second end 366 may include a coupling member 370. The coupling member 370 may include an end surface 372, an engagement surface 374 and an engagement member, ridge, protrusion, snap member or lip 376. The engagement surface 374 may be positioned adjacent and perpendicular to the end surface 372. The ridge 376 may extend away from the engagement surface 374. The ridge 376 may also be configured or sized and shaped to receive the correspondingly shaped engagement member 120 of the guide wire 100 to couple the first drill bit 350 to a guide wire 100. The opening 358 may also include a relief 380, as shown in FIG. 24, to allow for the trocar guide wire 100 to flex as the coupling member 110 of the guide wire 100 engage the coupling member 370 of the first drill bit 350. The coupling member 370 may further include an angled or chamfered edge 378 on the second end 356 of the first drill bit 350, as shown in FIGS. 24 and 25.

Figure 27:
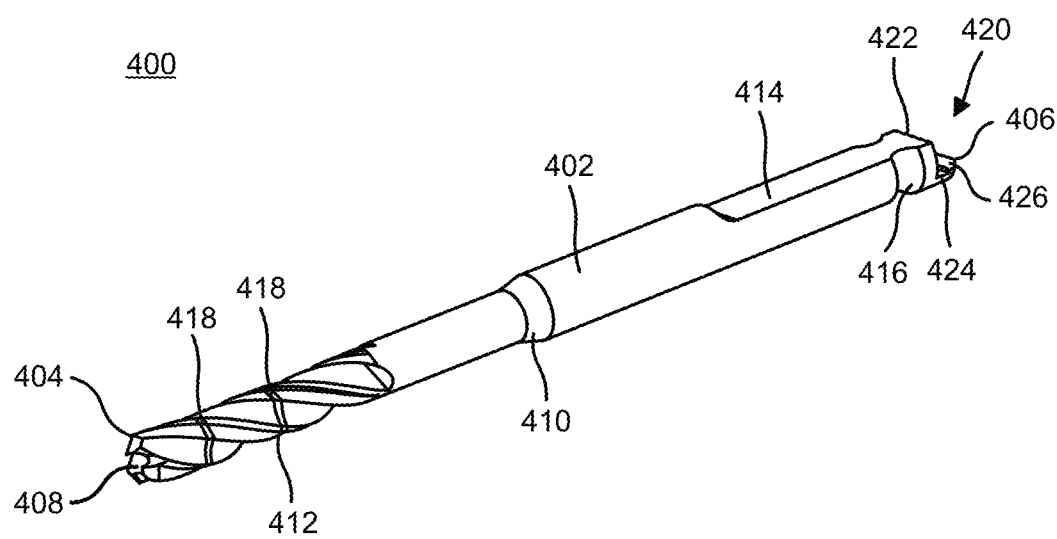
FIG. 27 is a first end, perspective view of another embodiment of a cannulated drill bit, in accordance with an aspect of the present invention.
Figure 28:
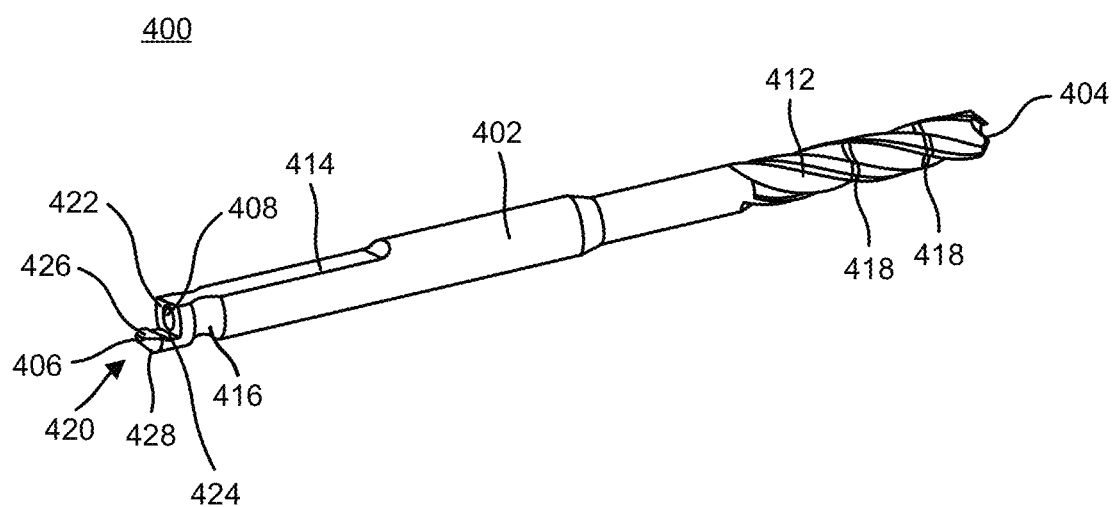
FIG. 28 is a second end, perspective view of the cannulated drill bit of FIG. 27, in accordance with an aspect of the present invention.
Figure 29:
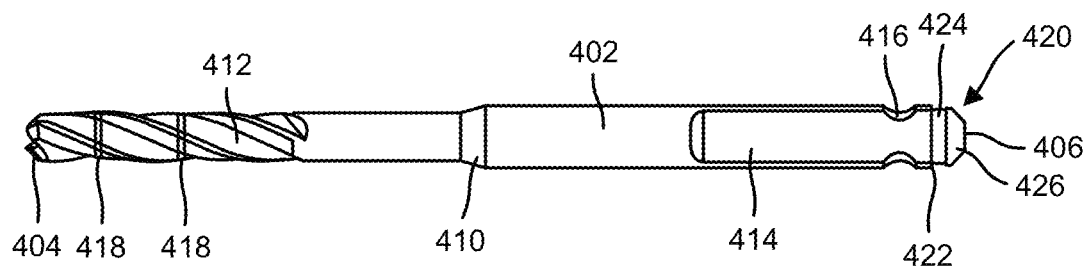
FIG. 29 is a top view of the cannulated drill bit of FIG. 27, in accordance with an aspect of the present invention.
Figure 30:
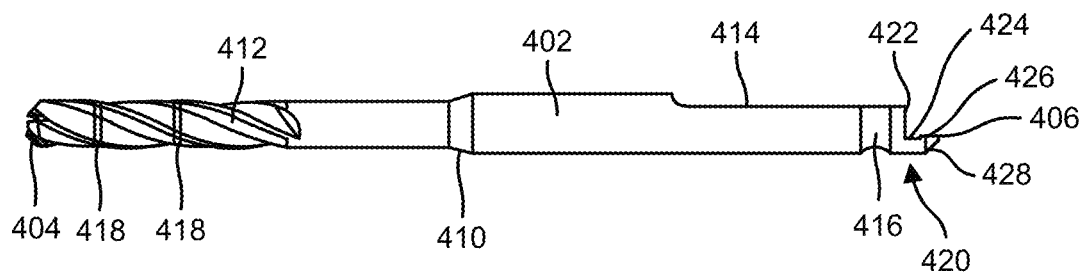
FIG. 30 is a side view of the cannulated drill bit of FIG. 27, in accordance with an aspect of the present invention.
Figure 31:
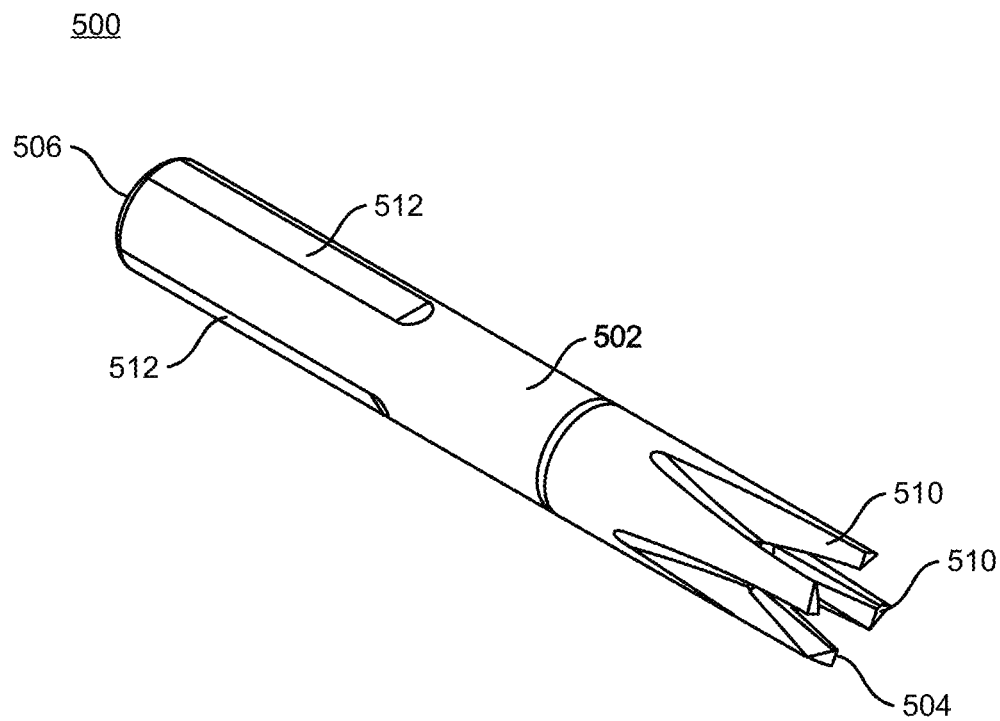
FIG. 31 is a perspective view of a first cutter, in accordance with an aspect of the present invention.
Figure 32:
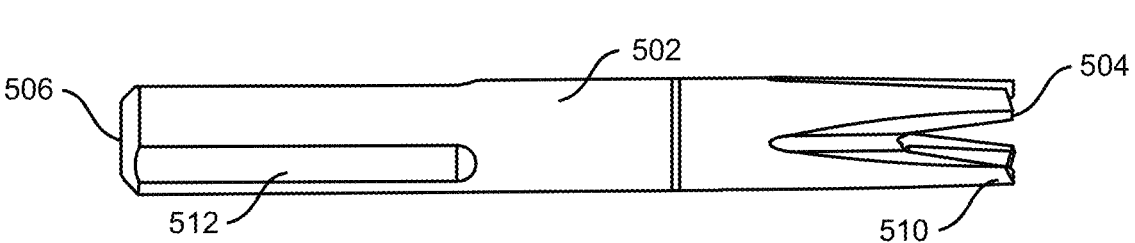
FIG. 32 is a side view of the first cutter of FIG. 31, in accordance with an aspect of the present invention.

Referring now to FIGS. 27-30, a second drill bit 400 for drilling the patient's bone is shown. The second drill bit 400 may include a body 402 with a first end 404 and a second end 406. The body 402 may also include an opening 408 extending from the first end 404 to the second end 406 through the body 402, as shown in FIGS. 27 and 28. The body 402 may have a neck portion 410 that tapers from a central portion to the first end 404 of the body 402. The first end 404 may also include cutting edges 412. The first end 404 may further include at least one laser marking 418. In the depicted embodiment, the at least one laser marking 418 is, for example, two laser markings 418 spaced equally apart from the distal end 404 of the body 402 on the cutting edges 412. The second end 406 may include an alignment portion 414 for coupling to an instrument for rotation (not shown). Although the second drill bit 400 is shown as an AO mini handle it is also contemplated that the second drill bit 400 could have a distal end that is configured to engage alternative handles or instruments for use. The second end 406 may also include a groove 416 positioned circumferentially around the exterior surface of the body 402. Further, the second end 406 may include a coupling member 420. The coupling member 420 may include an end surface 422, an engagement surface 424 and an engagement member, ridge, protrusion, snap member or lip 426. The engagement surface 424 may be positioned adjacent and perpendicular to the end surface 422. The ridge 426 may extend away from the engagement surface 424. The ridge 426 may also be configured or sized and shaped to receive the correspondingly shaped engagement member 120 of the guide wire 100 to couple the second drill bit 400 to a guide wire 100. The coupling member 420 may also include an angled or chamfered edge 428 on the second end 406 of the second drill bit 400, as shown in FIGS. 28 and 30. The opening 408 may also include a relief 430, as shown in FIG. 28, to allow for the trocar guide wire 100 to flex as the coupling member 110 of the guide wire 100 engage the coupling member 420 of the second drill bit 400. The second drill bit 400 may have, for example, a larger diameter than the first drill bit 350.

Figure 33:
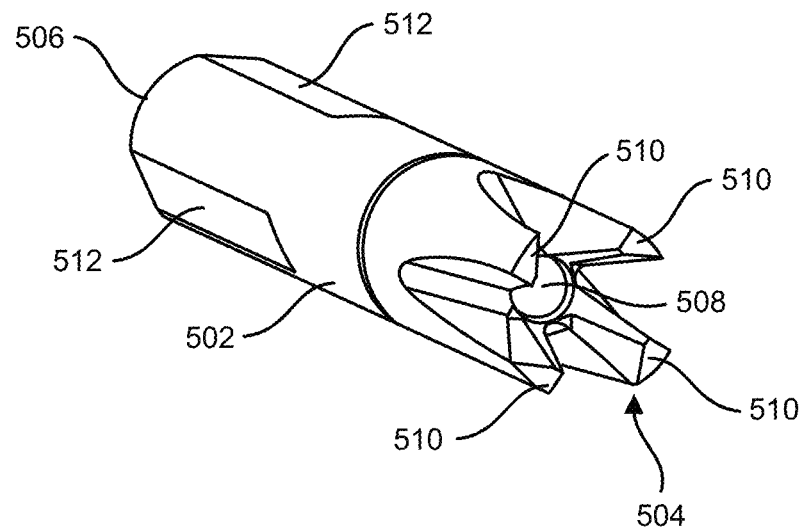
FIG. 33 is a first end, perspective view of the first cutter of FIG. 31, in accordance with an aspect of the present invention.
Figure 34A:
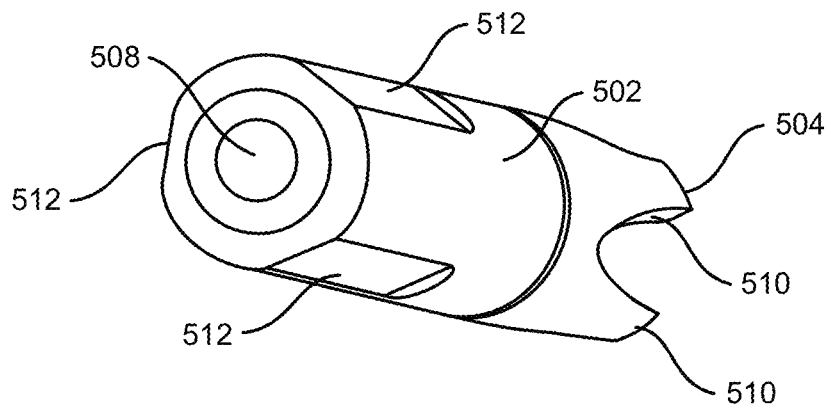
FIG. 34A is a second end, perspective view of the first cutter of FIG. 31, in accordance with an aspect of the present invention.
Figure 34B:
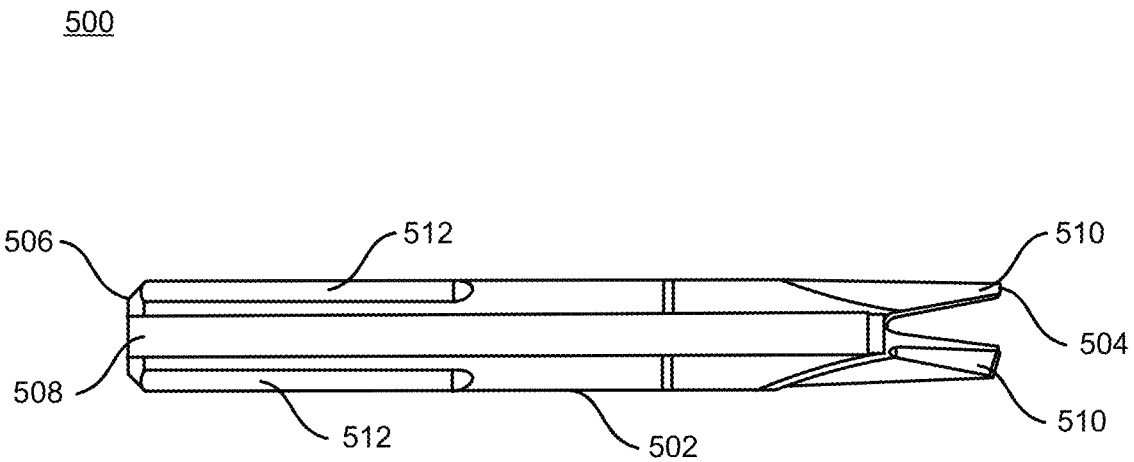
FIG. 34B is a cross sectional view of the first cutter of FIG. 31 taken along line 34B-34B in FIG. 34A, in accordance with an aspect of the present invention.
Figure 35:
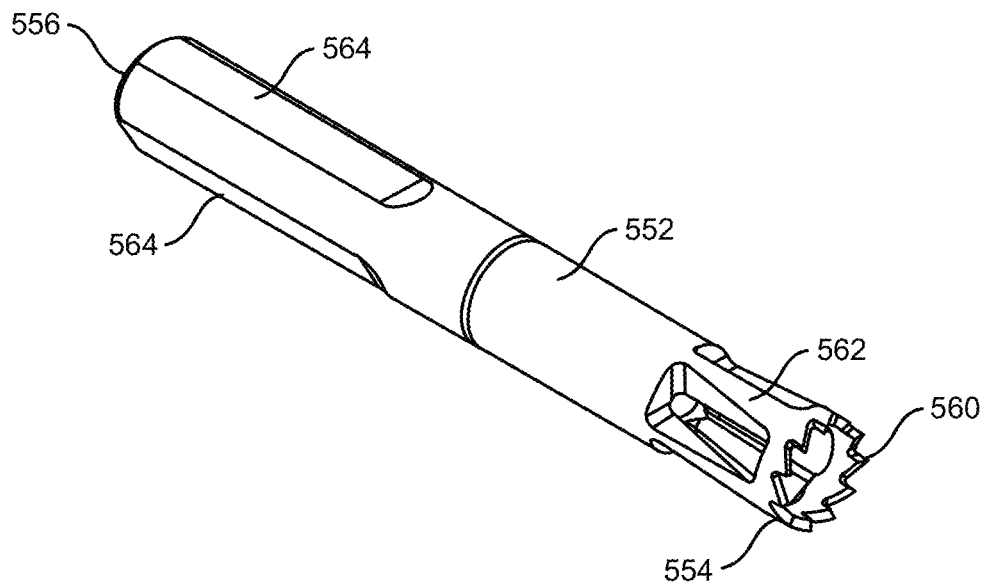
FIG. 35 is a perspective view of a second cutter, in accordance with an aspect of the present invention.
Figure 36:
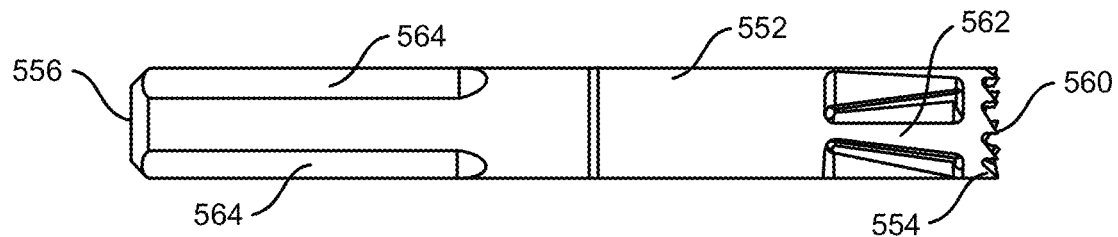
FIG. 36 is a side view of the second cutter of FIG. 35, in accordance with an aspect of the present invention.
Figure 39:
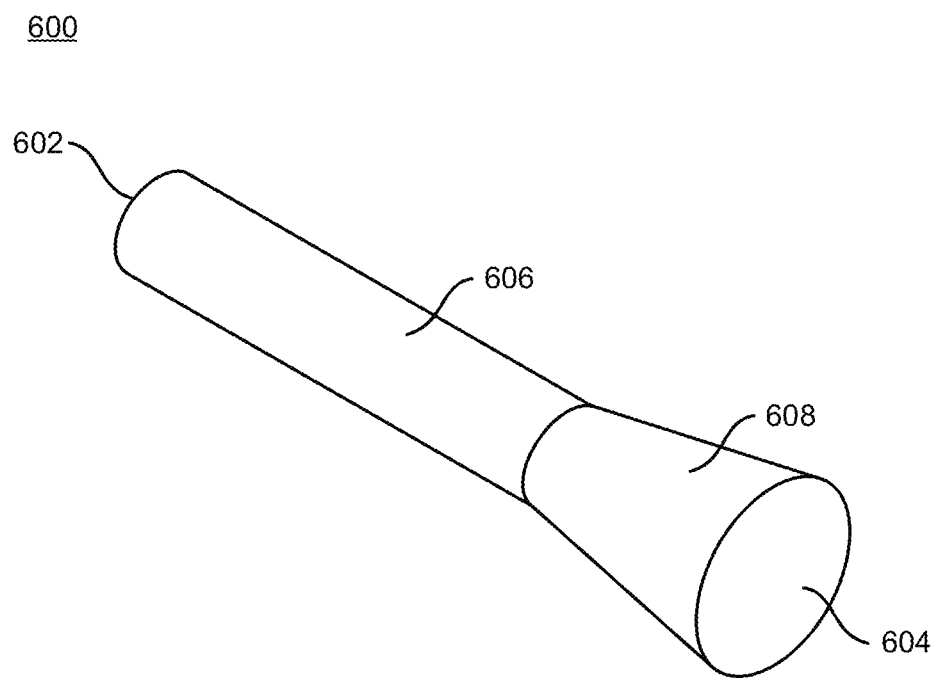
FIG. 39 is a perspective view of a portion of bone for forming an implant, in accordance with an aspect of the present invention.
Figure 40:
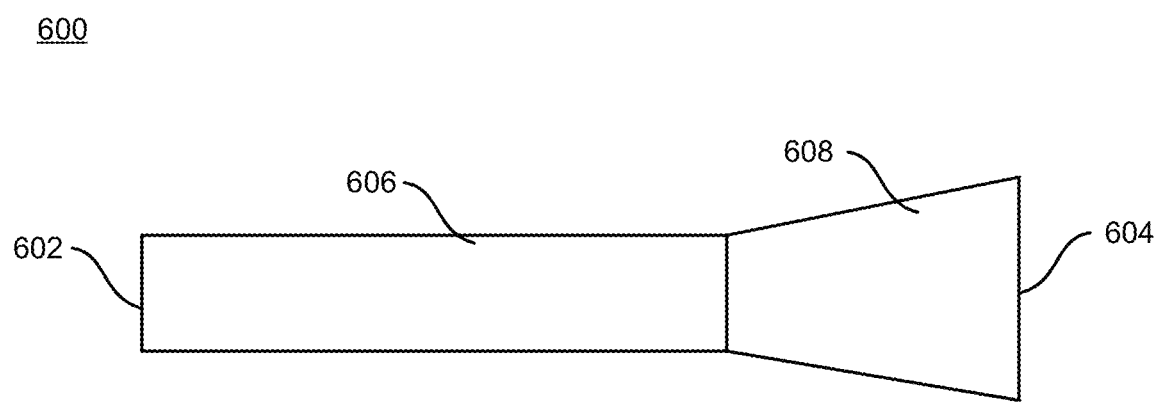
FIG. 40 is a side view of the portion of bone of FIG. 39, in accordance with an aspect of the present invention.
Figure 41:
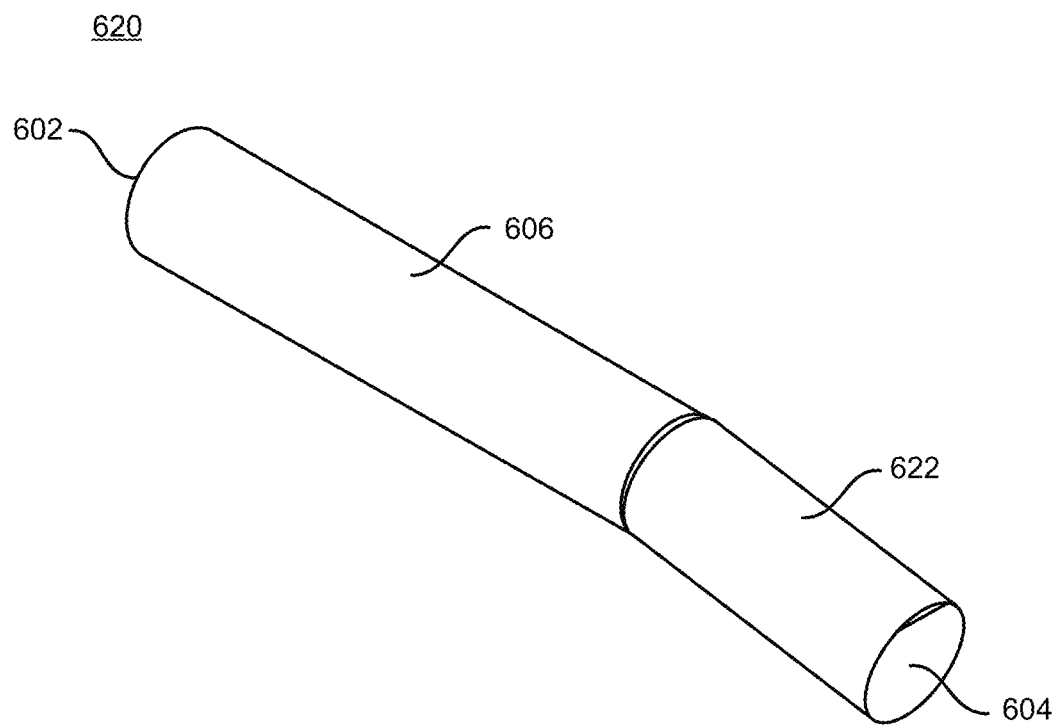
FIG. 41 is a perspective view of a shaped portion of bone, in accordance with an aspect of the present invention.

Referring now to FIGS. 31-64, tapered reamer cutters 500, 550 and implants 620, 640, 660, 680 are illustrated. As shown in FIGS. 31-34B, a first tapered reamer cutter 500 is shown. The cutter 500 includes a body 502 with a first end 504 and a second end 506. The cutter 500 also includes an opening 508 extending from a first end 504 to a second end 506 through the body 502, as shown in FIGS. 33-34B. The first end 504 includes a plurality of arms 510 extending away from the body 502. The plurality of arms 510 may be angled or tapered on an interior surface of the body 502, as shown in FIG. 34B. The plurality of arms 510 may also be cutting arms for cutting the implant to the desired shape, such as, the shape of the bone portion 600 with a cylindrical portion and a cone shaped portion, as shown in FIGS. 39 and 40. The second end 506 of the body 502 may include at least one alignment surface or flat surface 512. The alignment surface 512 allows for coupling to an instrument to allow for the cutter 500 to be rotated to make a cut or to shape an implant.

Figure 37:
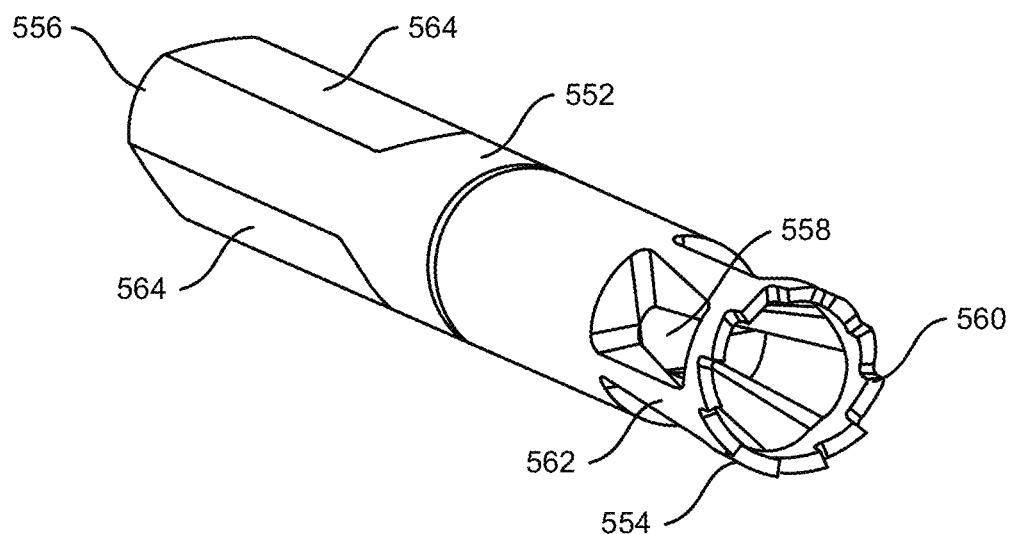
FIG. 37 is a first end, perspective view of the second cutter of FIG. 35, in accordance with an aspect of the present invention.
Figure 38A:
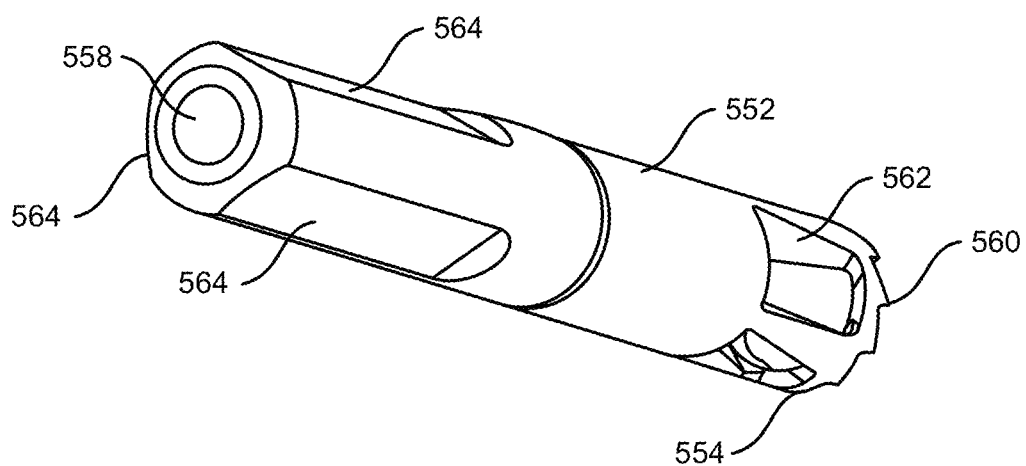
FIG. 38A is a second end, perspective view of the second cutter of FIG. 35, in accordance with an aspect of the present invention.
Figure 38B:
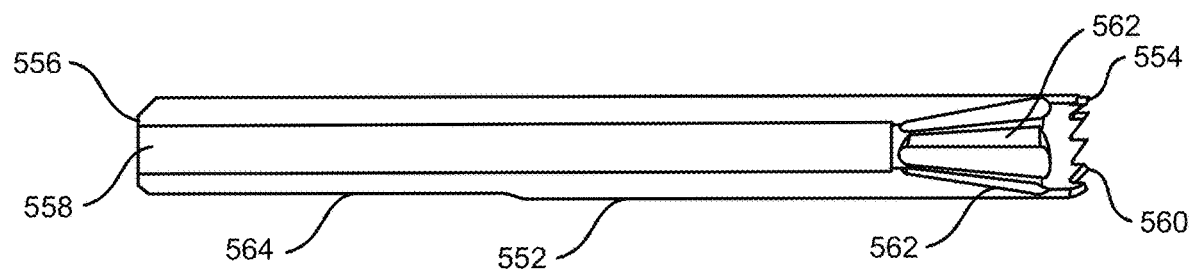
FIG. 38B is a cross sectional view of the second cutter of FIG. 35 taken along line 38B-38B in FIG. 38A, in accordance with an aspect of the present invention.

A second tapered reamer cutter 550 is shown in FIGS. 35-38B. The second cutter 550 includes a body 552 with a first end 554 and a second end 556. The cutter 550 may also include an opening 558 extending from the first end 554 to the second end 556 through the body 552, as shown in FIGS. 37-38B. The first end 554 includes a plurality of teeth 560 positioned around the distal surface of the cutter 550. The first end 554 may also include a frame 562, as shown in FIG. 38B, with additional cutting members positioned to form, for example, an angled interior cutting surface to cut a bone, such as the second end 604 of the implant 620, at a desired angle. The second end 556 of the body 552 may include at least one alignment surface or flat surface 564. The alignment surface 564 allows for coupling to an instrument to allow for the cutter 550 to be rotated to cut or to shape an implant.

A method of forming an implant 680 is shown in FIGS. 39-65. The method may include obtaining a bone graft material and using the first cutter 500 to shape the bone graft material to form a first bone member 600, as shown in FIGS. 39-40. The first cutter 500 may be used to cut the first bone member 600 to form a first body portion 606 and a second body portion 608. After the first bone member 600 is cut with the first cutter 500, the first body portion 606 may be positioned at the first end 602 and may have, for example, a cylindrical tube shape, and the second body portion 608 may be positioned at the second end 604 and may have, for example, a cone shape. Next, the first body portion 606 of the implant 600 may be placed into a fixture block (not shown) at an angle from a longitudinal axis. The angle may range from, for example, approximately 0-30 degrees, and more specifically may be approximately 10 degrees.

Figure 42:
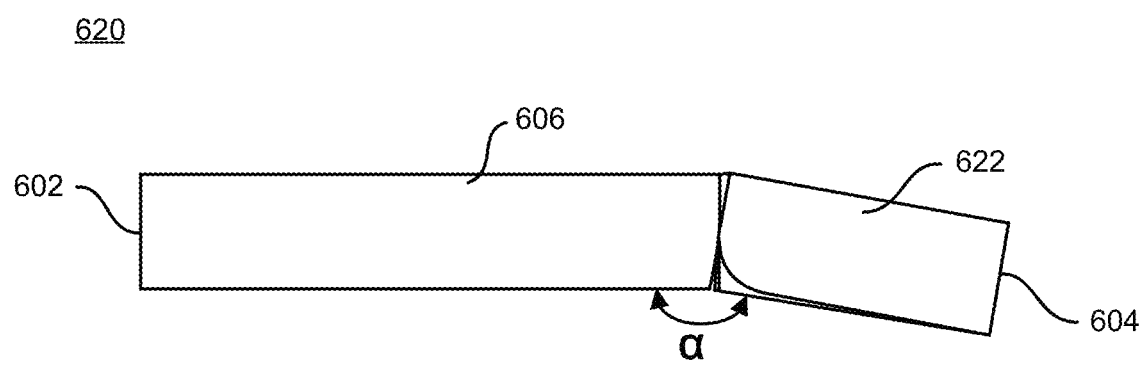
FIG. 42 is a side view of the shaped portion of bone of FIG. 41, in accordance with an aspect of the present invention.
Figure 43:
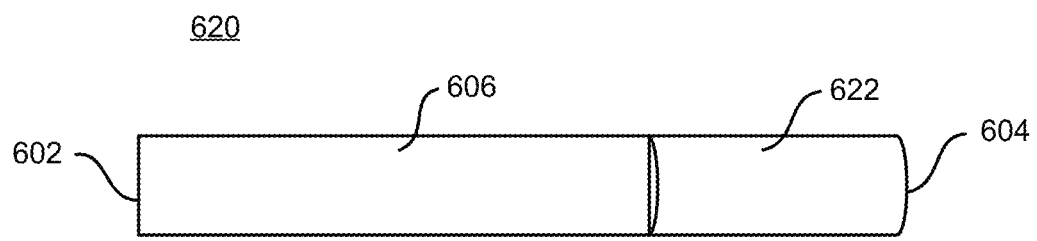
FIG. 43 is a top view of the shaped portion of bone of FIG. 41, in accordance with an aspect of the present invention.
Figure 44:
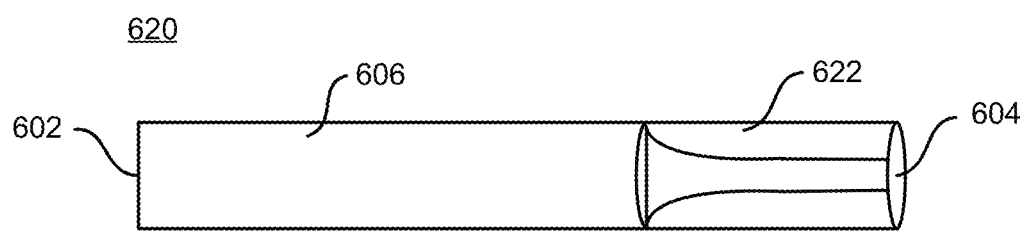
FIG. 44 is a bottom view of the shaped portion of bone of FIG. 41, in accordance with an aspect of the present invention.
Figure 45:
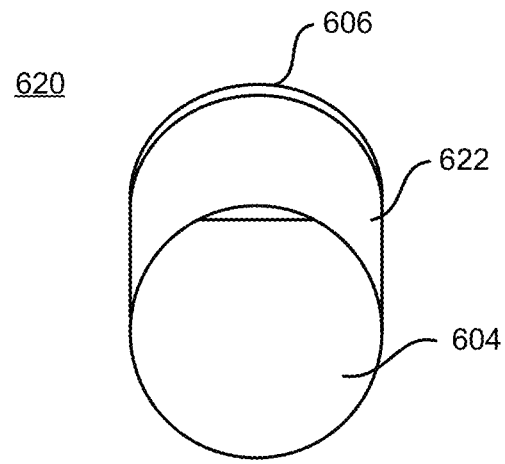
FIG. 45 is a first end view of the shaped portion of bone of FIG. 41, in accordance with an aspect of the present invention.
Figure 46:
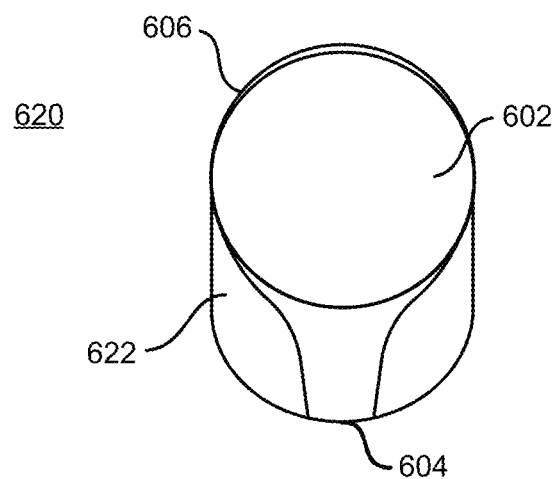
FIG. 46 is a second end view of the shaped portion of bone of FIG. 41, in accordance with an aspect of the present invention.

Then, the first bone member 600 may be further cut to form a second bone member 620, as shown in FIGS. 41-46. The second bone member 620 may include the first body portion 606 and a second body portion 622. The second body portion 622 may be formed using the second cutter 550. The second cutter 550 may enter the second end 604 of the first bone member 600 to form the second body portion 622. The second body portion 622 of the second bone member 620 may have, for example, a cylindrical tube shape, and the second body portion 622 may be positioned at an angle α relative to the first body portion 606 along the longitudinal axis of the bone member 620. As shown in FIG. 42, the angle α may be, for example, approximately 0° to 30°, and more specifically approximately 10 degrees. It is also contemplated that the implant 620 may be a straight bone portion without an angle, as shown in FIGS. 92-97 and described in greater detail below.

Figure 47:
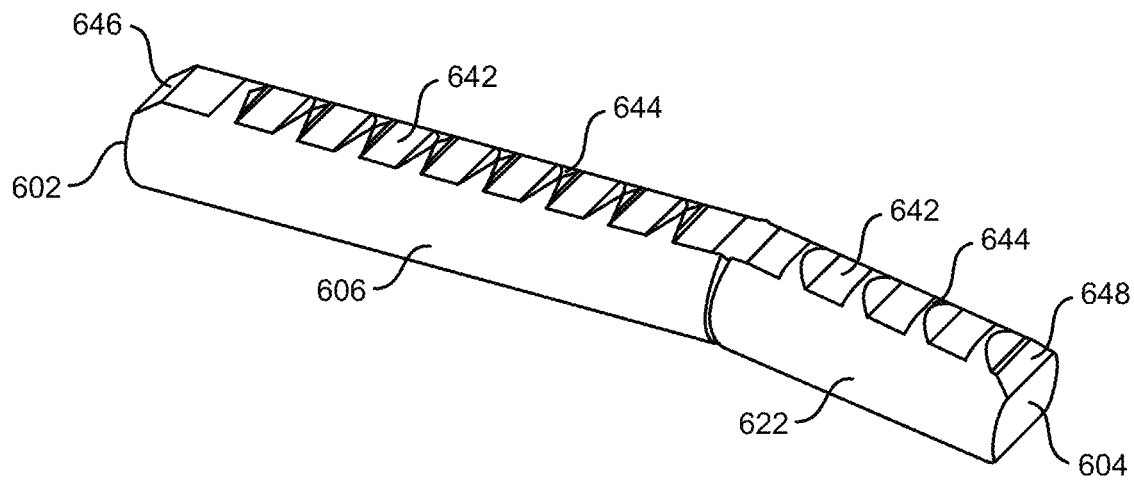
FIG. 47 is a perspective view of an implant formed from the portion of bone of FIG. 41, including ridges in the dorsal and plantar surfaces, in accordance with an aspect of the present invention.
Figure 48:
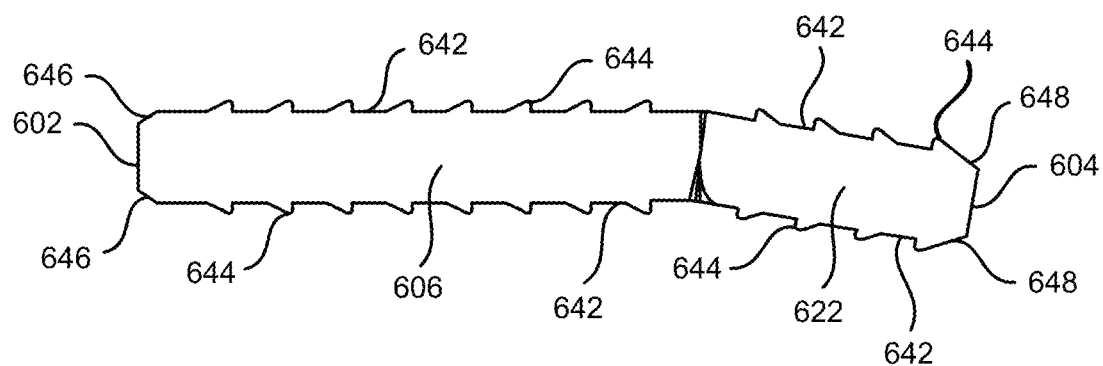
FIG. 48 is a side view of the implant of FIG. 47, in accordance with an aspect of the present invention.
Figure 49:
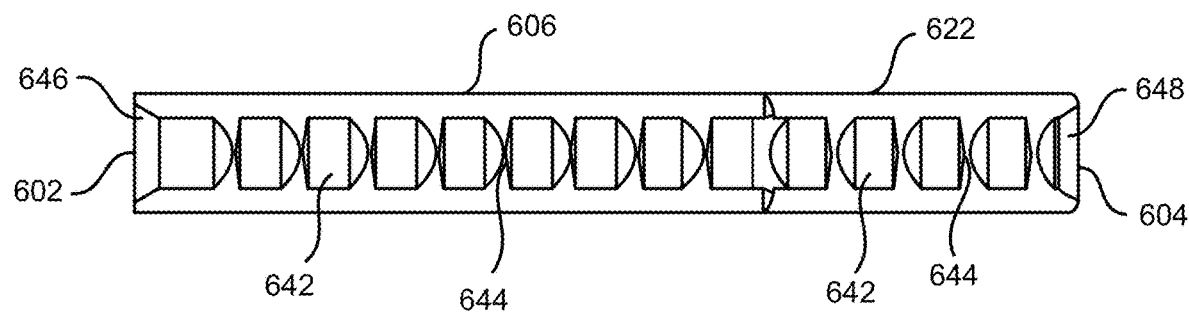
FIG. 49 is a top view of the implant of FIG. 47, in accordance with an aspect of the present invention.
Figure 50:
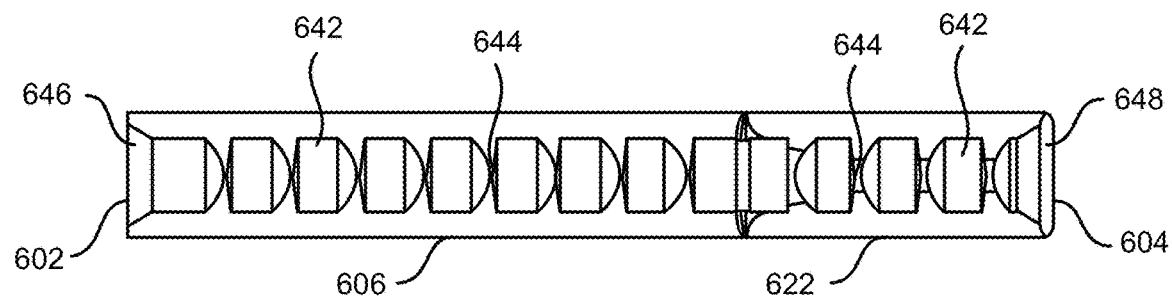
FIG. 50 is a bottom view of the implant of FIG. 47, in accordance with an aspect of the present invention.
Figure 51:
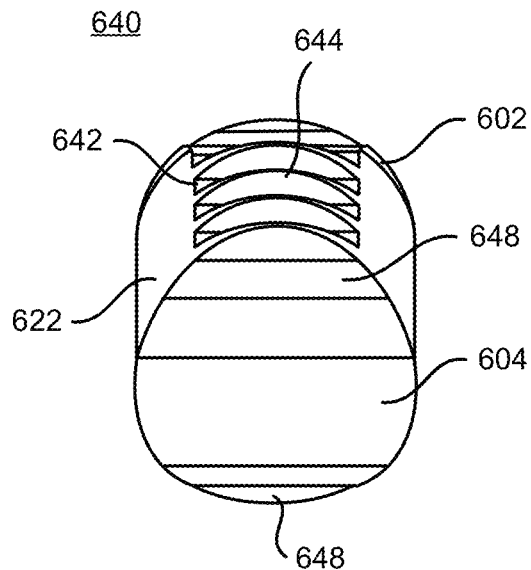
FIG. 51 is a first end view of the implant of FIG. 47, in accordance with an aspect of the present invention.
Figure 52:
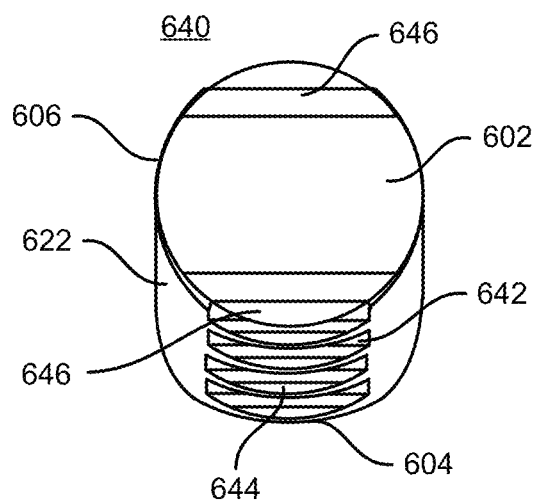
FIG. 52 is a second end view of the implant of FIG. 47, in accordance with an aspect of the present invention.
Figure 53:
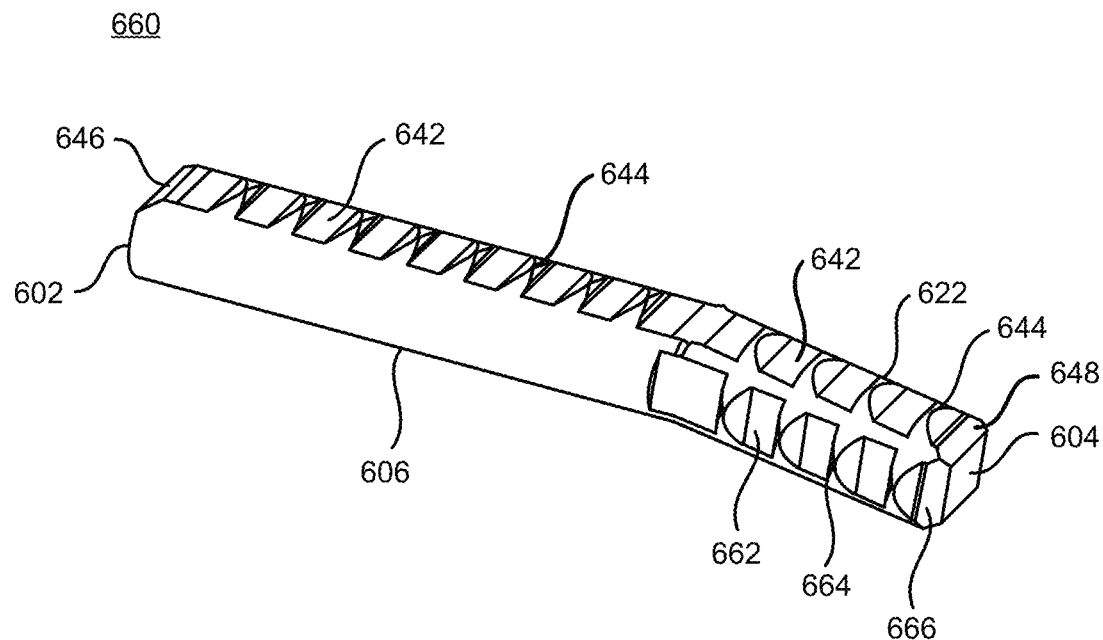
FIG. 53 is a perspective view of an implant formed from the implant of FIG. 47, and also includes ridges on the medial and lateral sides of the first end of the implant, in accordance with an aspect of the present invention.
Figure 54:
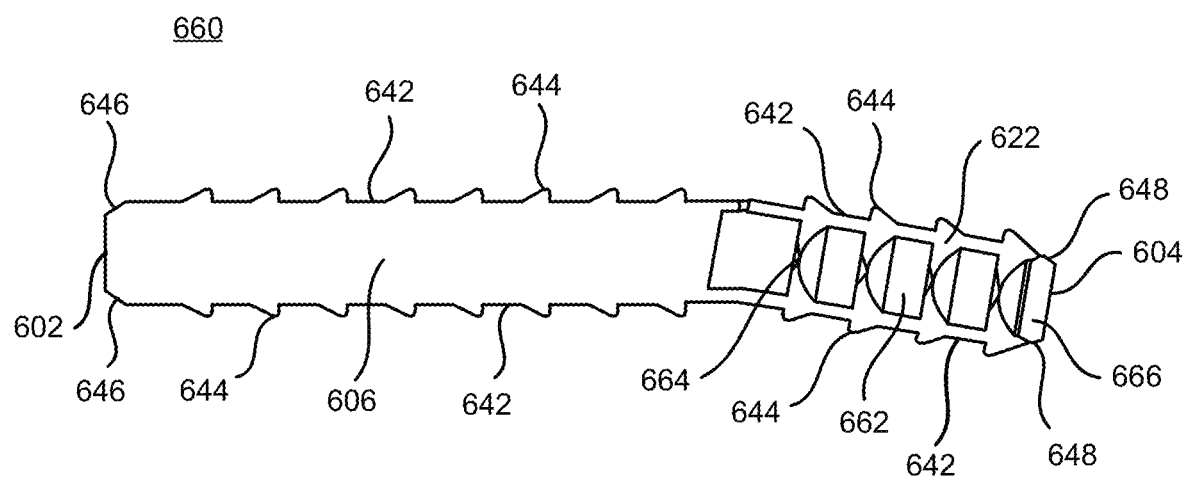
FIG. 54 is a side view of the implant of FIG. 53, in accordance with an aspect of the present invention.

After the first body portion 606 and the second body portion 622 are formed, the second bone member 620 may be further processed to form implant 640, as shown in FIGS. 47-52. The implant 640 may include, for example, a plurality of grooves, recesses, teeth, ridges 642 recessed into the dorsal and plantar surfaces of the implant 640. The recesses 642 may form ribs or projections 644 between adjacent recesses 642 and the ribs 644 may extend out from the dorsal and plantar surfaces of the implant 640, as shown in FIG. 48. The ribs 644 may be positioned, for example, approximately 1 mm to 2 mm from the adjacent ribs 644, more specifically, the ribs 644 may be spaced 1.5 mm apart. The recesses 642 and ribs 644 may be formed in the implant 640 using, for example, a broaching press having a plate with cutting edges to correspond to the recesses 642 and ribs 644. The implant 640 may also include tapered or angled edges 646 at the first end 602 and tapered or angled edges 648 at the second end 604, as shown in FIGS. 47 and 48. The tapered edges 646, 648 may be on the dorsal and plantar surfaces of the implant 640.

Figure 55:
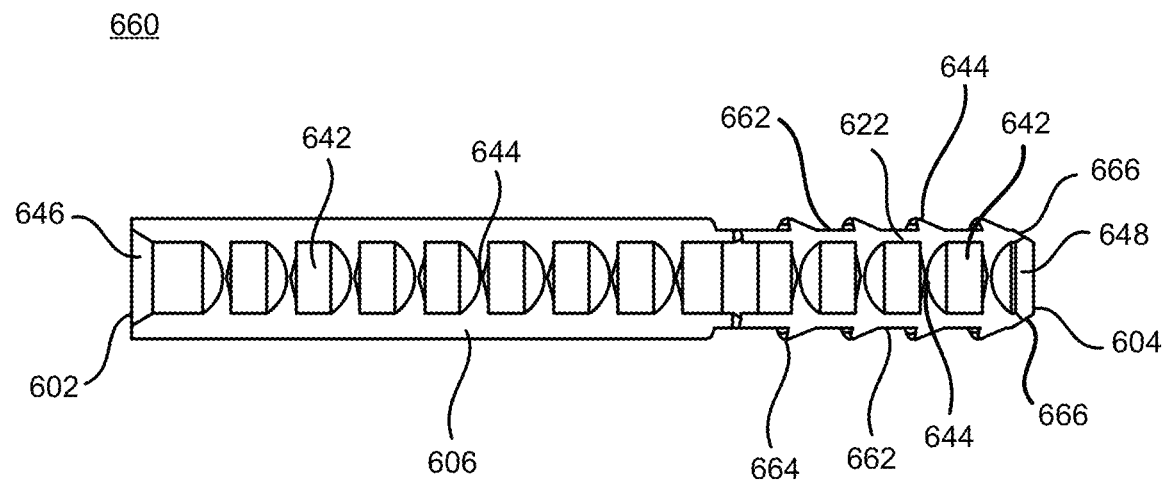
FIG. 55 is a top view of the implant of FIG. 53, in accordance with an aspect of the present invention.
Figure 56:
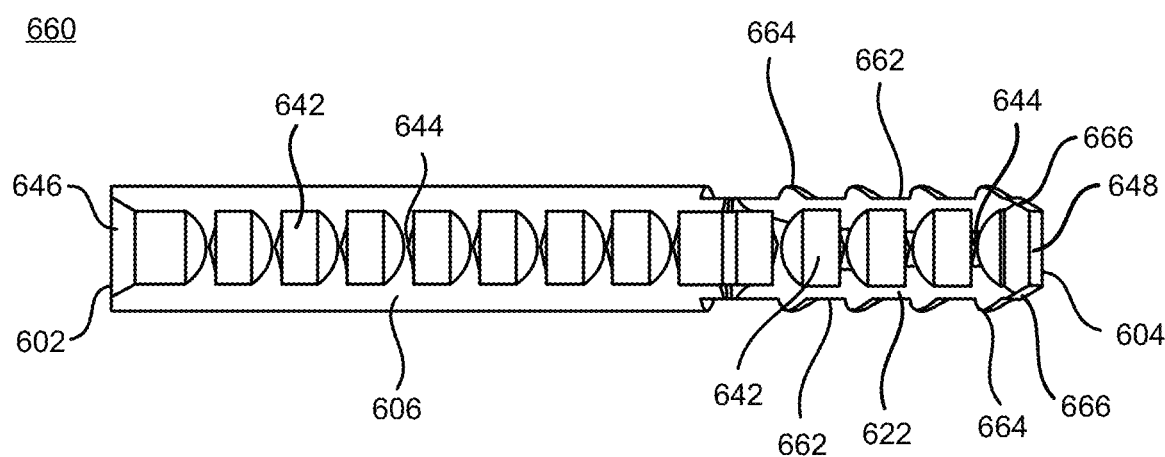
FIG. 56 is a bottom view of the implant of FIG. 53, in accordance with an aspect of the present invention.
Figure 57:
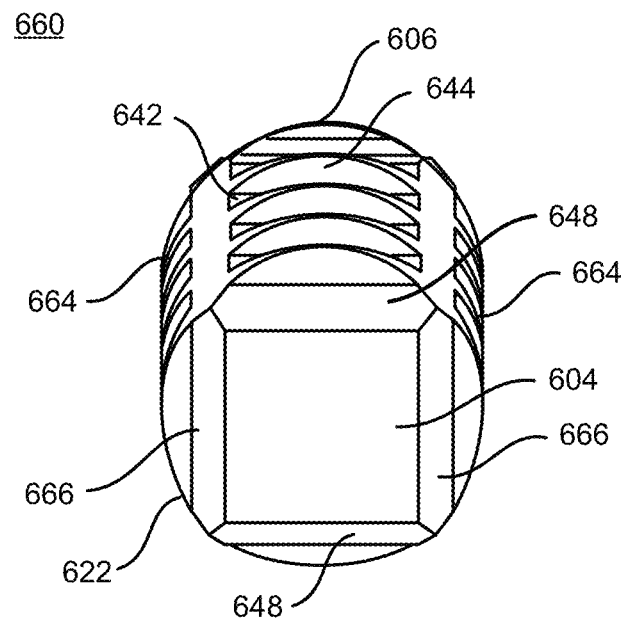
FIG. 57 is a first end view of the implant of FIG. 53, in accordance with an aspect of the present invention.
Figure 58:
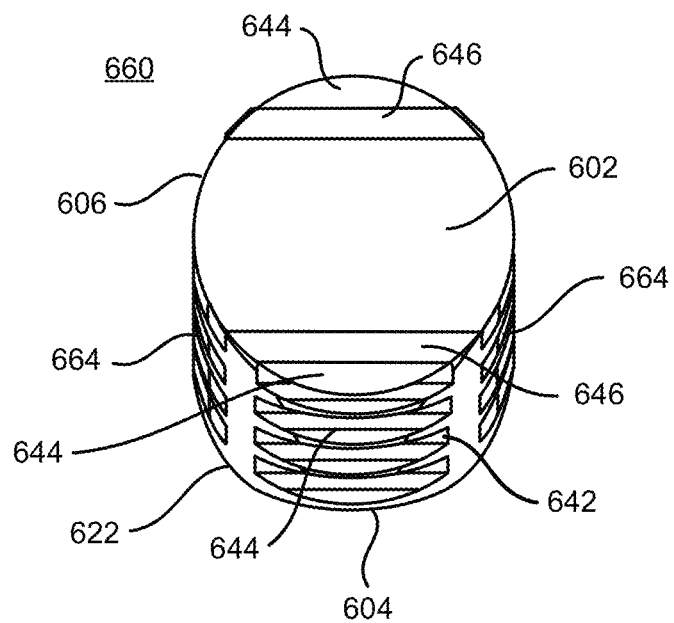
FIG. 58 is a second end view of the implant of FIG. 53, in accordance with an aspect of the present invention.
Figure 59:
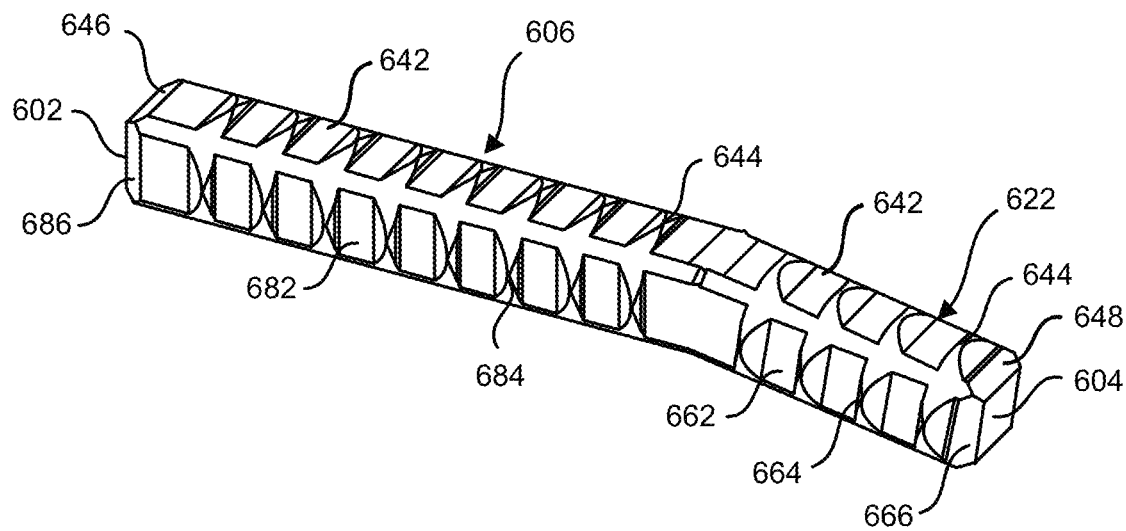
FIG. 59 is a perspective view of an implant formed from the implant of FIG. 53, and also includes ridges on the medial and lateral sides of the second end of the implant, in accordance with an aspect of the present invention.
Figure 60:
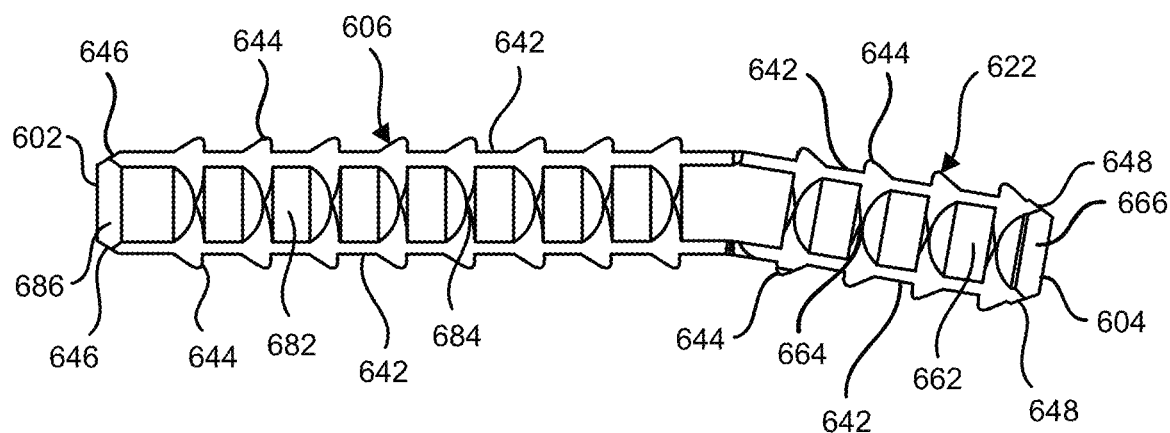
FIG. 60 is a side view of the implant of FIG. 59, in accordance with an aspect of the present invention.

As shown in FIGS. 53-58, the implant 640 may be further changed to form implant 660. The implant 660 may include another set of a plurality of grooves, channels, or recesses 662. The grooves 662 may be recessed into the medial and lateral surfaces of the second body portion 622 of the implant 660, as shown in FIGS. 55-58. The grooves 662 may form ribs, teeth, ridges or projections 664 positioned between the adjacent grooves 662. The ribs 664 may extend out from the lateral and medial surfaces of the implant 660, as shown in FIGS. 55 and 56. The ribs 664 may be positioned, for example, approximately 1 mm to 2 mm from the adjacent ribs 664, more specifically, the ribs 664 may be spaced 1.5 mm apart. The recesses 662 and ribs 664 may be formed in the implant 660 using, for example, a broaching press having a plate with cutting edges to correspond to the recesses 662 and ribs 664. The implant 660 may also include tapered or angled edges 666 at the second end 604, as shown in FIGS. 55-58. The tapered edges 666 may be on the medial and lateral surfaces of the implant 660.

Figure 61:
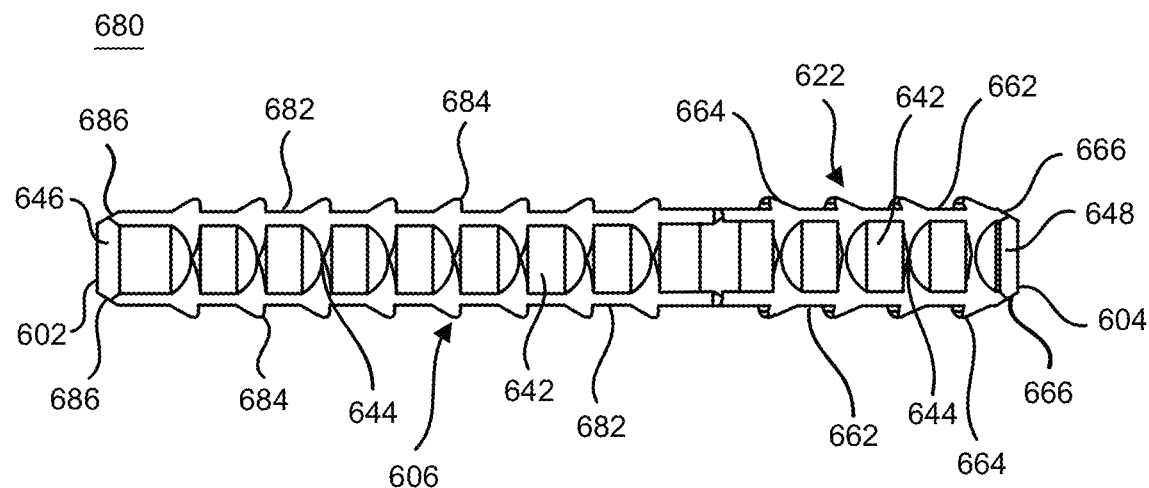
FIG. 61 is a top view of the implant of FIG. 59, in accordance with an aspect of the present invention.
Figure 62:
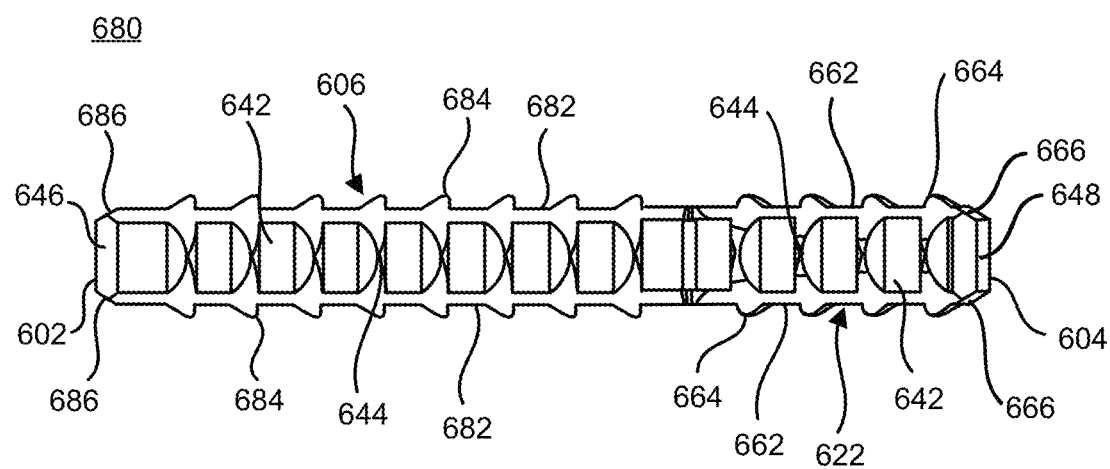
FIG. 62 is a bottom view of the implant of FIG. 59, in accordance with an aspect of the present invention.

The implant 660 may then be modified through additional processing to form the implant 680, as shown in FIGS. 59-64. The additional processing may include pushing the implant 660 through, for example, a plate of a broaching press. The plate may include cutting edges to correspond to the recesses 682 and ribs 684 formed in the implant 680. The implant 680 may include another set of a plurality of grooves, channels, or recesses 682. The grooves 682 may be recessed into the medial and lateral surfaces of the first body portion 606 of the implant 680, as shown in FIGS. 61-64. The grooves 682 may form ribs, teeth, ridges or projections 684 positioned between the adjacent grooves 682. The ribs 684 may extend out from the lateral and medial surfaces of the implant 680, as shown in FIGS. 61 and 62. The ribs 684 may be positioned, for example, approximately 1 mm to 2 mm from the adjacent ribs 684, more specifically, the ribs 684 may be spaced 1.5 mm apart. The implant 680 may also include tapered or angled edges 686 at the first end 602, as shown in FIGS. 61-64. The tapered edges 686 may be on the medial and lateral surface of the implant 680.

Figure 63:
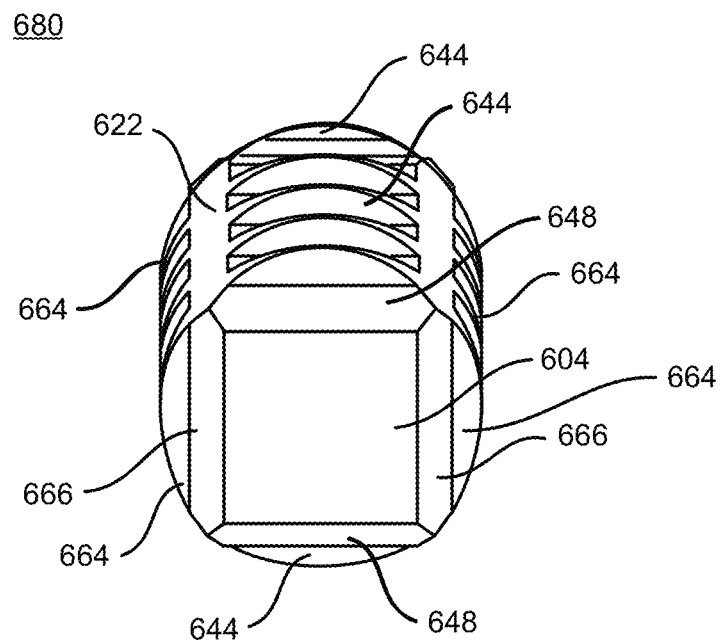
FIG. 63 is a first end view of the implant of FIG. 59, in accordance with an aspect of the present invention.
Figure 64:
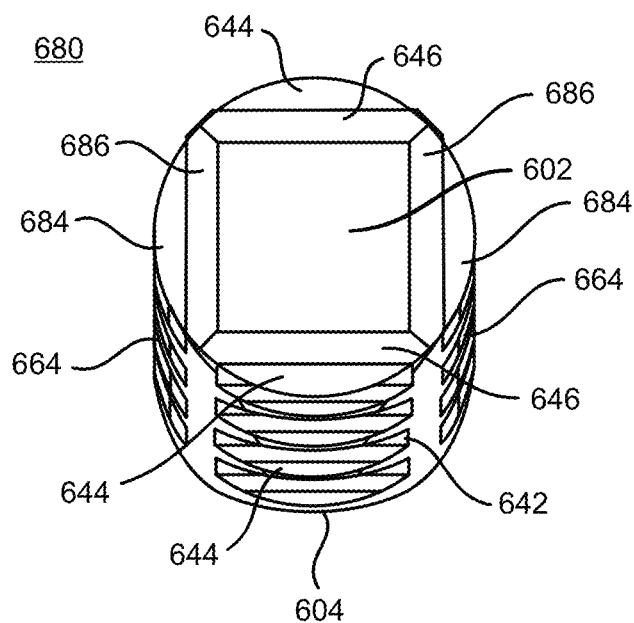
FIG. 64 is a second end view of the implant of FIG. 59, in accordance with an aspect of the present invention.
Figure 65:
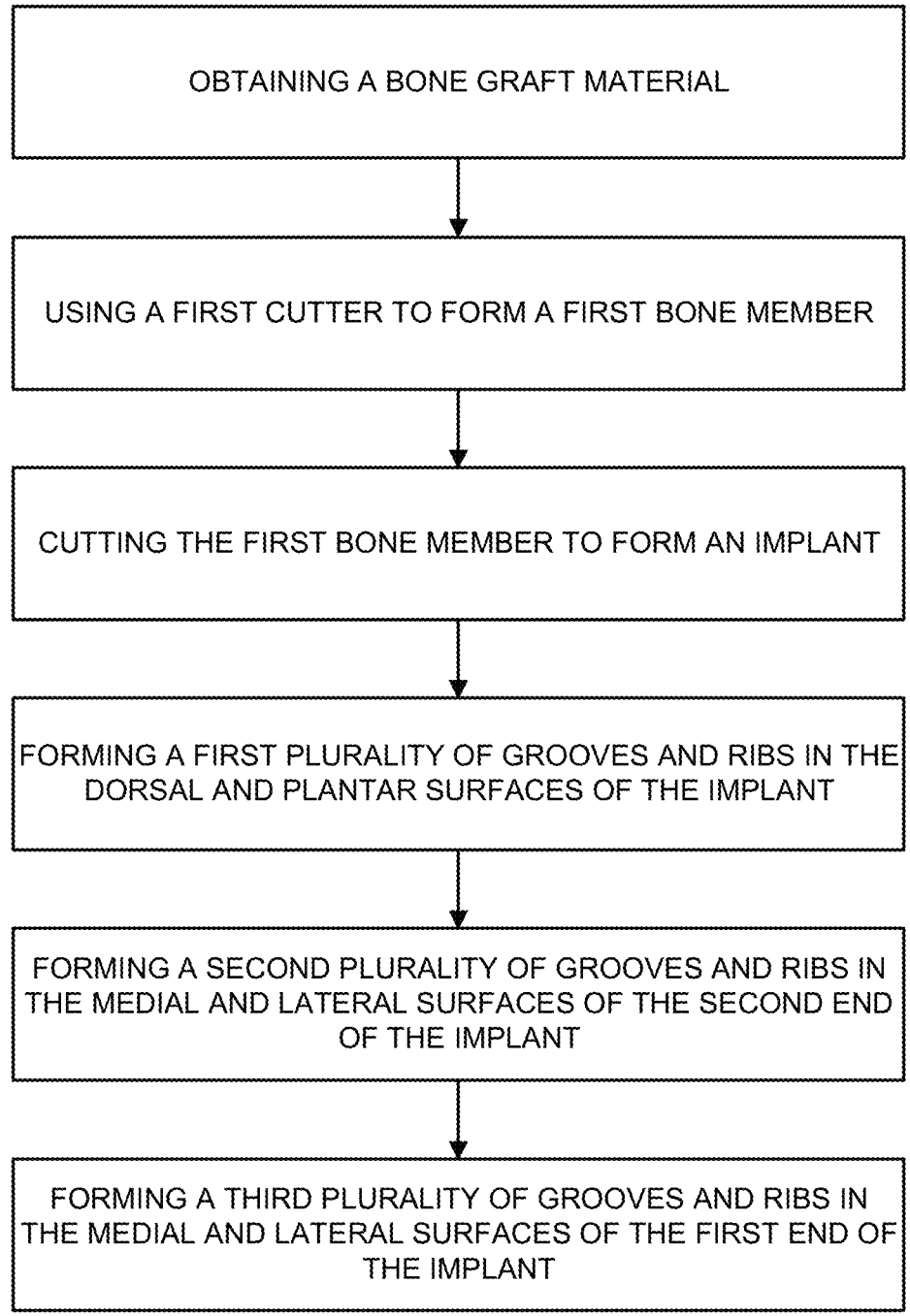
FIG. 65 depicts a method of forming the implant of FIG. 59, in accordance with an aspect of the present invention.

As shown in FIGS. 63 and 64, the implant 680 may include two cross-sectional shapes, when a cross-section is taken perpendicular to the longitudinal axis of the implant 680. The implant 680 may have a first cross-sectional shape, for example, the round shape of the exterior surface of the implant 680 formed by the ribs 644, 664, 684. The implant 680 may have a second cross-sectional shape when a cross-section is taken through at least one groove 642, 662, 682, for example, a square or rectangular shape. The square shape formed by the recessed grooves 642, 662, 682 provides a recessed surface in the implant 680 to assist with preventing rotation of the implant 680 in vivo. The recessed grooves 642, 662 in the implants 640, 660 may also provide a recessed surface in the implants 640, 660 to assist with preventing rotation of the implants 640, 660 in vivo.

A surgical method for correcting bone deformities using the instruments of FIGS. 1-30 and implants of FIGS. 31-64 is disclosed. The method includes, for example, performing a standard incision and soft tissue dissection over a joint, for example, a proximal interphalangeal joint. Next, the method may include exposing the head of the proximal phalanx. A saw, for example, a sagittal saw, may be used to resect the cartilage from the head of the proximal phalanx.

Figure 66:
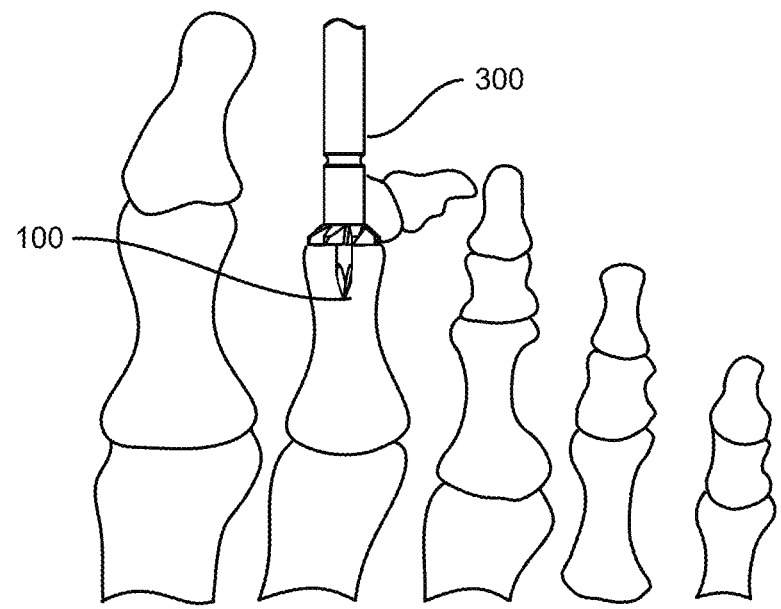
FIGS. 66-73 illustrate a first surgical method for inserting the implant of FIG. 59 into a patient's foot, in accordance with an aspect of the present invention.
Figure 67:
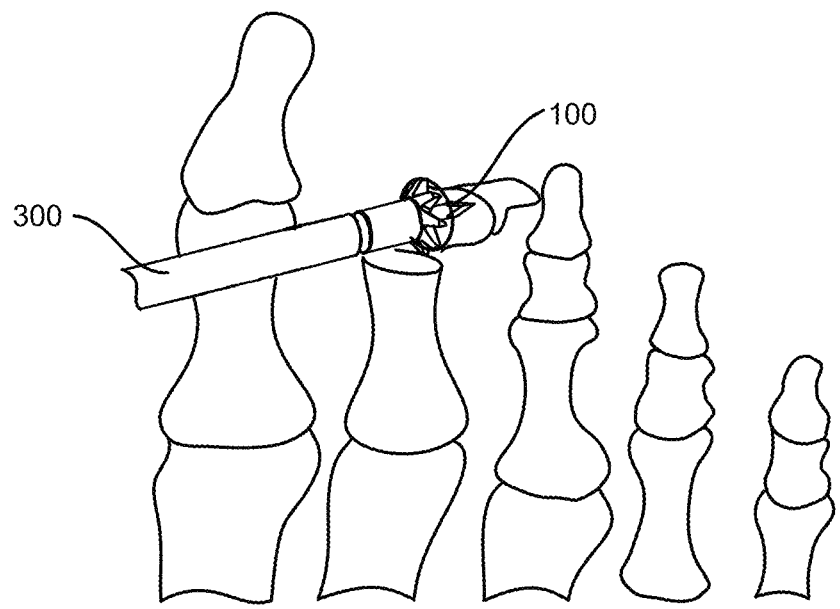

In one embodiment, the method may include using a trocar 100. This method may include inserting the trocar tip guide wire 100 into a reamer 300. The guide wire 100 may be inserted into the cannulated opening 308 in the reamer 300. The first end 102 of the guide wire 100 may protrude out of the distal end of the reamer 300 when the guide wire 100 is coupled to the reamer 300. In addition, the coupling member 110 of the guide wire 100 may engage the coupling member 320 of the reamer 300 to secure the guide wire 100 to the reamer 300. The trocar tip guide wire 100 and the reamer 300 may then be coupled to an instrument, such as a drill, for reaming the patient's bones. The first end 102 of the guide wire 100 may be centered on the base of, for example, the proximal phalanx. Next, the reamer 300 engages the proximal phalanx until satisfactory cartilage resection is achieved, as shown in FIG. 66. After reaming of the proximal phalanx is complete, the coupled reamer 300 and guide wire 100 are removed from the proximal phalanx. Then, the cartilage on the middle phalanx may be resected by inserting the guide wire 100 into the center of the middle phalanx. The reamer 300 may be turned on and may engage the middle phalanx until satisfactory cartilage resection is achieved, as shown in FIG. 67. Once the cartilage resection is complete, the coupled guide wire 100 and reamer 300 may be removed from the patient and the trocar tip guide wire 100 may be removed from the reamer 300.

Figure 68:
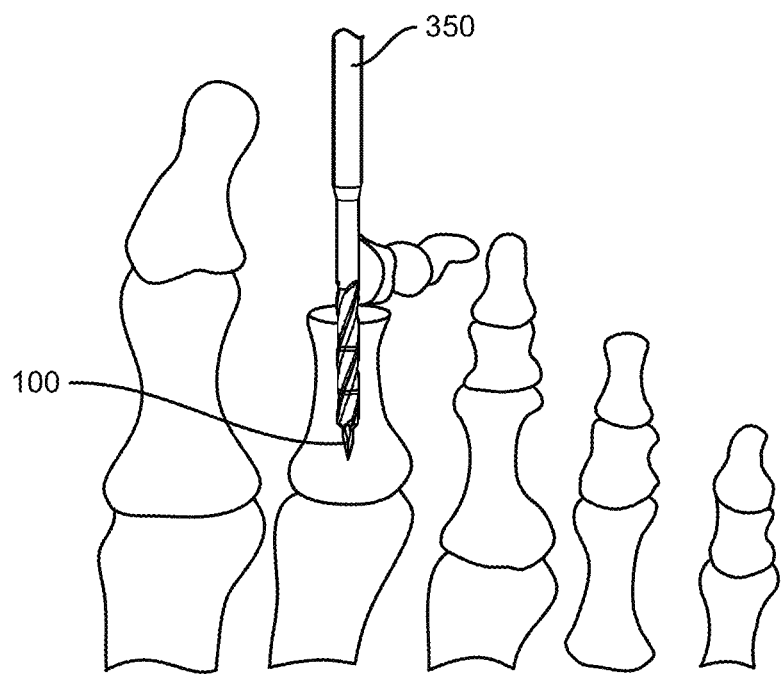
Figure 69:
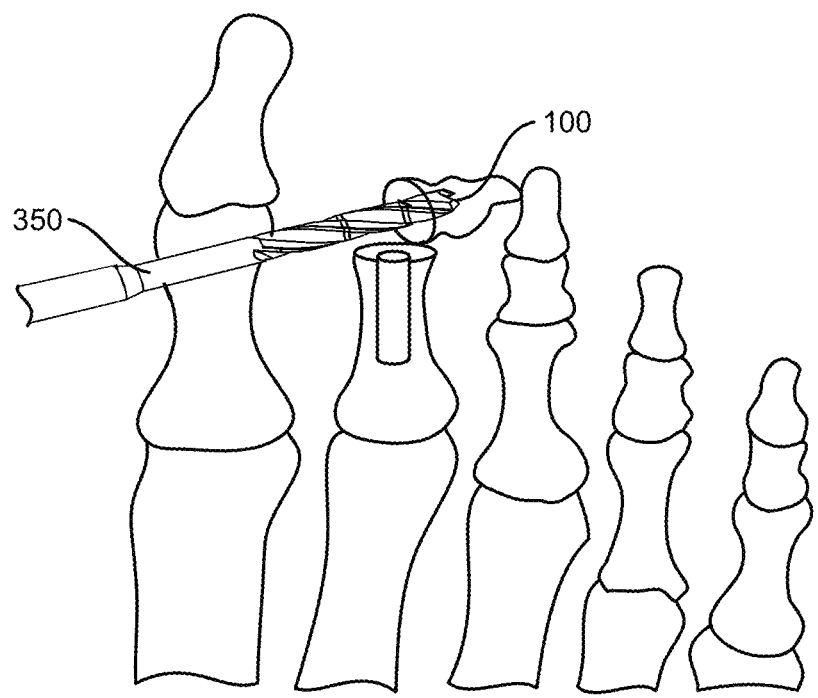
Figure 70:
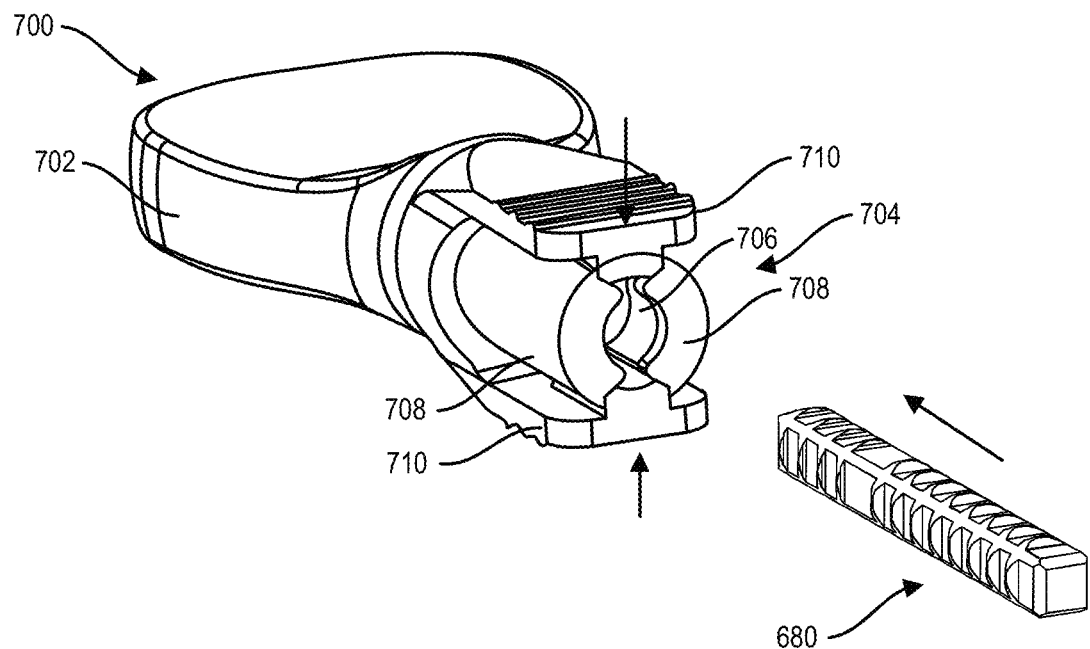
Figure 71:
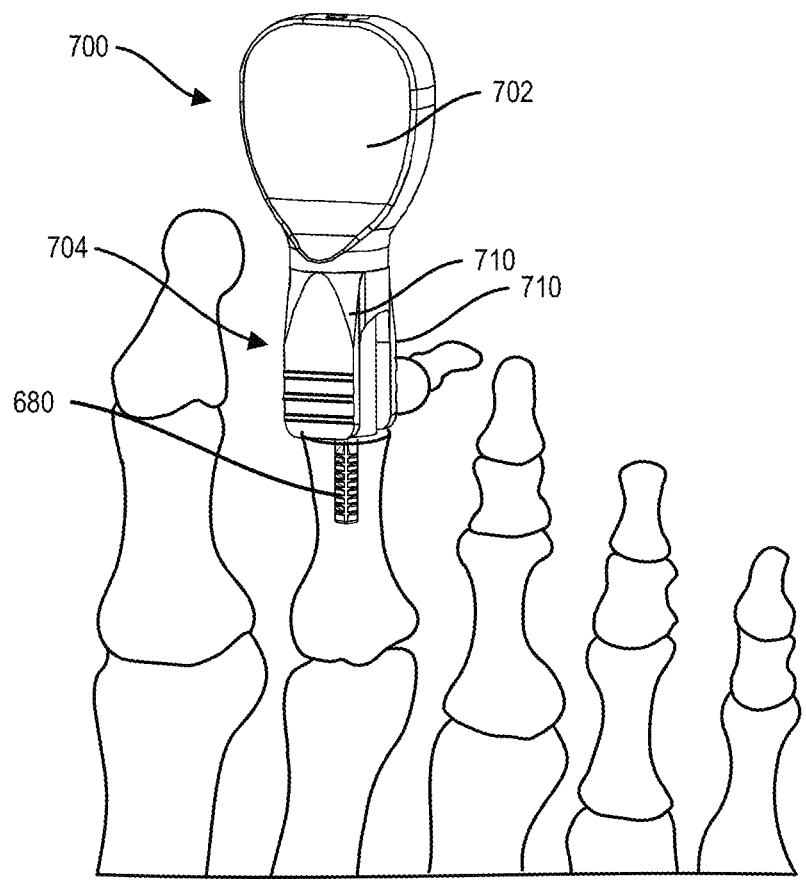
Figure 72:
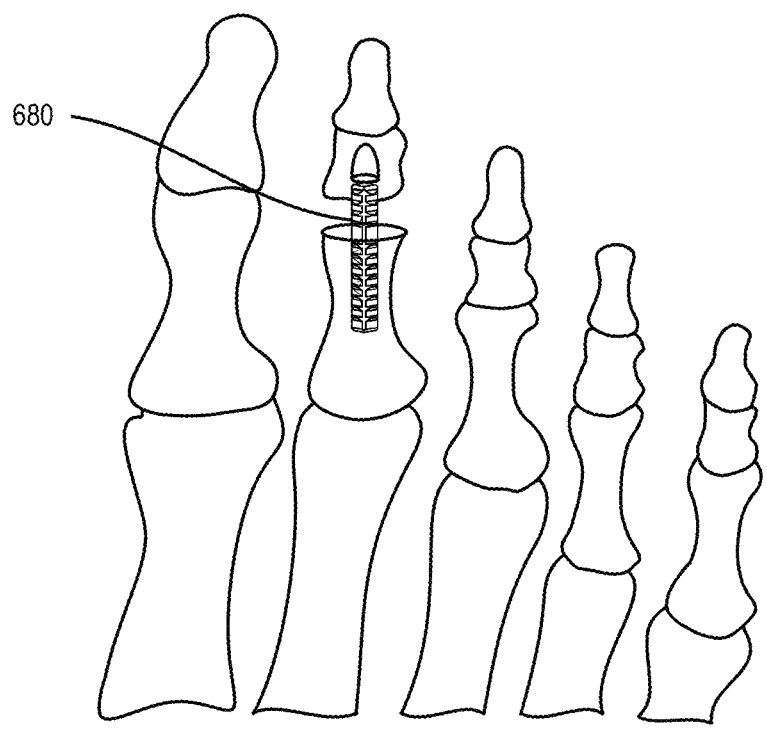
Figure 73:
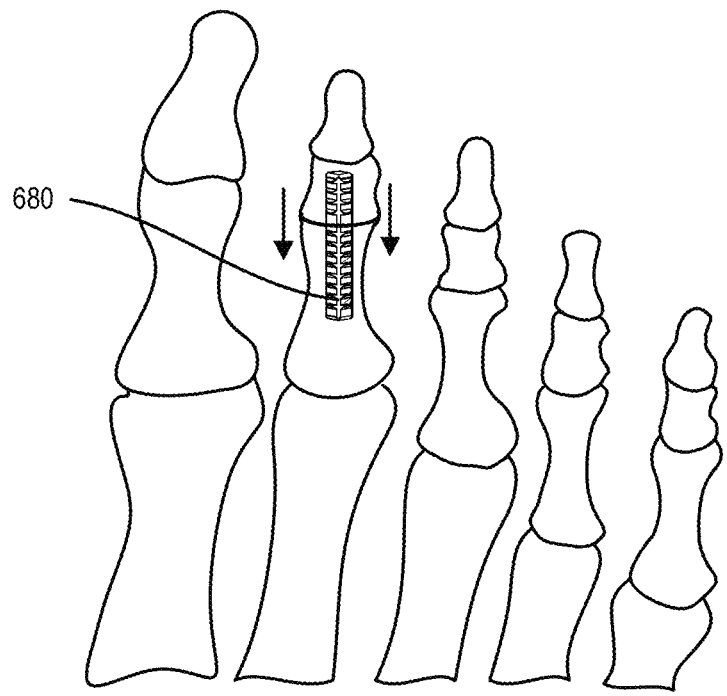

Next, the guide wire 100 may be inserted into a drill bit 350, 400. The drill bit 350, 400 and trocar tip guide wire insert 100 may then be coupled to a drill (not shown). The drill bit 350, 400 may be centered such that the trocar tip 102 is centered on the head of a bone, for example, the patient's proximal phalanx. The drill bit 350, 400 is then driven into the proximal phalanx until the second laser marking 368, 418 from the distal end of the drill bit 350, 400 is buried in the patient's bone, as shown in FIG. 68. The smaller drill bit 350 should be used first and if necessary the larger drill bit 400 may be used. After drilling is complete, the drill bit 350, 400 and trocar 100 are removed from the proximal phalanx. Then, the trocar tip guide wire insert 100 and coupled drill bit 350, 400 may be centered over the base of the middle phalanx. The trocar 100 and drill bit 350, 400 may then be driven into the middle phalanx until the first laser mark 368, 418 from the distal end is buried, as shown in FIG. 69. The drill (not shown), drill bit 350, 400 and trocar tip guide wire 100 may then be removed from the middle phalanx and the patient. Next, an implant 680 may be inserted into the proximal phalanx, as shown in FIG. 72. Optionally, an insertion instrument, such as insertion instrument 700, as shown in FIGS. 70 and 71, may be used to insert the implant 680 into the proximal phalanx. Alternatively, an insertion instrument 800, 820, as described in greater detail below and shown in FIGS. 83-91, 96, 97, 102, 103, 110 and 111, may be used. The insertion instrument 700 may include a body 702 and a coupling member 704 extending away from the body 702. The coupling member 704 may include an opening 706 and side members 708 positioned adjacent to the opening 706. In addition, the coupling member 704 may include movable tabs 710 positioned adjacent to the opening 706 and the movable tabs 710 engage the side members 708. The movable tabs 710 may be depressed to expand the opening 706 and the implant 680 may be inserted into the opening 706. The movable tabs 710 may then be released to engage the implant 680. As shown in FIG. 71, the implant 680 coupled to the inserter 700 may then be inserted into the proximal phalanx and the tabs 702 may be depressed to release the implant 680. Next, the middle phalanx is pulled distally and pushed proximally to clear the implant 680 and allow the implant 680 to seat within the middle phalanx, as shown in FIGS. 72 and 73. Finally, the soft tissue and incision may be closed.

When a trocar technique is used, the implant 680 may be removed by obtaining a saw, for example, a sagittal saw, and cutting the hammertoe implant 680 at the proximal interphalangeal joint. Next, the trocar tip guide wire insert 100 may be placed within an appropriately sized trephine 250. The coupling member 110 of the guide wire insert 100 may engage the coupling member 270 of the trephine 250 to secure the guide wire insert 100 and the trephine 250 together. The coupled trephine 250 and trocar tip guide wire insert 100 may be placed over the implant 680 in the proximal phalanx. The trocar tip 100 may then be placed down the cannula of the proximal phalanx portion of the implant 680. The trephine 250 may then be used until the appropriate depth along the outside of the implant 680 is reached to extract the implant 680 from the proximal phalanx. Once the drilling is complete, the implant 680, trephine 250, and trocar 100 may be removed from the proximal phalanx.

Next, the coupled trocar tip 100 and trephine 250 may be placed down the cannula of the middle phalanx portion of the implant 680. The trephine 250 may then be inserted until the appropriate depth along the outside of the implant 680 is reached to extract the implant 680 from the middle phalanx. Finally, the trephine 250, trocar tip 100, and implant 680 may be removed from the middle phalanx and from the patient. Finally, the soft tissue and incision may be closed.

The method of insertion and removal of the hammertoe implant 680 may also be performed using the second trocar guide wire 150 and a reamer, drill bit, and trephine each with a proximal end that includes the instrument connector end 200.

Figure 74:
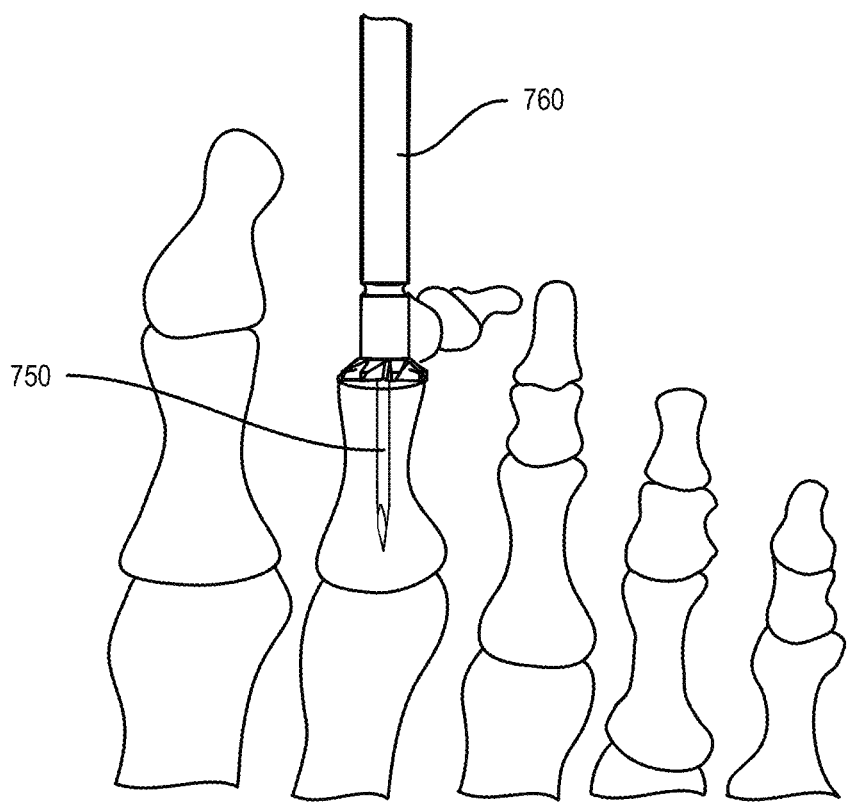
FIGS. 74-80 illustrate a second surgical method for inserting the implant of FIG. 59 into a patient's foot, in accordance with an aspect of the present invention.
Figure 75:
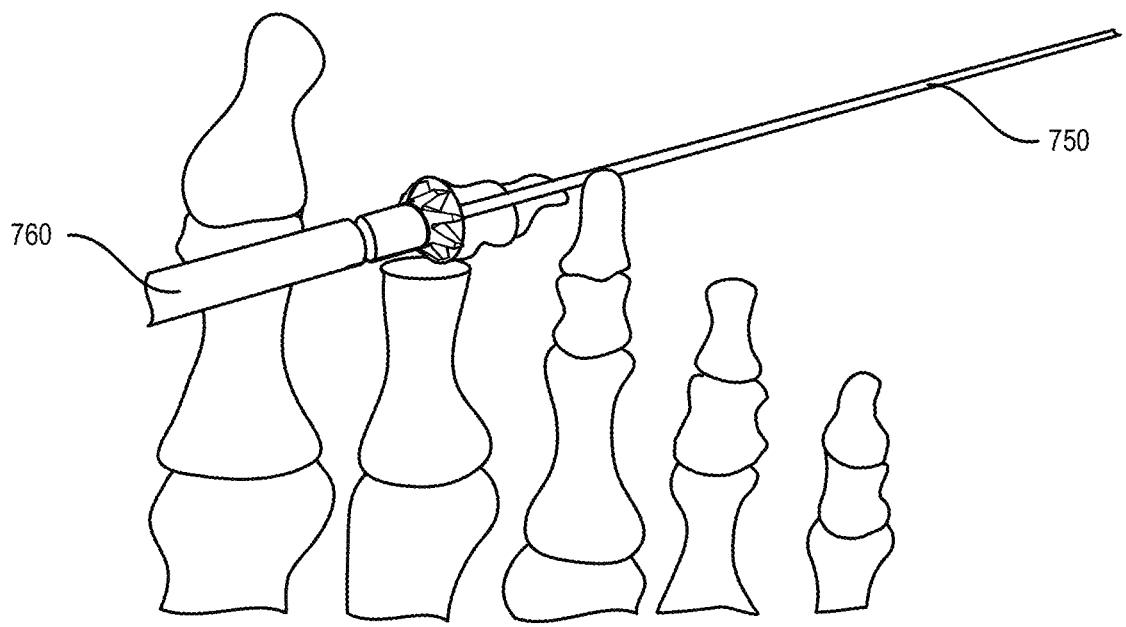

Alternatively, the method may include using a retrograde k-wire technique. The method may include inserting a k-wire 750 centrally into the proximal phalanx. Next, a planer or reamer 760 with a first end the same or similar to the first end 304 of the reamer 300 may be slid over the k-wire 750 and used to removal all of the cartilage from the end of the proximal phalanx, as shown in FIG. 74. Once all of the cartilage is removed, the reamer 760 may be removed from the k-wire 750 and the k-wire 750 may be removed from the proximal phalanx. Next, the k-wire 750 may be inserted into the middle phalanx, exiting the distal phalanx centrally plantar to the nail, as shown in FIG. 75. Then, the k-wire 750 is inserted into the central medullary canal of the proximal phalanx in a retrograde fashion and fluoroscopy is used to determine the k-wire 750 and toe position. Once an optimal position of the k-wire 750 is determined, the k-wire 750 is pulled distally so that only a portion of the wire, for example, approximately 2-3 mm, protrudes from the base of the middle phalanx. The planer 760 may then be placed over the k-wire 750 and the proximal end of the middle phalanx may be reamed to remove all cartilage, as shown in FIG. 75. After all the cartilage is removed, the reamer 760 may be removed from the k-wire 750.

Figure 76:
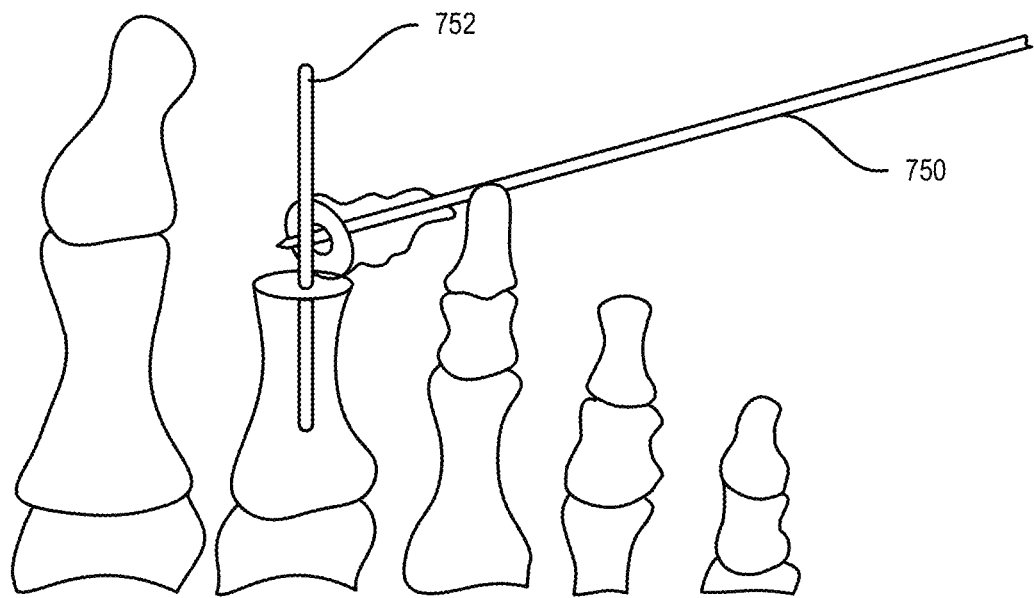
Figure 77:
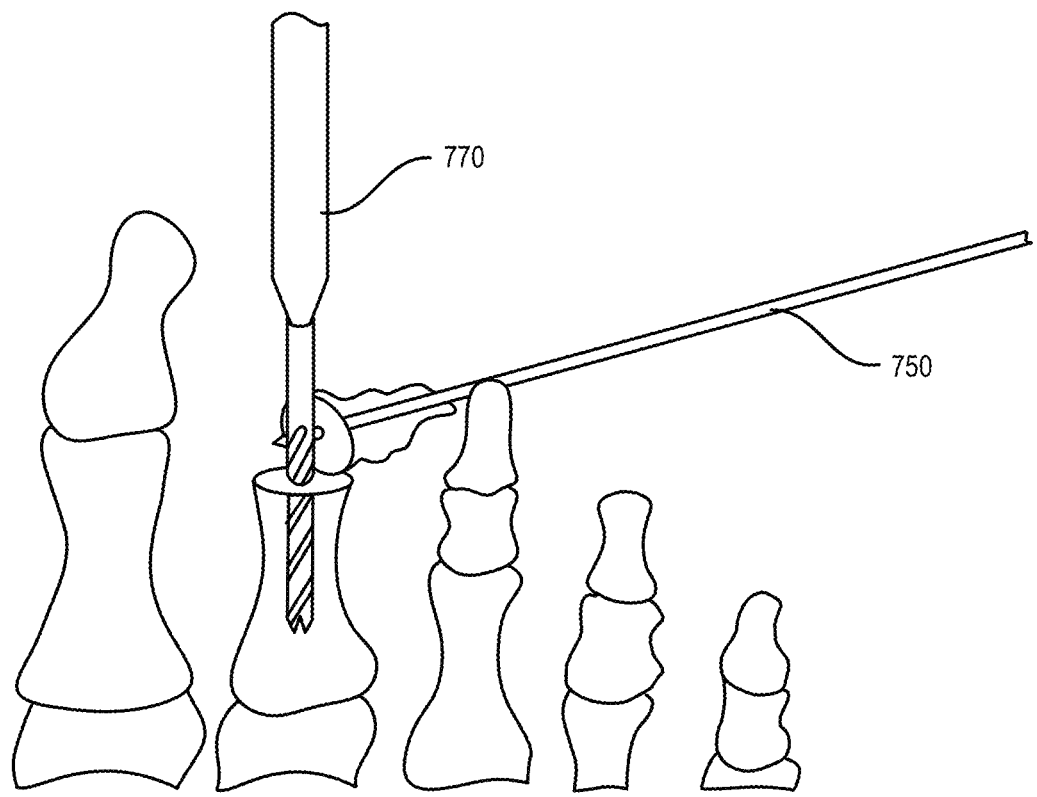
Figure 78:
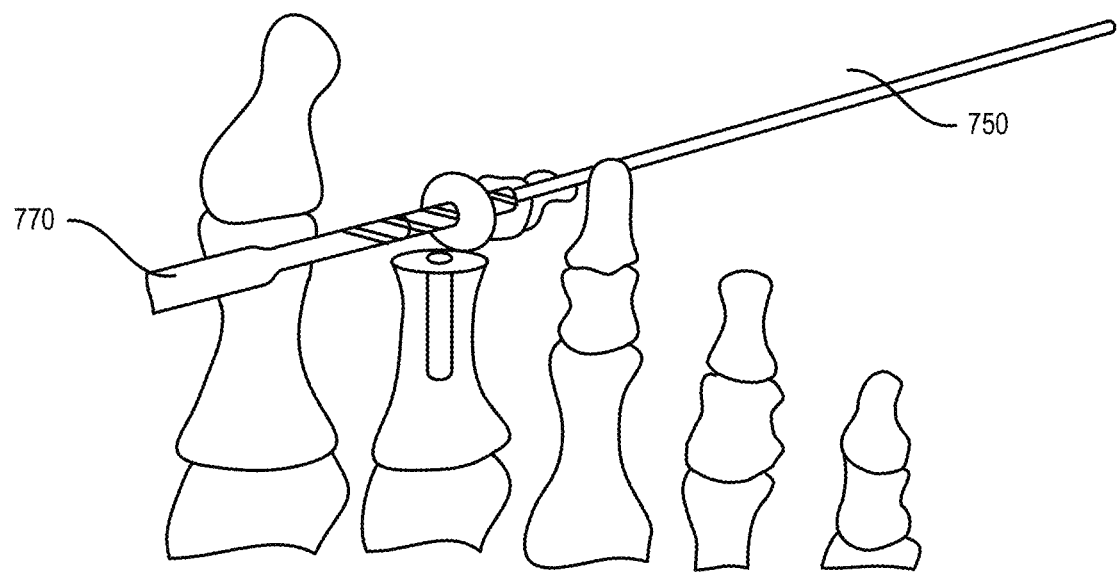

Next, a blunt k-wire 752 may be inserted into the canal of the proximal phalanx, as shown in FIG. 76. A drill and drill bit 770 may then be selected and inserted over the blunt k-wire 752 to drill the canal down to the second laser marking on the drill bit 770, as shown in FIG. 77. The drill bit 770 and blunt k-wire 752 may then be removed from the proximal phalanx and the drill may then be used to drill over the k-wire 750 and into the middle phalanx, as shown in FIG. 78. The middle phalanx may be drilled to the first marking on the drill bit 770. The drill bit 770 and k-wire 750 may then be removed from the middle phalanx.

Figure 79:
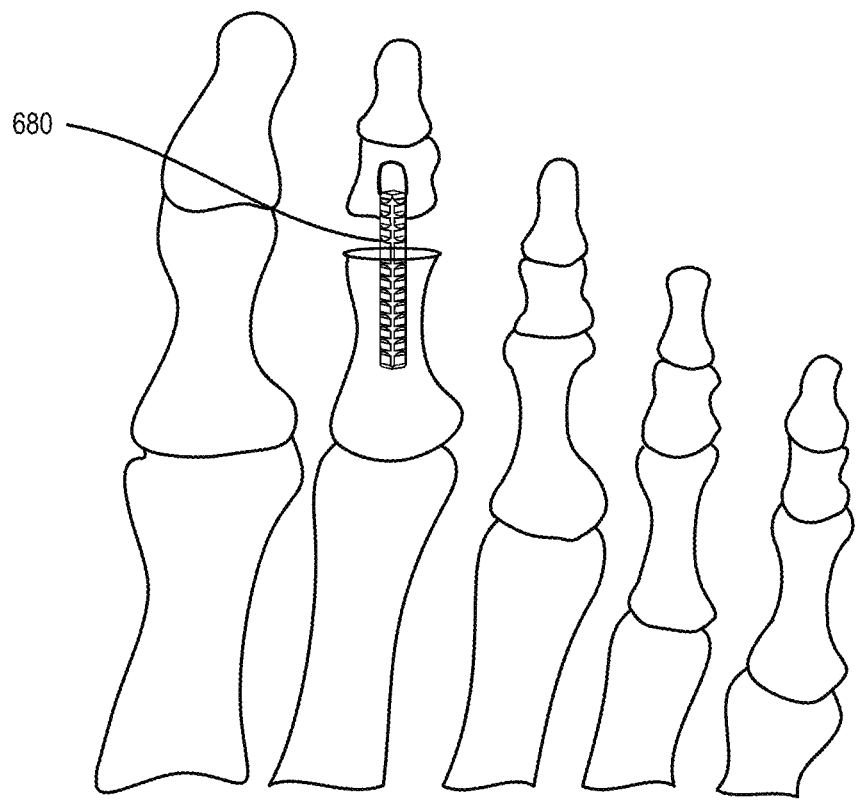
Figure 80:
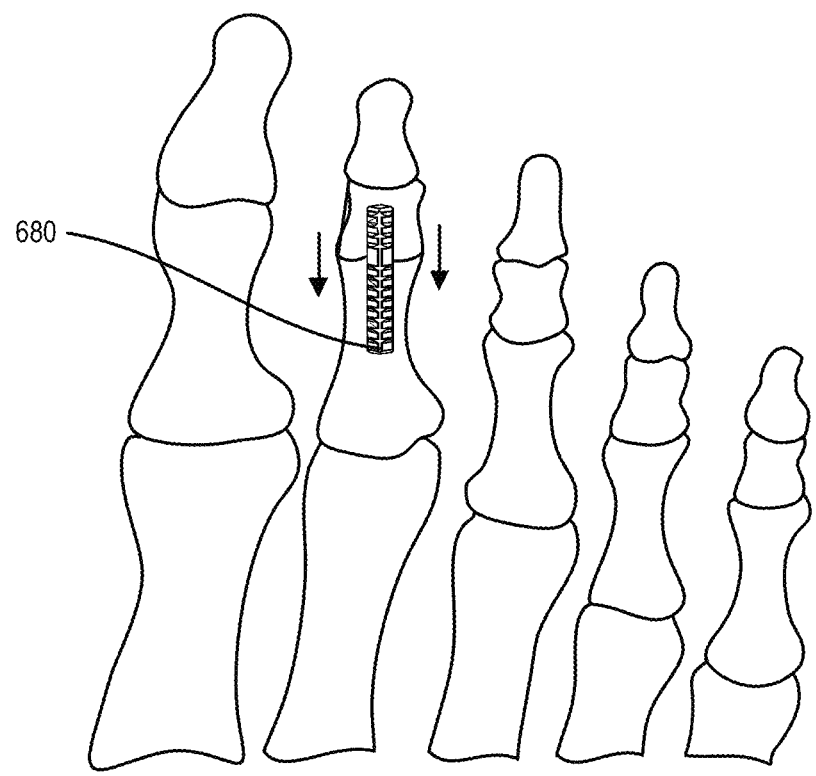
Figure 81:
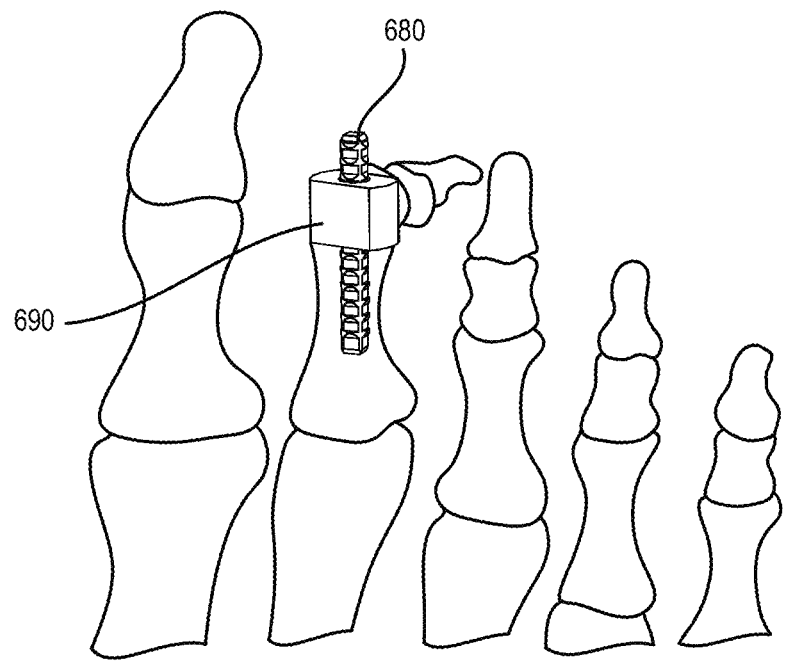
FIGS. 81-82 illustrate the first and second surgical methods for inserting the implant of FIG. 59 and a spacer into a patient's foot, in accordance with an aspect of the present invention.

Then, the implant 680 may be inserted into the patient's foot. For example, an inserter may be coupled to the implant 680, as shown in FIG. 79, and described in greater detail above. After, the implant 680 is coupled to the inserter, the implant 680 may be inserted into the opening drilled into the proximal phalanx. The implant 680 may be inserted until the inserter contacts the distal surface of the proximal phalanx, as shown in FIG. 79. Once the implant 680 is fully inserted into the proximal phalanx, the inserter may be removed from the implant as described in greater detail above. Next, the distal portion of the toe is distracted distally and translated dorsally to allow the protruding distal portion of the implant 680 to seat within the drill opening in the middle phalanx, as shown in FIG. 80. After seating the implant 680, pressure may be applied proximally to the distal aspect of the toe until apposition of the proximal and middle phalanges is achieved, as shown in FIG. 81. Finally, the soft tissue and incision may be closed.

When a retrograde k-wire technique is used, the implant 680 may be removed by first using a saw, for example, a sagittal saw, to cut the hammertoe implant 680 at the proximal interphalangeal joint. Then, a k-wire 100 may be inserted into the cannulation of the trephine 250. After the k-wire 100 is inserted, the trephine 250 may be attached to an instrument and the coupled k-wire 100 and trephine 250 may be inserted into the proximal phalanx portion of the implant 680. The trephine 250 may then be used until a desired depth along the outside of the implant 680 is reached in order to extract the implant 680 from the proximal phalanx. Once cutting with the trephine 250 is complete, the patient's bone, the implant 680 and k-wire 100 may be removed from the proximal phalanx.

Next, the coupled k-wire 100 and trephine 250 may be inserted into the middle phalanx. The trephine 250 is then inserted until the desired depth along the outside of the implant 680 is reached to extract the implant 680 from the middle phalanx. Once cutting with the trephine 250 is complete, the patient's bone, the implant 680 and k-wire 100 may be removed from the middle phalanx. Finally, the soft tissue and incision may be closed.

Figure 82:
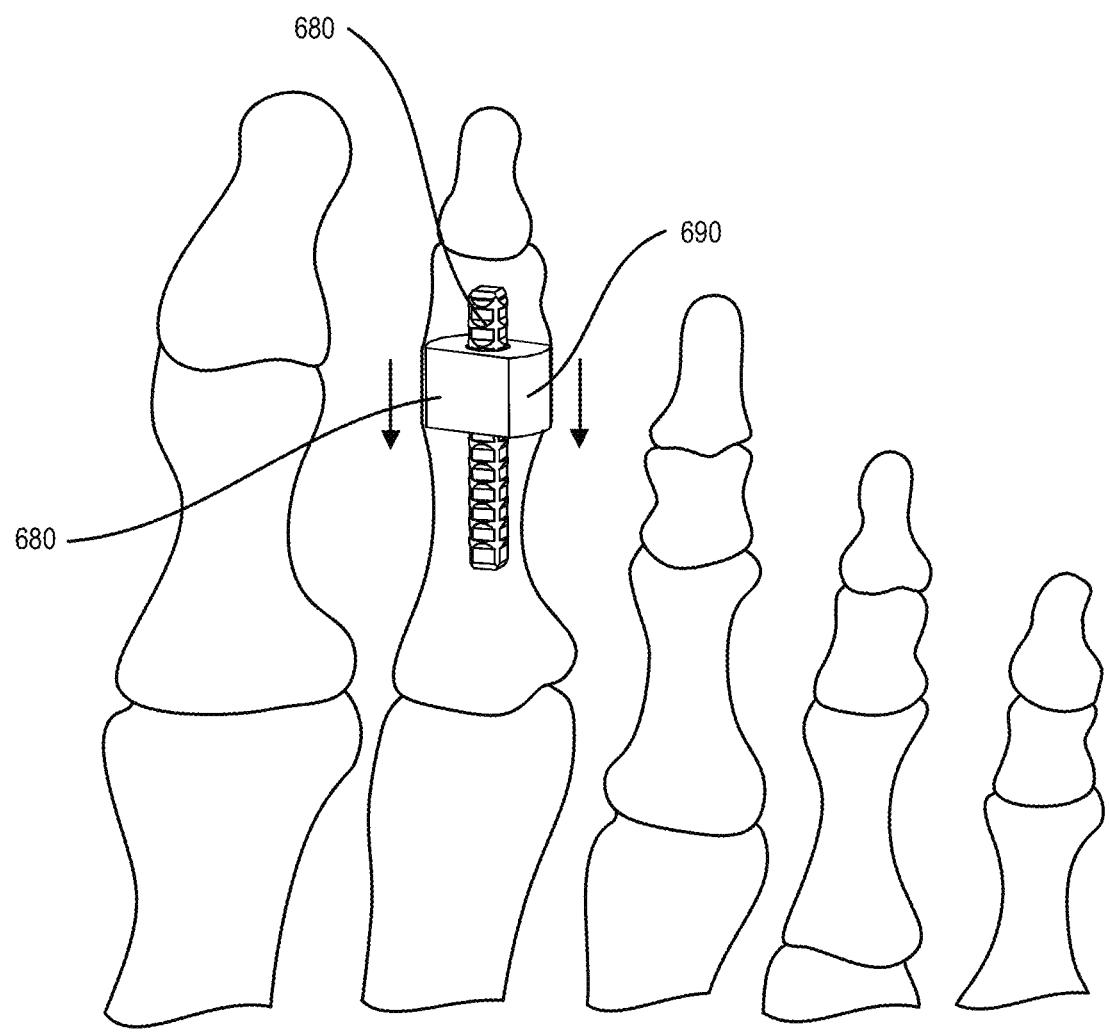
Figure 83:
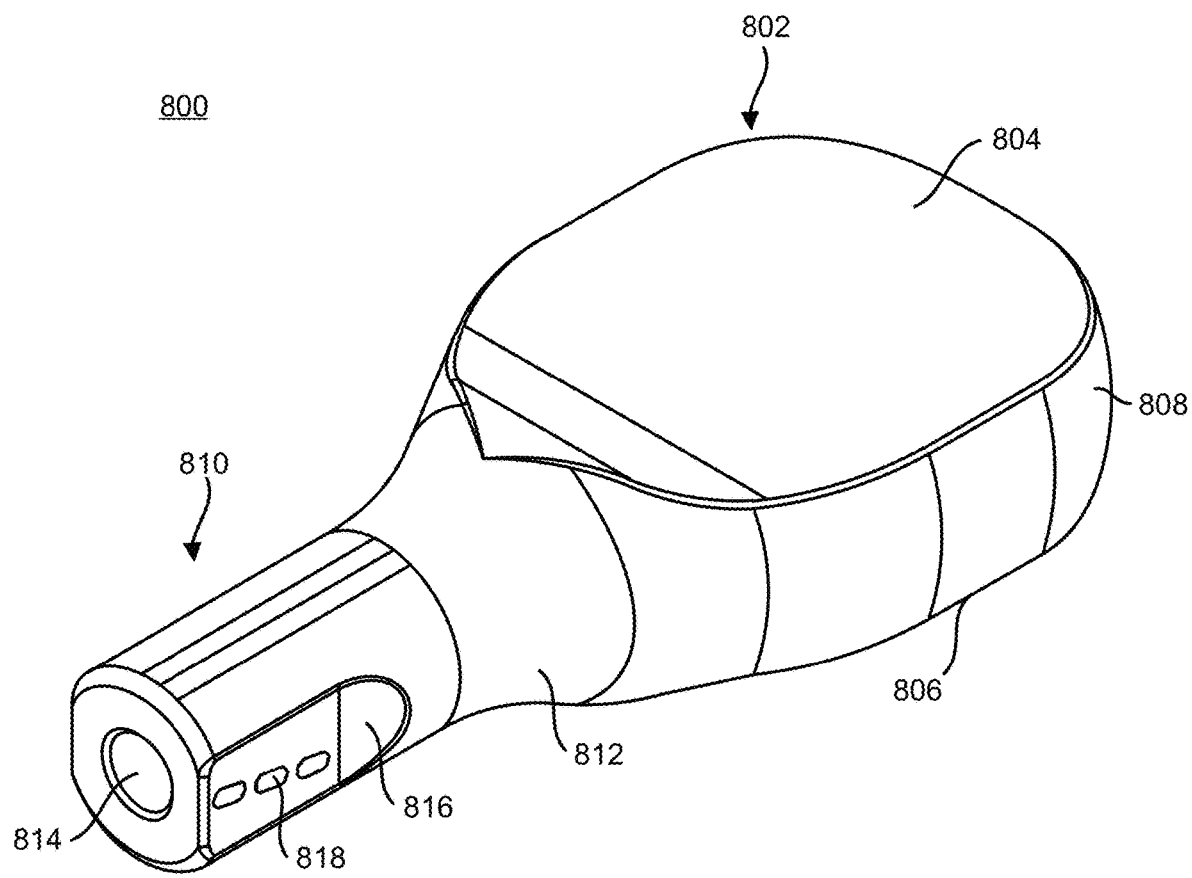
FIG. 83 is a first perspective view of an insertion instrument, in accordance with an aspect of the present invention.
Figure 84:
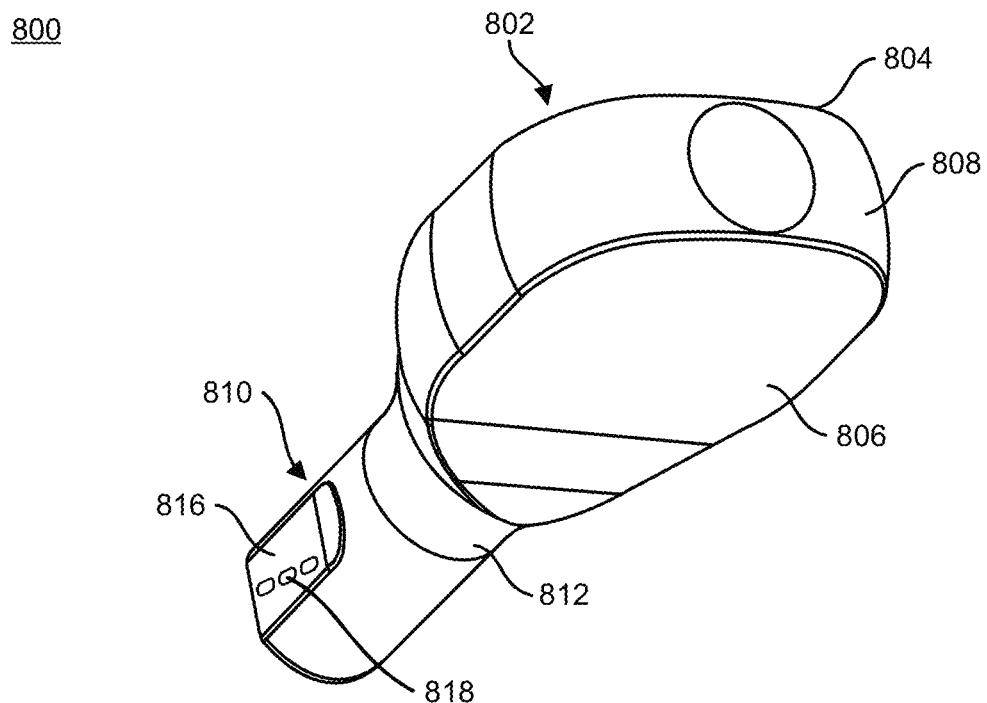
FIG. 84 is a second perspective view of the insertion instrument of FIG. 83, in accordance with an aspect of the present invention.
Figure 85:
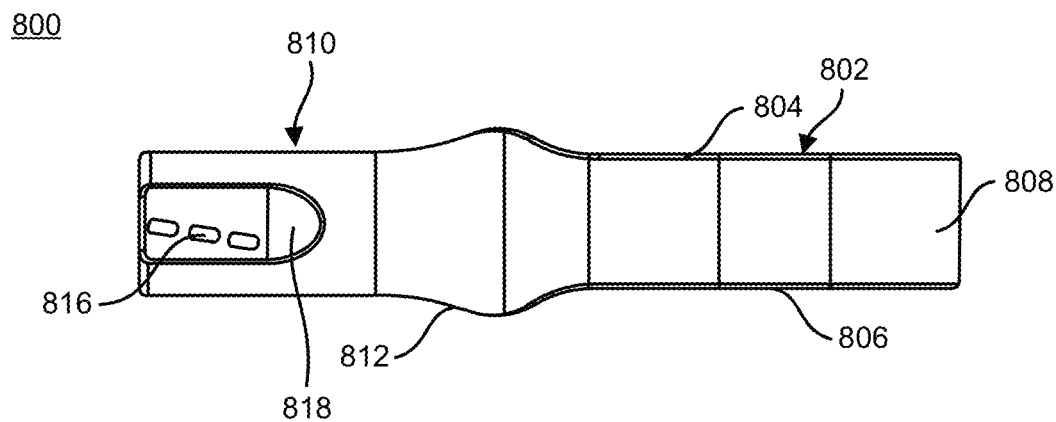
FIG. 85 is a side view of the insertion instrument of FIG. 83, in accordance with an aspect of the present invention.
Figure 86:
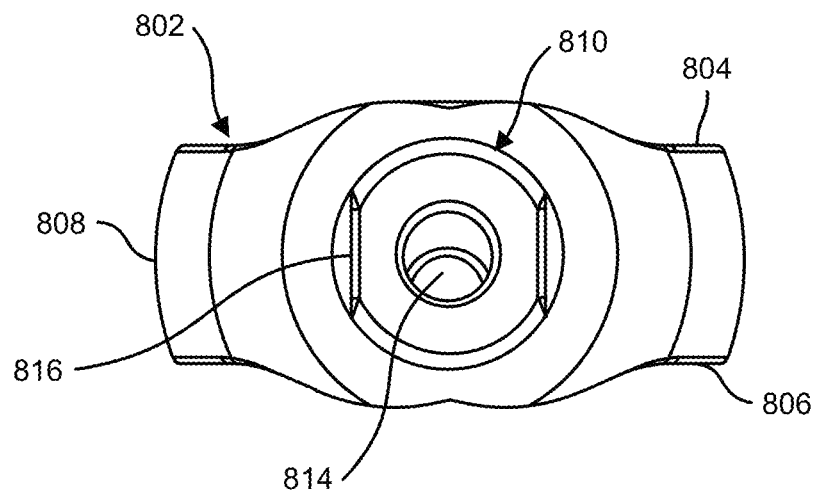
FIG. 86 is a first end view of the insertion instrument of FIG. 83, in accordance with an aspect of the present invention.
Figure 87:
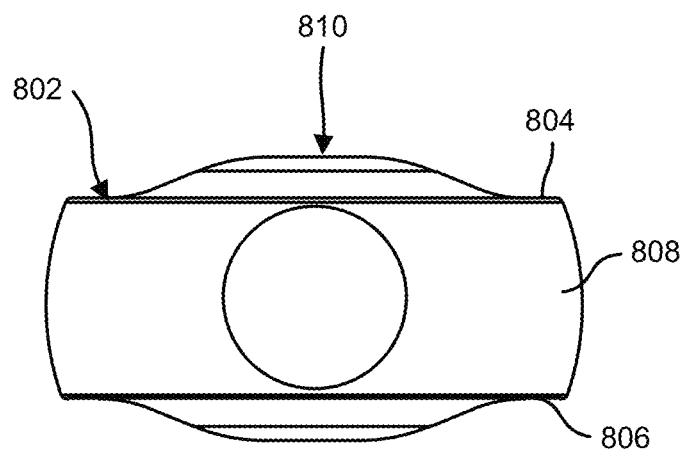
FIG. 87 is a second end view of the insertion instrument of FIG. 83, in accordance with an aspect of the present invention.
Figure 88:
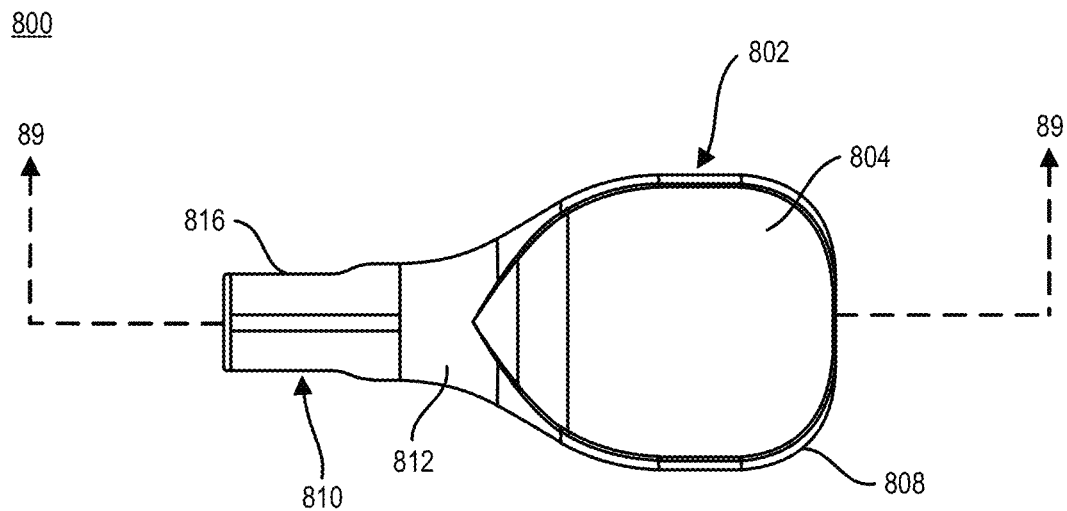
FIG. 88 is a top view of the insertion instrument of FIG. 83, in accordance with an aspect of the present invention.
Figure 89:
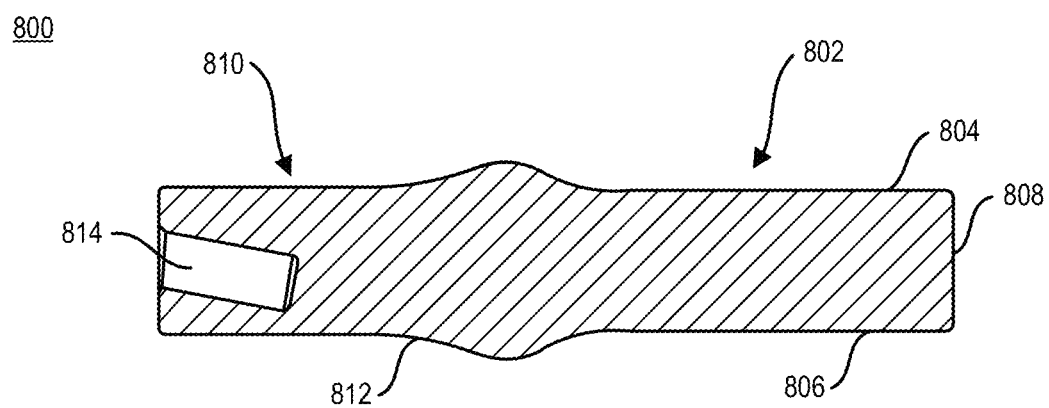
FIG. 89 is a cross-sectional view of the insertion instrument of FIG. 83 taken along line 89-89 of FIG. 88, in accordance with an aspect of the present invention.
Figure 90:
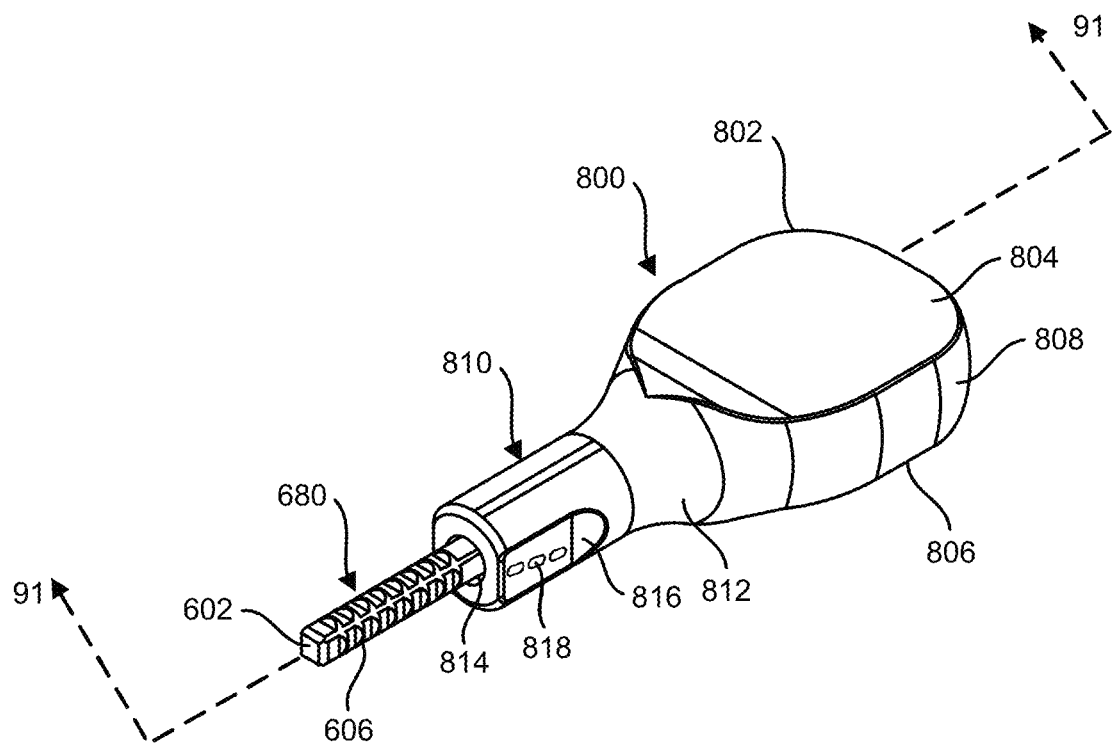
FIG. 90 is a perspective view of the implant of FIG. 59 inserted into the insertion instrument of FIG. 83, in accordance with an aspect of the present invention.

As shown in FIGS. 82 and 83, a bone spacer 690, for example, a cancellous spacer, may be used with the implant 680 if overshortening of the phalanges is encountered during a hammertoe procedure. The spacer 690 allows for restoration of the length of the toe. The spacers 690 may be available in multiple sizes, for example, 6 mm, 8 mm and 10 mm although other sizes are also contemplated ranging from 2 mm to 12 mm. The spacer 690 may include an opening generally centered in the spacer 690 for receiving the implant 680. The spacer 690 should be positioned over the midpoint of the implant 680.

Figure 91:
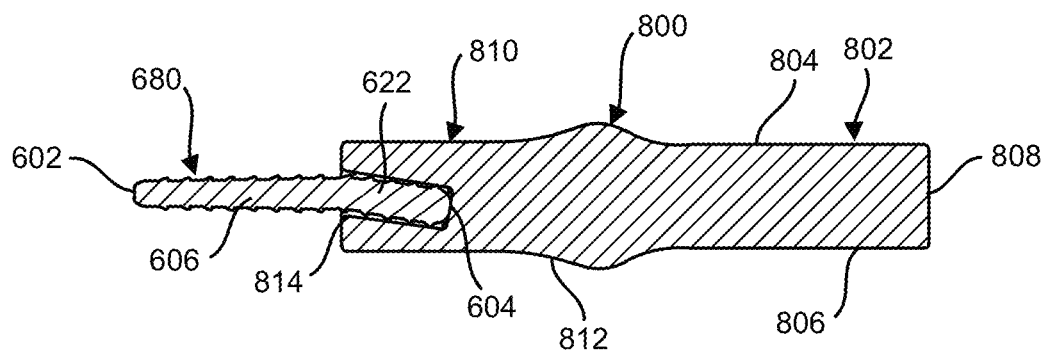
FIG. 91 is a cross-sectional view of the implant of FIG. 59 inserted into the insertion instrument of FIG. 83 taken along line 91-91 in FIG. 90, in accordance with an aspect of the present invention.

Referring now to FIGS. 83-91, another insertion instrument 800 is shown. The insertion instrument 800 includes a body or handle portion 802 and a coupling member 810 extending away from a second end of the body or handle portion 802. The handle portion 802 may include a top surface 804, a bottom surface 806, and a side portion 808 extending between the top surface 804 and the bottom surface 806. The handle portion 802 may have a first width and the coupling member 810 may have a second width. The first width may be larger than the second width. The insertion instrument 800 may include a tapered portion 812 extending between the handle portion 802 and the coupling member 810. The coupling member 810 may include an opening 814 extending from a second end of the insertion instrument 800 into the coupling member 810 toward a first end of the insertion instrument 800. The coupling member 810 may also include, for example, planar sections 816 on the sides of the coupling member 810. The planar sections 816 may include alignment markings 818 showing the position or angulation of the opening 814. The angulation of the opening 814 may correspond to the position or angulation of the first body portion 606 relative to the second body portion 622, as shown in FIG. 91 to ensure implant 680 projects straight away from the insertion instrument 800.

Figure 92:
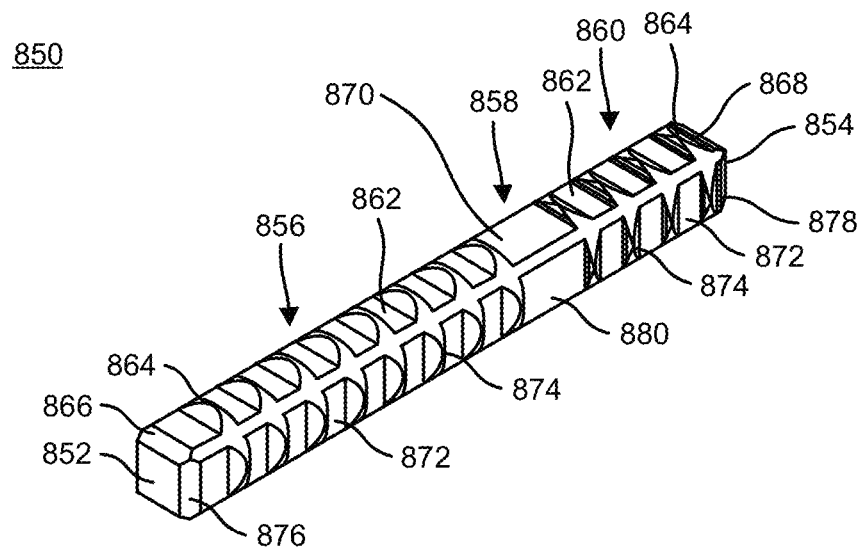
FIG. 92 is a perspective view of another implant, in accordance with an aspect of the present invention.
Figure 93:
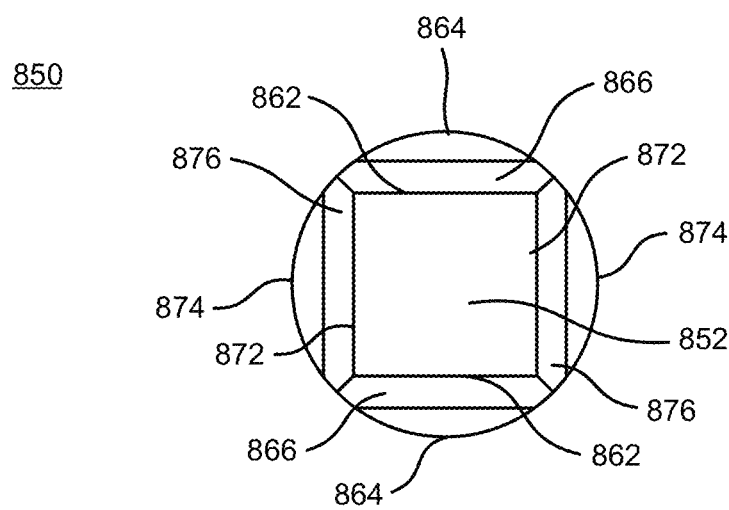
FIG. 93 is an end view of the implant of FIG. 92, in accordance with an aspect of the present invention.
Figure 94:
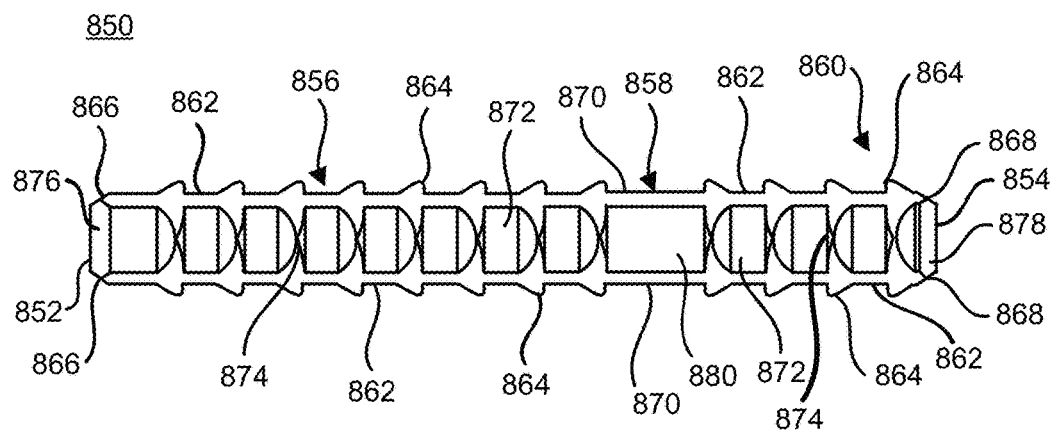
FIG. 94 is a first side view of the implant of FIG. 92, in accordance with an aspect of the present invention.
Figure 95:
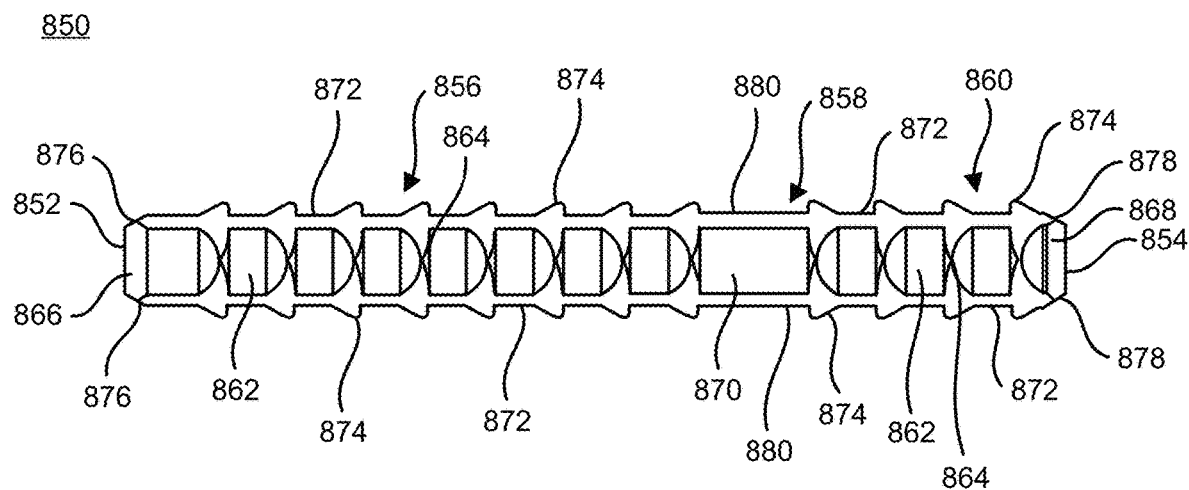
FIG. 95 is a second side view of the implant of FIG. 92, in accordance with an aspect of the present invention.

Referring now to FIGS. 92-97, another implant 850 is shown. The implant 850 includes a first end 852 and a second end 854. The implant 850 may also include a first body portion 856 extending from the first end 852 toward the second end 854 and a second body portion 860 extending from the second end 854 toward the first end 852. The implant 850 may also include a central or coupling portion 858 positioned where the first body portion 856 engages the second body portion 860. As shown in FIGS. 92-97, the central portion 858 may be aligned with the first body portion 856 and second body portion 860 to form a straight implant 850. The implant 850 may include, for example, a plurality of first grooves, recesses, teeth, or ridges 862 recessed into the dorsal and plantar surfaces of the implant 850. The first recesses 862 may form first ribs or projections 864 positioned between adjacent recesses 862 and the first ribs 864 may extend out from the dorsal and plantar surface of the implant 850, as shown in FIG. 94. The ribs 864 may be positioned, for example, approximately 1 mm to 2 mm from the adjacent ribs 864, more specifically, the ribs 864 may be spaced 1.5 mm apart. The recesses 862 and ribs 864 may be formed in the implant 850 using, for example, a broaching press having a plate with cutting edges to correspond to the recesses 862 and ribs 864. The implant 850 may also include tapered or angled edges 866 at the first end 852 and tapered or angled edges 868 at the second end 854, as shown in FIGS. 92, 94 and 95. The tapered edges 866, 868 may be on the dorsal and plantar surfaces of the implant 850. The central portion 858 may include recesses 870 inset into the dorsal and plantar surfaces of the implant 850. The recesses 870 may be, for example, longer than the recesses 862.

The implant 850 may also include a plurality of second grooves, recesses, teeth or ridges 872 recessed into the medial and lateral surfaces of the implant 850. The second recesses 872 may form second ribs or projections 874 positioned between adjacent recesses 872 and the second ribs 874 may extend out from the medial and lateral surfaces of the implant 850, as shown in FIG. 95. The ribs 874 may be positioned, for example, approximately 1 mm to 2 mm from the adjacent ribs 874, more specifically, the ribs 874 may be spaced 1.5 mm apart. The second recesses 872 and ribs 874 may be formed in the implant 850 using, for example, a broaching press having a plate with cutting edges to correspond to the recesses 872 and ribs 874. The implant 850 may also include tapered or angled edges 876 at the first end 852 and tapered or angled edges 878 at the second end 854, as shown in FIGS. 92, 94 and 95. The tapered edges 876, 878 may be on the medial and lateral surfaces of the implant 850. The central portion 858 may include recesses 880 inset into the medial and lateral surfaces of the implant 850. The recesses 880 may be, for example, longer than the recesses 862.

Figure 96:
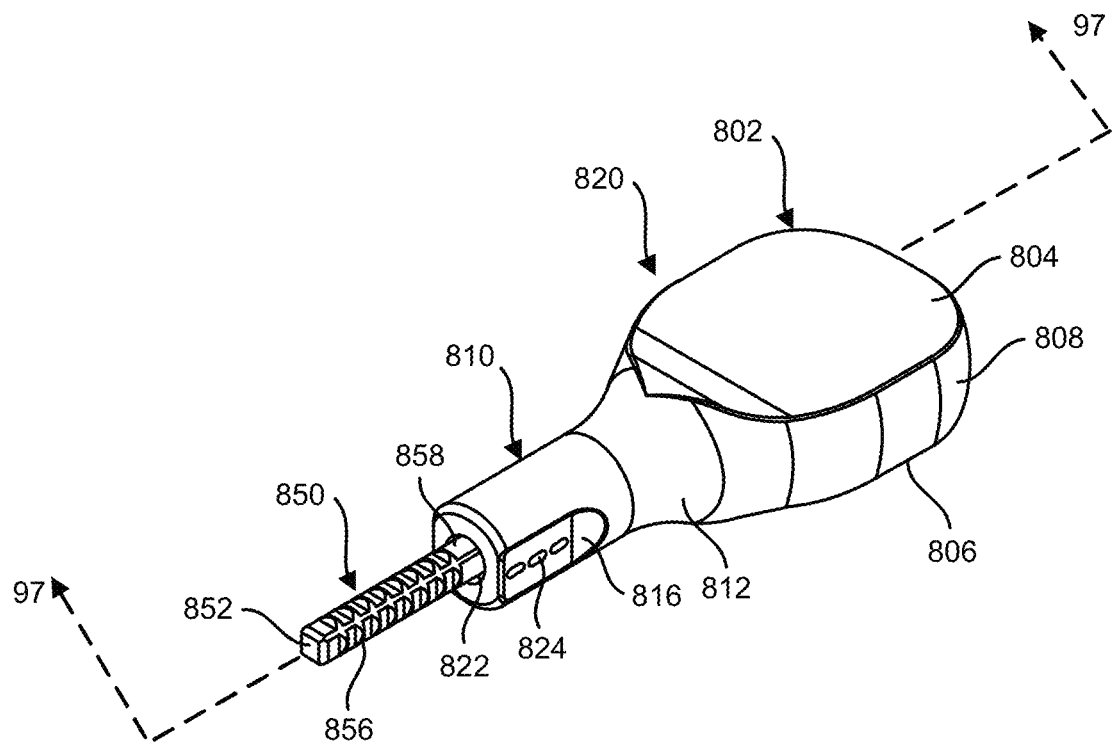
FIG. 96 is a perspective view of the implant of FIG. 92 inserted into another embodiment of an insertion instrument, in accordance with an aspect of the present invention.
Figure 97:
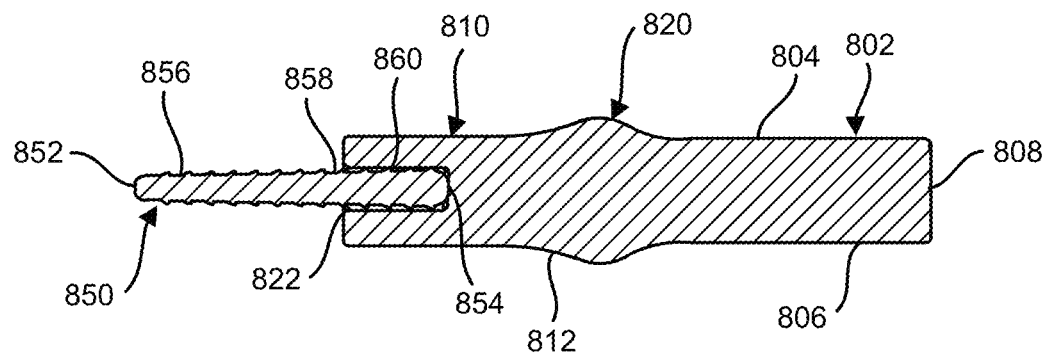
FIG. 97 is a cross-sectional view of the assembled implant and insertion instrument of FIG. 96 taken along line 97-97, in accordance with an aspect of the present invention.

Referring now to FIGS. 96-97, the implant 850 and the corresponding insertion instrument 820 are shown. The insertion instrument 820 may be similar to the insertion instrument 800, as described in greater detail above, which will not be described again here for brevity sake. The insertion instrument 820 includes a body or handle portion 802, a top surface 804, a bottom surface 806, a side portion 808, a coupling member 810, a tapered portion 812, planar sections 816, an opening 822 and alignment markings 824. The alignment markings 824 show the position or angulation of the opening 822. The angulation of the opening 822 may correspond to the position or angulation of the second body portion 860, as shown in FIG. 97.

Figure 98:
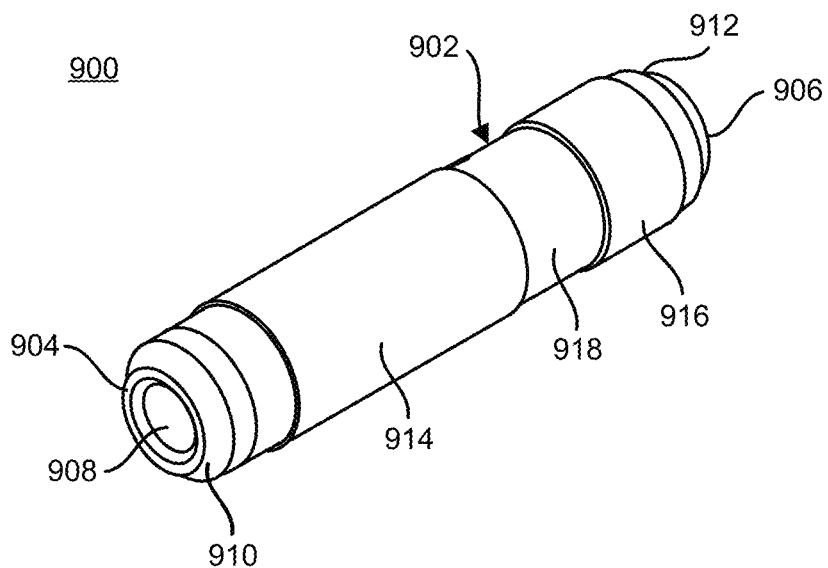
FIG. 98 is a first perspective view of another implant, in accordance with an aspect of the present invention.
Figure 99:
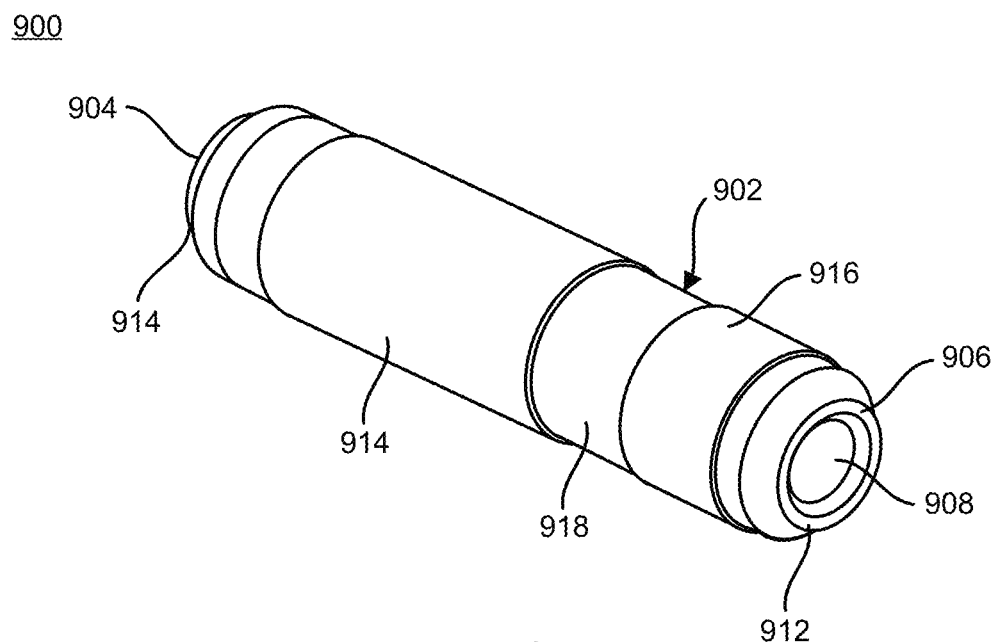
FIG. 99 is a second perspective view of the implant of FIG. 98, in accordance with an aspect of the present invention.
Figure 100:
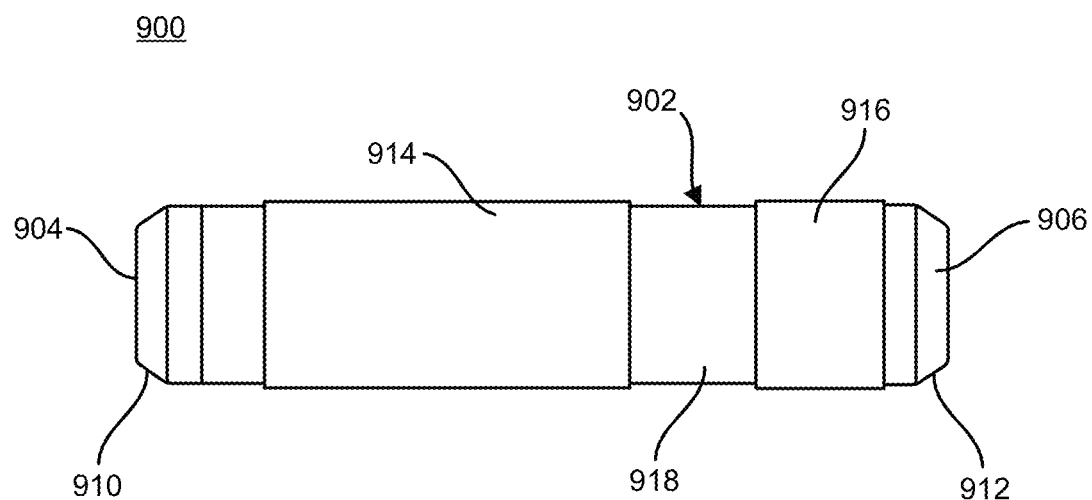
FIG. 100 is a side view of the implant of FIG. 98, in accordance with an aspect of the present invention.
Figure 101:
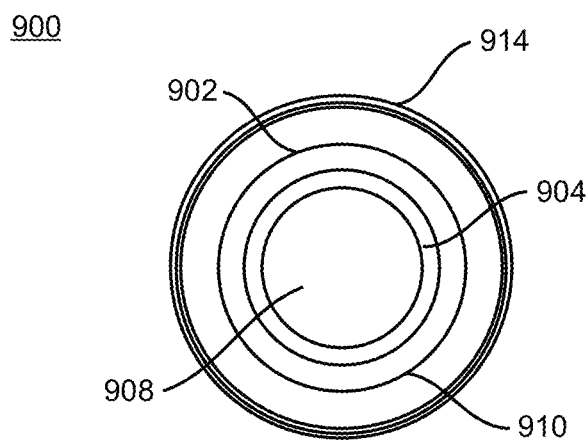
FIG. 101 is an end view of the implant of FIG. 98, in accordance with an aspect of the present invention.

Another implant 900 is shown in FIGS. 98-103. The implant 900 includes a body portion 902 with a first end 904 and a second end 906. The implant 900 also includes an opening 908 extending through the body portion 902 from the first end 904 to the second end 906. The first end 904 may also include a tapered or angled edge 910 and the second end 906 may include a tapered or angled edge 912. The implant 900 may also include a first protrusion 914 extending circumferentially away from the body portion 902 near the first end 904 of the implant 900. The implant 900 may further include a second protrusion 916 extending circumferentially away from the body portion 902 near the second end 906 of the implant 900. The first protrusion 914 may have a first length and the second protrusion 916 may have a second length. The first length may be, for example, longer than the second length. The first and second protrusions 914, 916 may be, for example, smooth or may include a textured surface. The body 902 may include a portion or central member 918 positioned between the first protrusion 914 and the second protrusion 916. As shown in FIGS. 98-100, the portion 918 of the body 902 is aligned with the first and second protrusions 914, 916 to form a straight implant 900.

Figure 102:
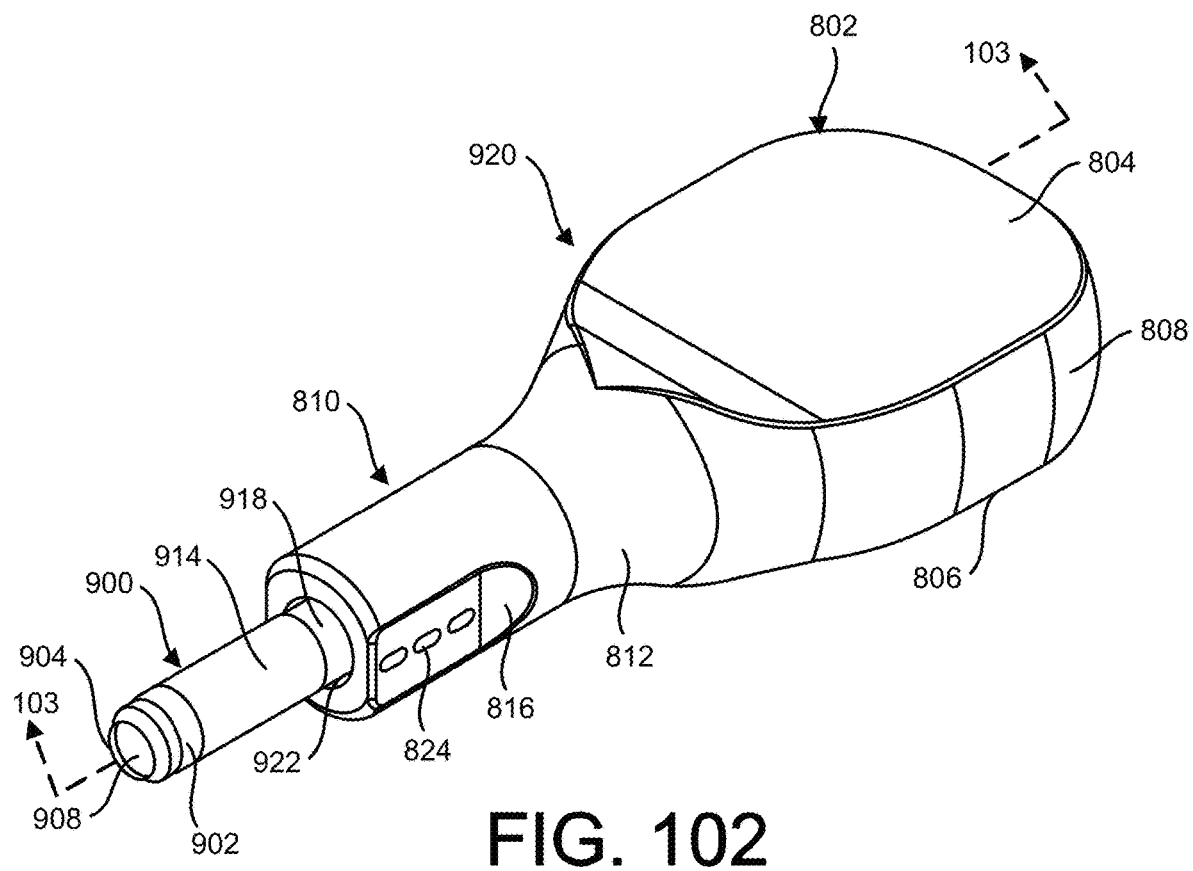
FIG. 102 is a perspective view of the implant of FIG. 98 inserted into another insertion instrument, in accordance with an aspect of the present invention.
Figure 103:
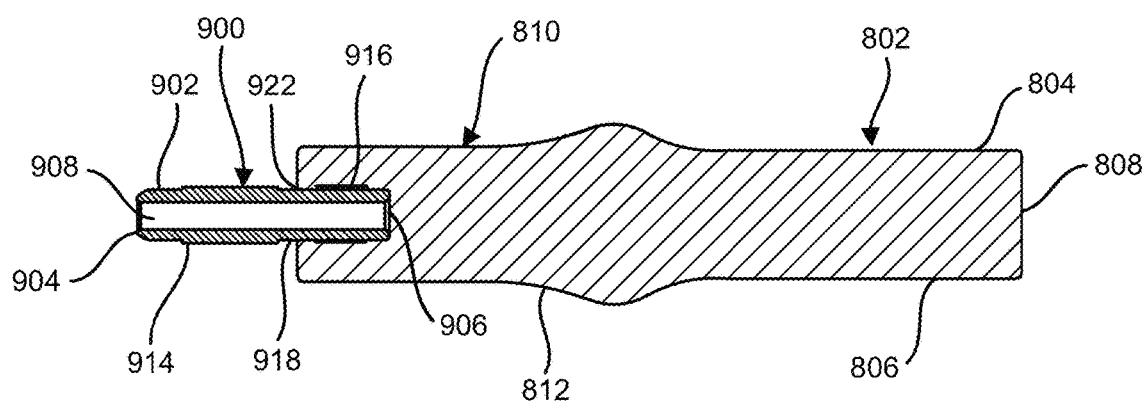
FIG. 103 is a cross-sectional view of the assembled implant and insertion instrument of FIG. 102 taken along line 103-103, in accordance with an aspect of the present invention.
Figure 104:
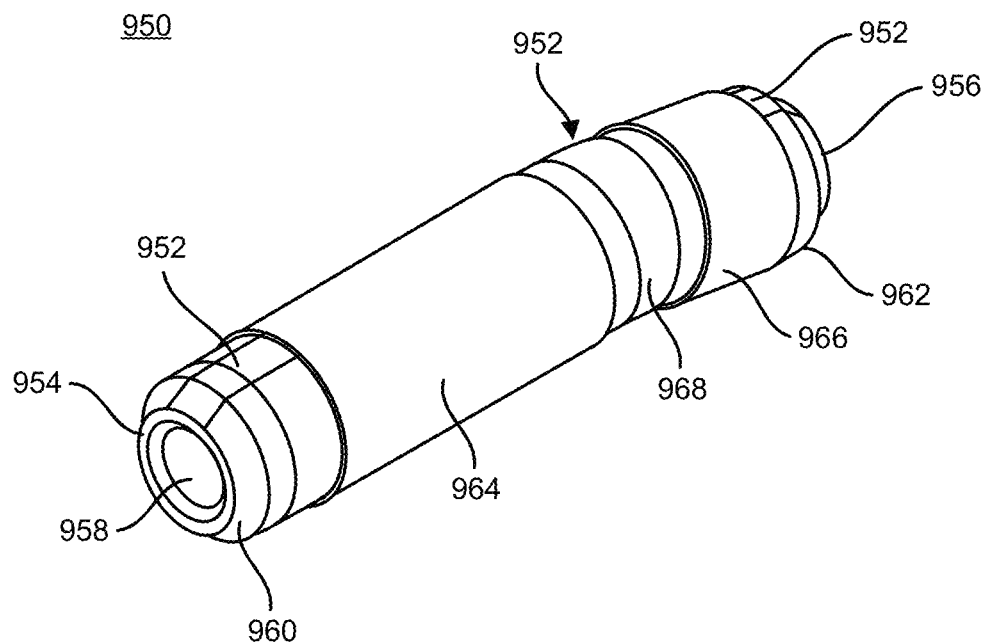
FIG. 104 is a first perspective view of another implant, in accordance with an aspect of the present invention.
Figure 105:
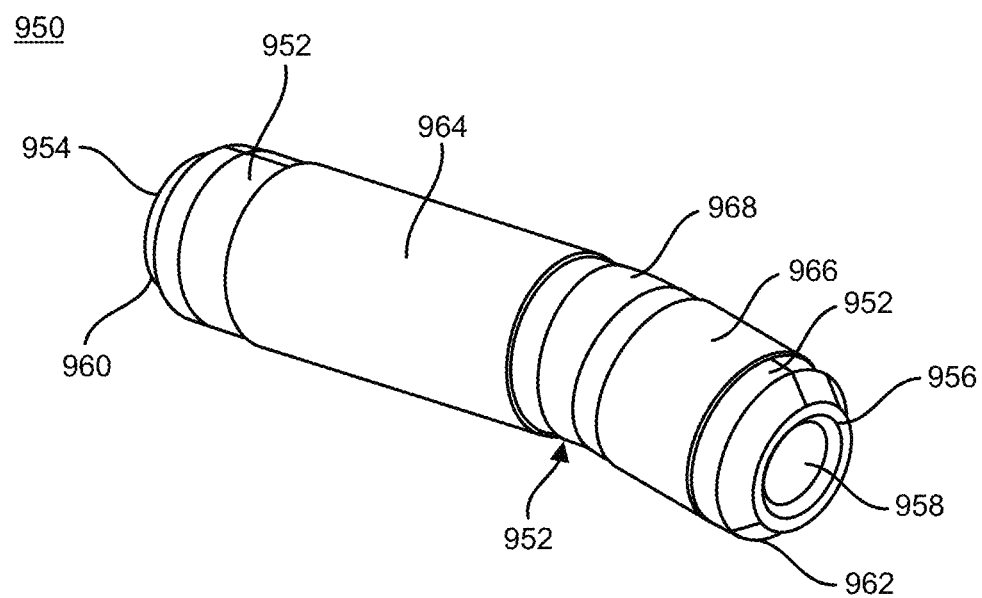
FIG. 105 is a second perspective view of the implant of FIG. 104, in accordance with an aspect of the present invention.
Figure 106:
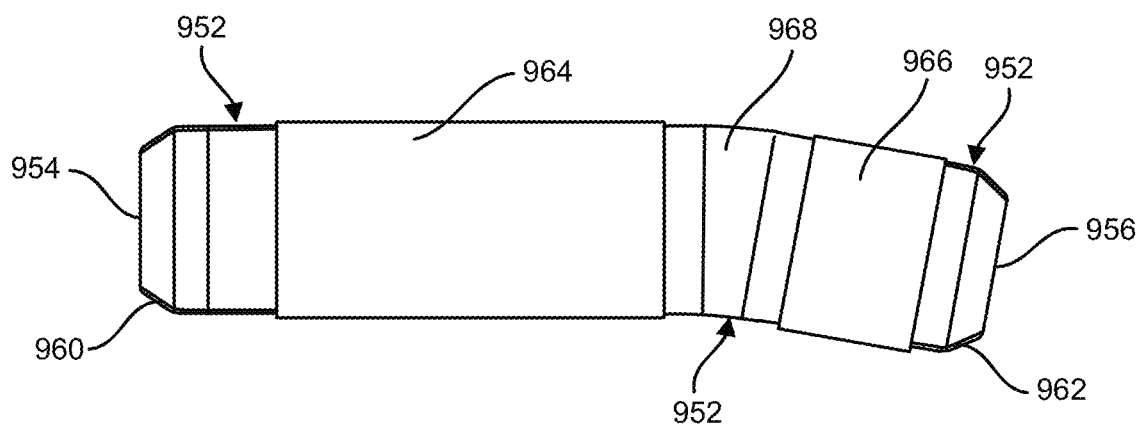
FIG. 106 is a first side view of the implant of FIG. 104, in accordance with an aspect of the present invention.
Figure 107:
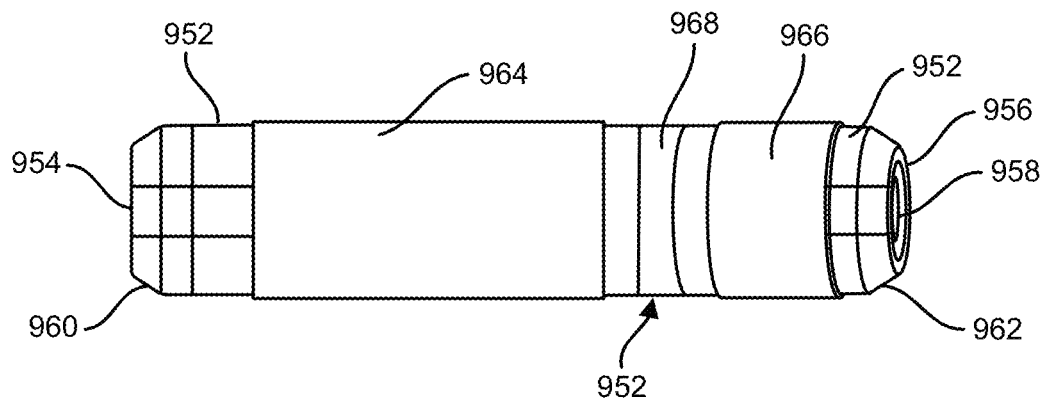
FIG. 107 is a second side view of the implant of FIG. 104, in accordance with an aspect of the present invention.
Figure 108:
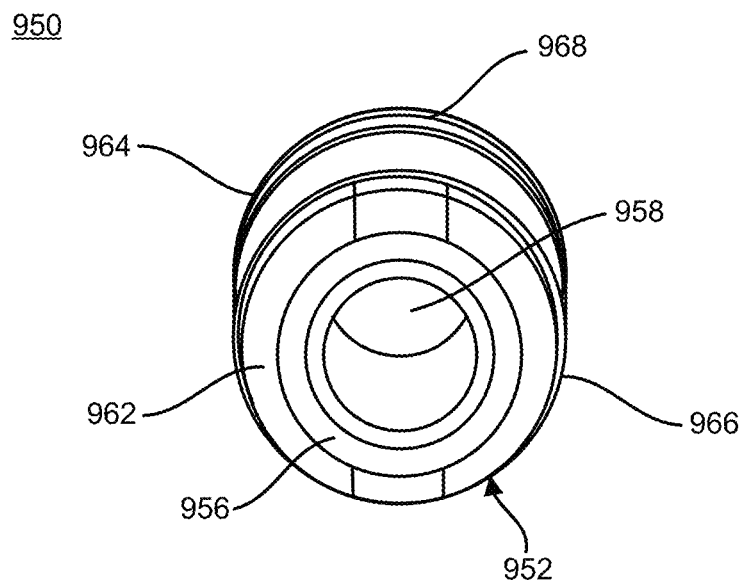
FIG. 108 is a first end view of the implant of FIG. 104, in accordance with an aspect of the present invention.
Figure 109:
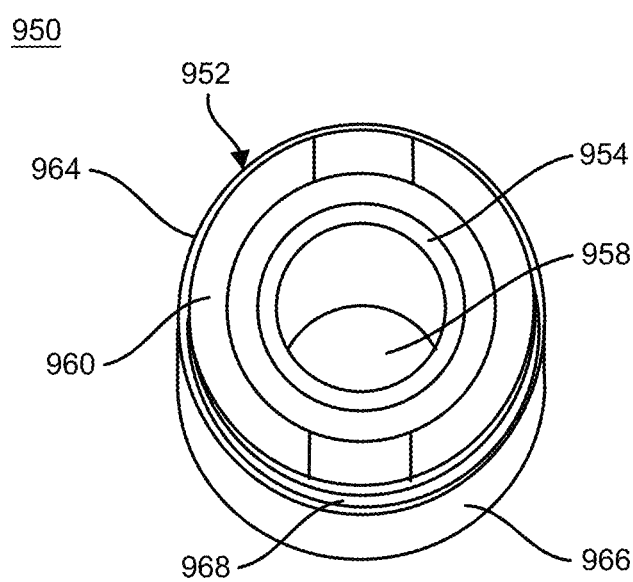
FIG. 109 is a second end view of the implant of FIG. 104, in accordance with an aspect of the present invention.

Referring now to FIGS. 102-103, the implant 900 and corresponding insertion instrument 920 are shown. The insertion instrument 920 may be similar to the insertion instrument 820, as described in greater detail above, which will not be described again here for brevity sake. The insertion instrument 920 includes a body or handle portion 802, a top surface 804, a bottom surface 806, a side portion 808, a coupling member 810, a tapered portion 812, planar sections 816, an opening 922, and alignment markings 824. The alignment markings 824 show the position or angulation of the opening 922. The angulation of the opening 922 may correspond to the position or angulation of the second protrusion 916, as shown in FIG. 103.

Another implant 950 is shown in FIGS. 104-111. The implant 950 includes a body portion 952 with a first end 954 and a second end 956. The implant 950 also includes an opening 958 extending through the body portion 952 from the first end 954 to the second end 956. The first end 954 may also include a tapered or angled edge 960 and the second end 956 may include a tapered or angled edge 962. The implant 950 may also include a first protrusion 964 extending circumferentially away from the body portion 952 near the first end 954 of the implant 950. The implant 950 may further include a second protrusion 966 extending circumferentially away from the body portion 952 near the second end 956 of the implant 950. The first protrusion 964 may have a first length and the second protrusion 966 may have a second length. The first length may be, for example, longer than the second length. The first and second protrusions 964, 966 may be, for example, smooth or may include a textured surface. The body 952 may include a portion or central member 968 positioned between the first protrusion 964 and the second protrusion 966. As shown in FIGS.

104-107, the portion 968 of the body 952 is angled between the first and second protrusions 964, 966 to form an angled implant 950.

Figure 110:
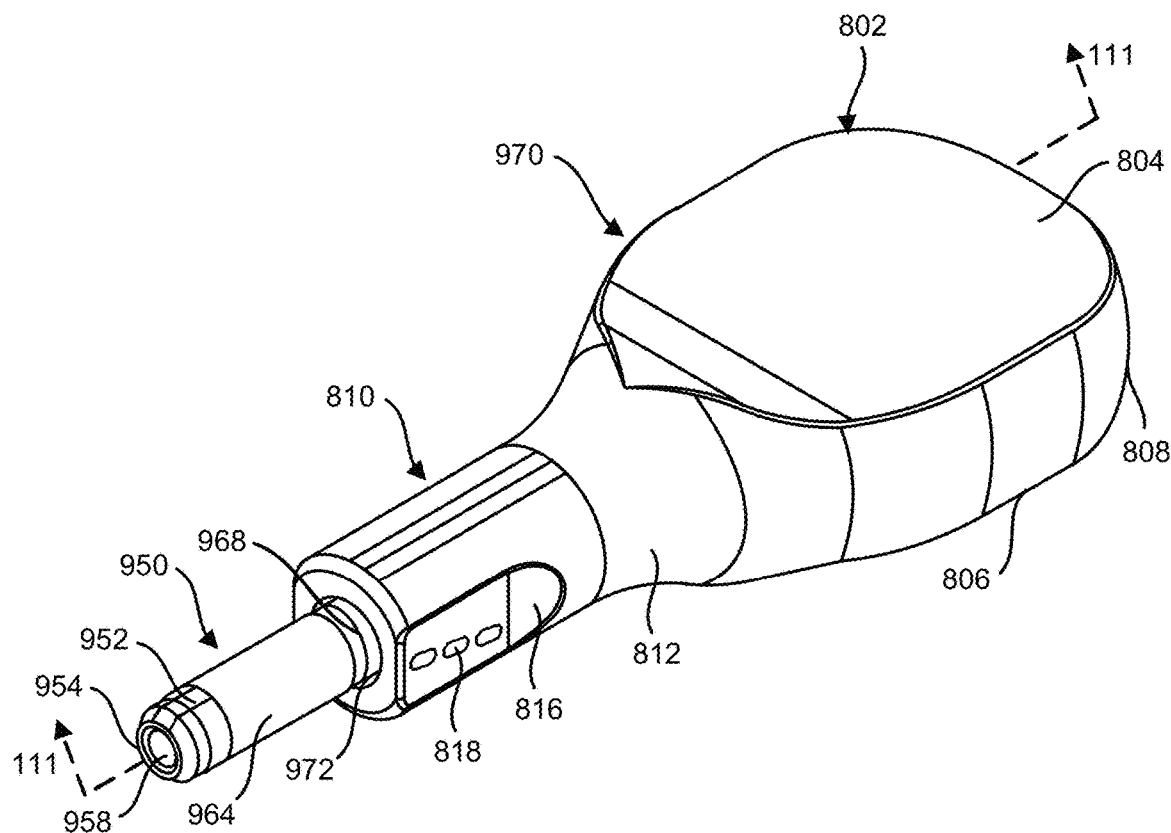
FIG. 110 is a perspective view of the implant of FIG. 104 inserted into another insertion instrument, in accordance with an aspect of the present invention.
Figure 111:
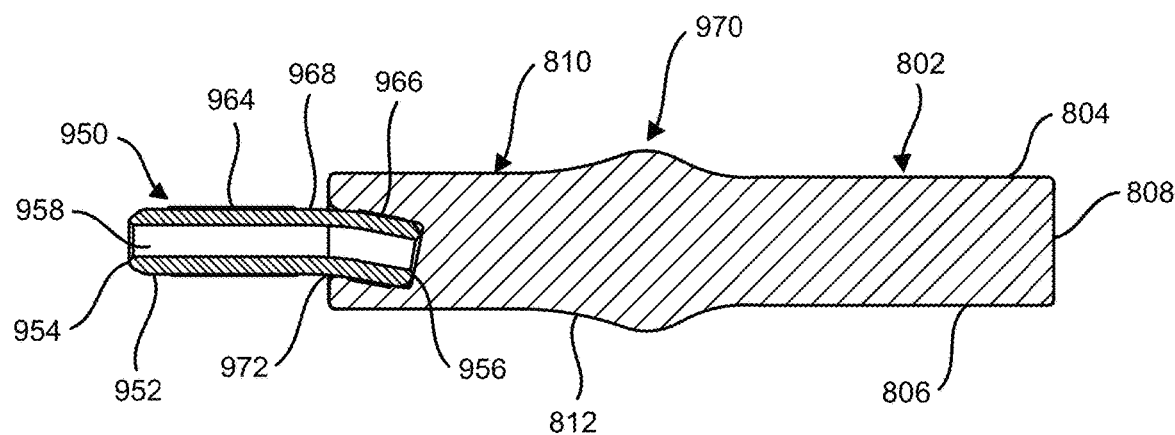
FIG. 111 is a cross-sectional view of the assembled implant and insertion instrument of FIG. 110 taken along line 111-111, in accordance with an aspect of the present invention.
Figure 112:
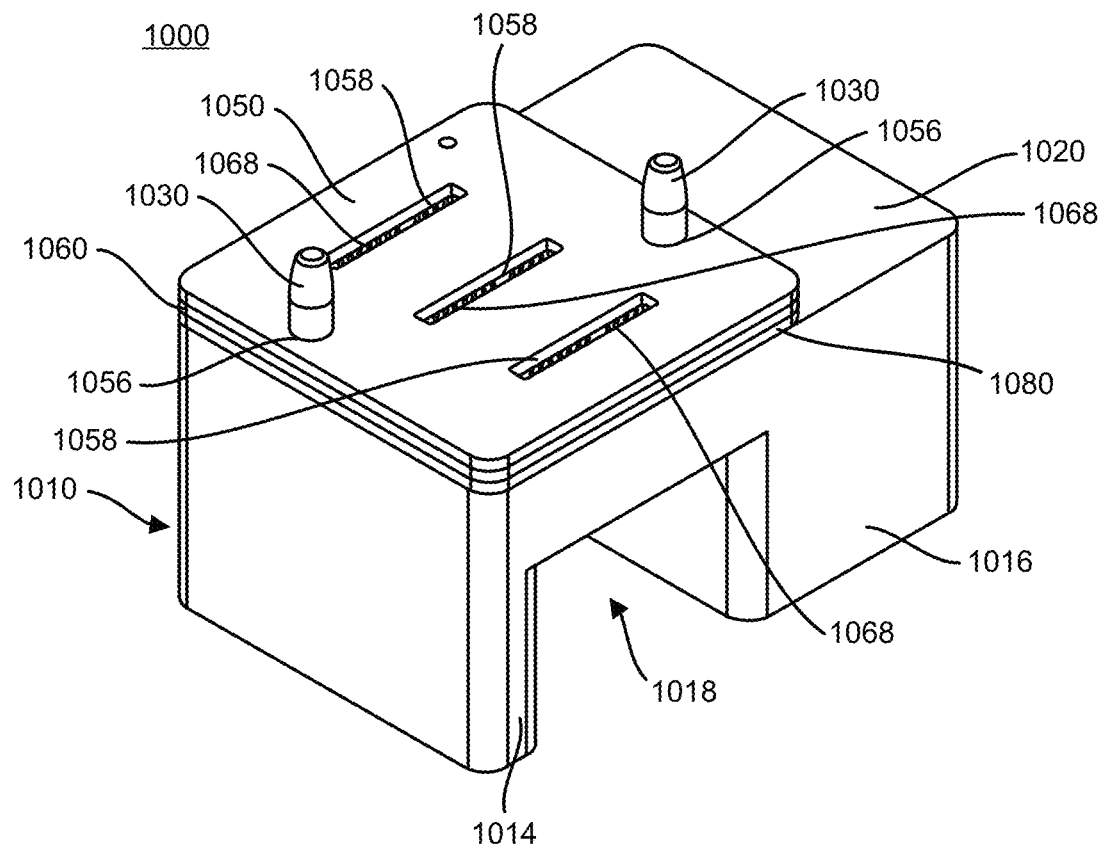
FIG. 112 is a perspective view of a cutting guide, in accordance with an aspect of the present invention.
Figure 113:
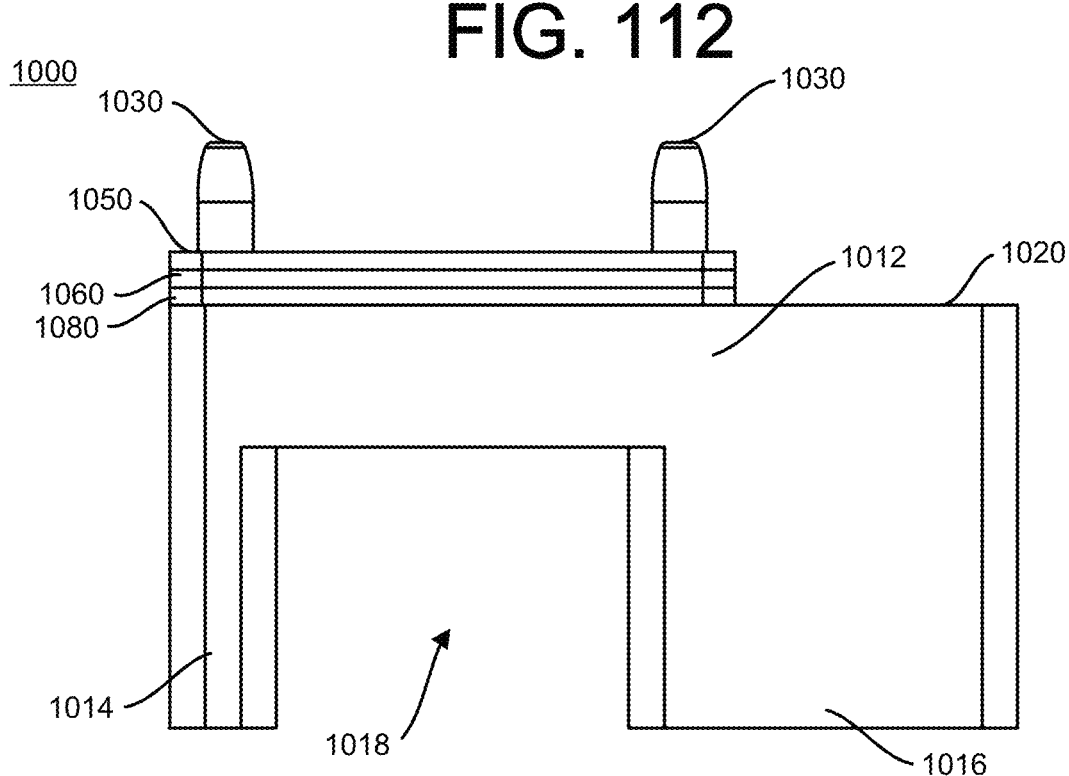
FIG. 113 is a side view of the cutting guide of FIG. 112, in accordance with an aspect of the present invention.
Figure 114:
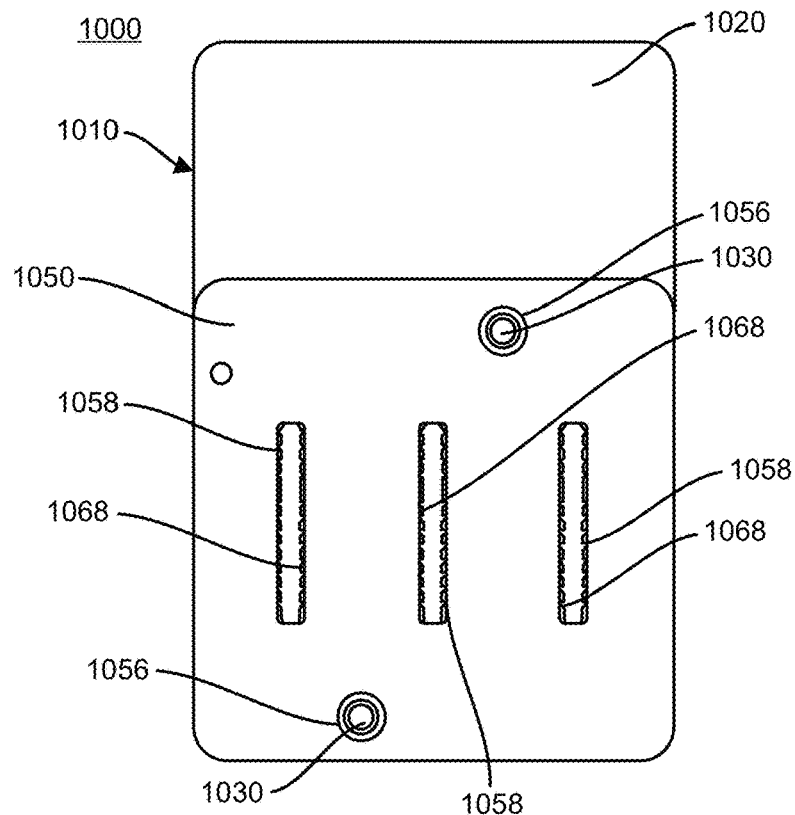
FIG. 114 is a top view of the cutting guide of FIG. 112, in accordance with an aspect of the present invention.
Figure 115:
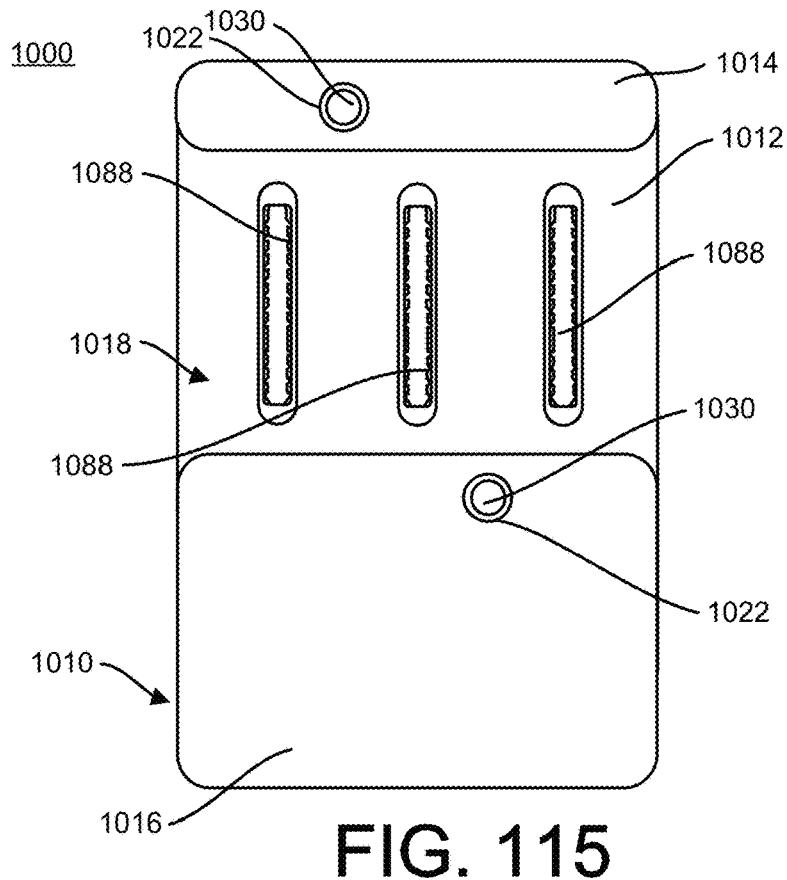
FIG. 115 is a bottom view of the cutting guide of FIG. 112, in accordance with an aspect of the present invention.

Referring now to FIGS. 110-111, the implant 950 and corresponding insertion instrument 970 are shown. The insertion instrument 970 may be similar to the insertion instrument 800, as described in greater detail above, which will not be described again here for brevity sake. The insertion instrument 970 includes a body or handle portion 802, a top surface 804, a bottom surface 806, a side portion 808, a coupling member 810, a tapered portion 812, planar sections 816, alignment markings 818, and an opening 972. The alignment markings 818 show the position or angulation of the opening 972. The angulation of the opening 972 may correspond to the position or angulation of the second protrusion 966, as shown in FIG. 111.

Figure 116:
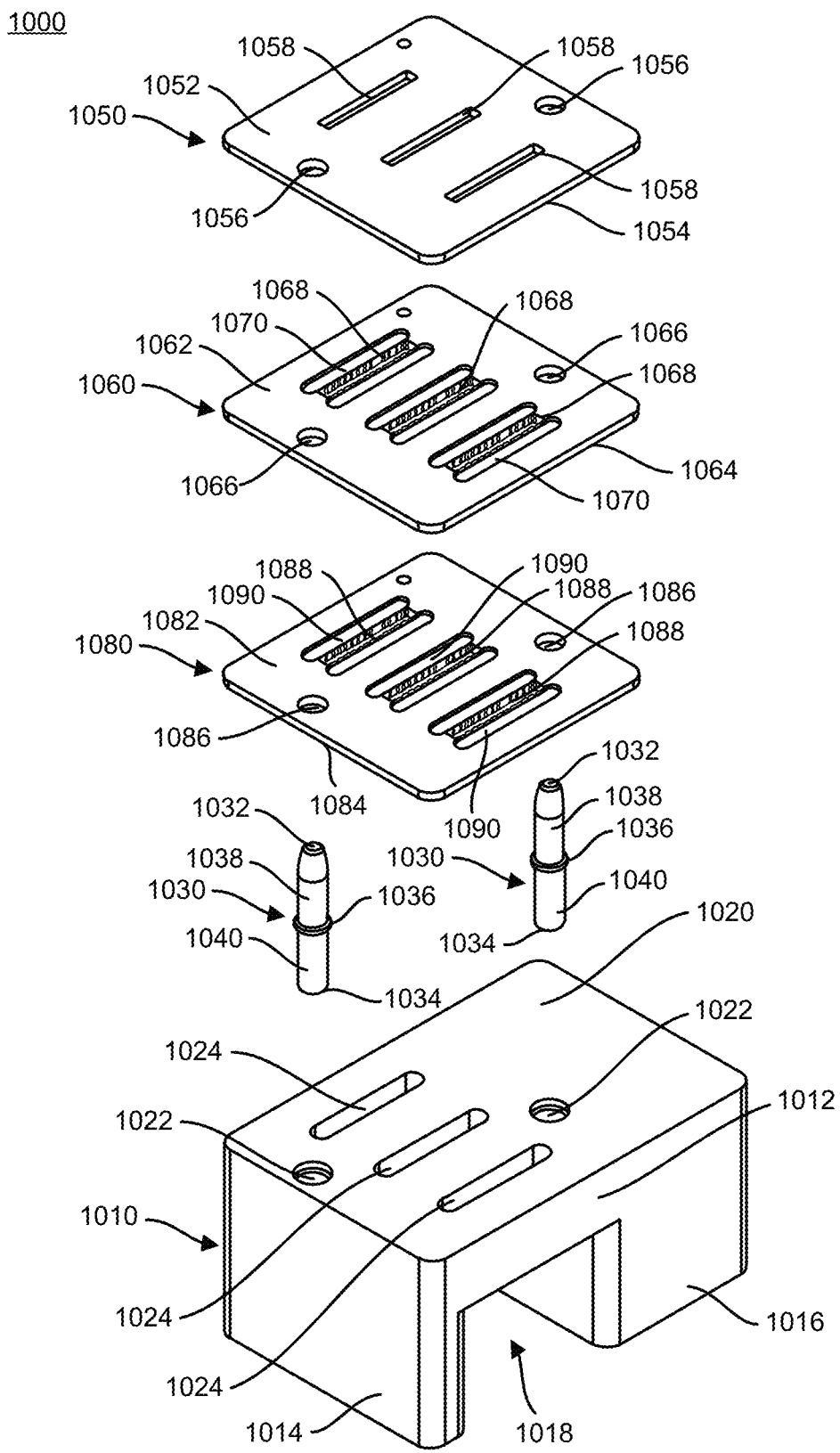
FIG. 116 is an exploded, perspective view of the cutting guide of FIG. 112, in accordance with an aspect of the present invention.
Figure 118:
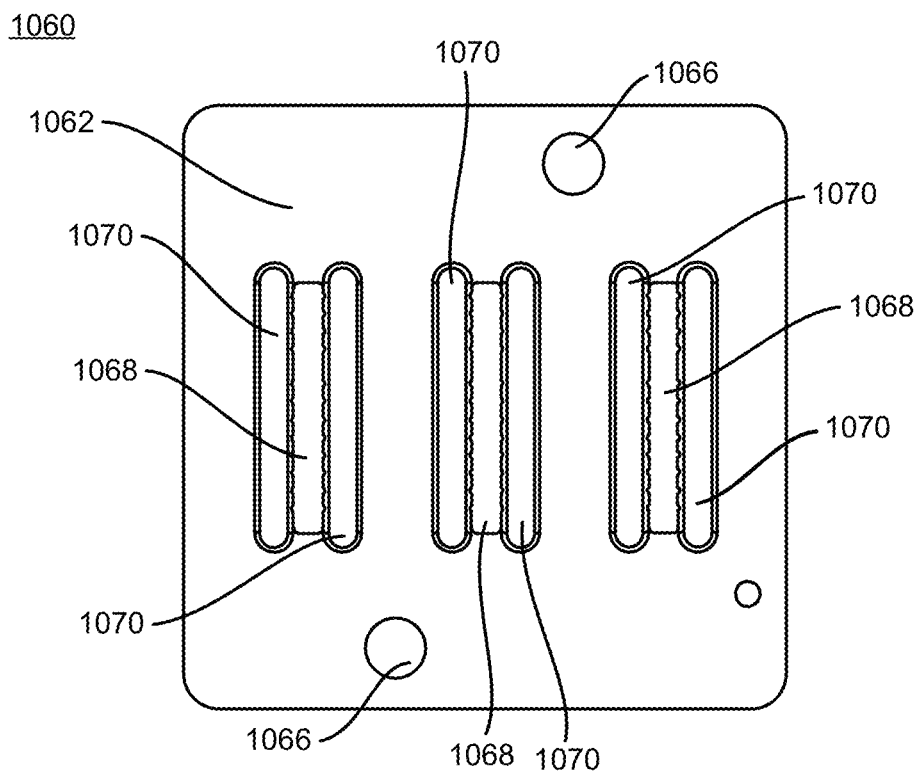
FIG. 118 is a top view of a second plate of the cutting guide of FIG. 112, in accordance with an aspect of the present invention.
Figure 119:
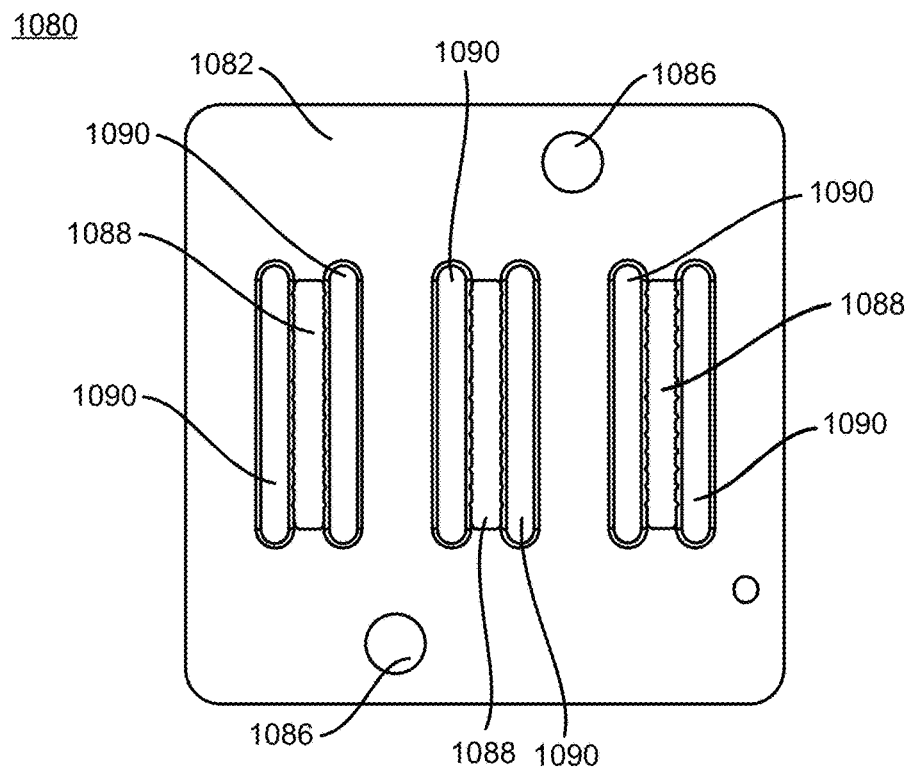
FIG. 119 is a top view of a third plate of the cutting guide of FIG. 112, in accordance with an aspect of the present invention.
Figure 120:
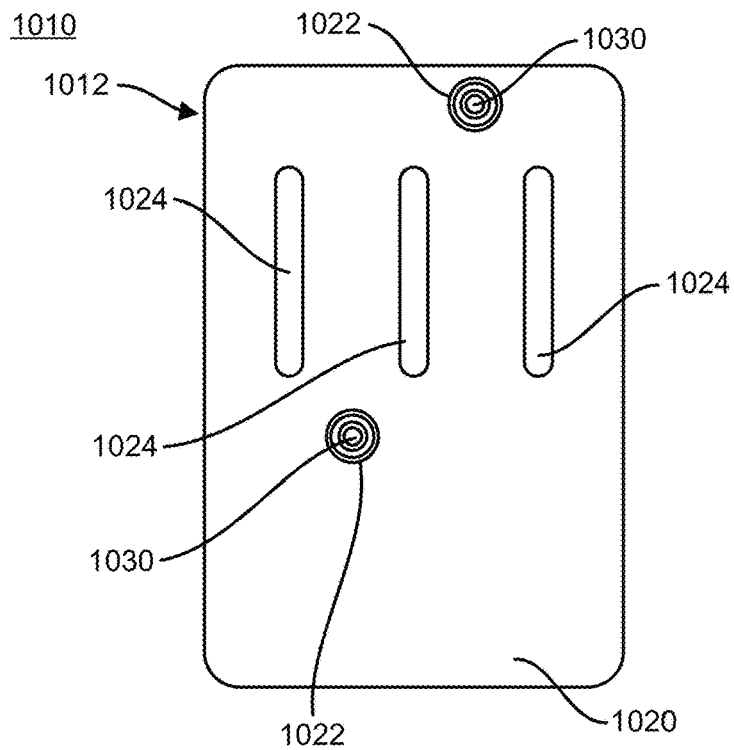
FIG. 120 is a top view of a base member and two pins of the cutting guide of FIG. 112, in accordance with an aspect of the present invention.

Referring now to FIGS. 112-120, a cutting guide 1000 is shown for use in fabricating, for example, implant 850 and at least a portion of implant 680. The cutting guide 1000 includes a base portion 1010, at least one alignment pin 1030, a first plate member 1050, a second plate member 1060, and a third plate member 1080. As shown in FIGS. 116 and 120, the base portion 1010 includes a body 1012 with a first leg 1014 extending away from a bottom surface of the body 1012 at a first end and a second leg 1016 extending away from the bottom surface of the body 1012 at a second end. The second leg 1016 may be, for example, wider than the first leg 1014. The first leg 1014 is separated from the second leg 1016 by a channel 1018. The base portion 1010 may also include at least one opening 1022 extending into the body 1012 from a top surface 1020. The at least one opening 1022 may be sized and shaped or configured to receive the at least one alignment pin 1030. The base portion 1010 also includes at least one implant opening 1024. As shown in the depicted embodiment, the base portion 1010 has, for example, three implant openings 1024. The at least one implant opening 1024 may extend from the top surface 1020 through the body 1012 into the channel 1018.

As shown in FIG. 116, the at least one alignment pin 1030 includes a first end 1032, a second end 1034, and a protrusion 1036 positioned between the first end 1032 and the second end 1034. The alignment pin 1030 also includes a first portion 1038 positioned between the first end 1032 and the protrusion 1036 for receiving the plate members 1050, 1060, 1080. The alignment pin 1030 further includes a second portion 1040 positioned between the second end 1034 and the protrusion 1036. The second portion 1040 may be, for example, sized and shaped or configured to be inserted into the opening 1022.

Figure 117:
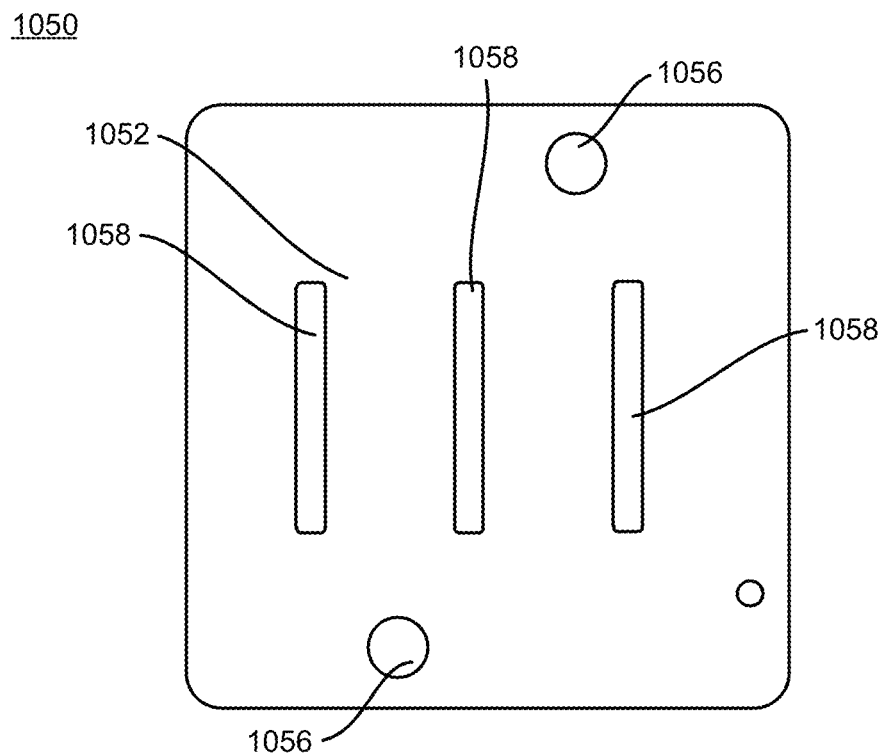
FIG. 117 is a top view of a first plate of the cutting guide of FIG. 112, in accordance with an aspect of the present invention.

With continued reference to FIGS. 116 and 117, the first plate member 1050 may include a top surface 1052 and a bottom surface 1054. The first plate member 1050 may also include at least one alignment hole 1056 for receiving the at least one alignment pin 1030. The at least one alignment hole 1056 may extend from the top surface 1052 through to the bottom surface 1054 of the first plate member 1050. The at least one alignment hole 1056 may be aligned with the at least one opening 1022 of the base portion 1010. The first plate member 1050 may further include at least one implant opening 1058 for receiving the bone graft portions for cutting into the implants 680, 850. The at least one implant opening 1058 may be aligned with the at least one implant opening 1024 of the base portion 1010. The at least one implant opening 1058 may extend from the top surface 1052 through to the bottom surface 1054 of the first plate member 1050.

The second plate member 1060, as shown in FIGS. 116 and 118, may include a top surface 1062 and a bottom surface 1064. The second plate member 1060 may also include at least one alignment hole 1066 for receiving the at least one alignment pin 1030. The at least one alignment hole 1066 may extend from the top surface 1062 through to the bottom surface 1064 of the second plate member 1060. The at least one alignment hole 1066 may be aligned with the at least one opening 1022 of the base portion 1010. The second plate member 1060 may further include at least one implant opening 1068 for receiving the bone graft portions for making an initial cut or pre-cut of the recesses into the implants 680, 850. The at least one implant opening 1068 may include a plurality of teeth along the edge of the at least one implant opening 1068 to cut the bone graft portions as the bone graft portions pass through the at least one implant opening 1068. The plurality of teeth may be spaced to correspond to the grooves in the implants 680, 850. The at least one implant opening 1068 may be aligned with the at least one implant opening 1024 of the base portion 1010 and the at least one implant opening 1058 of the first plate member 1050. The at least one implant opening 1068 may extend from the top surface 1062 through to the bottom surface 1064 of the second plate member 1060. The second plate member 1060 may also include grooves 1070 inset into the top surface 1062 of the second plate member 1060. The grooves 1070 may be positioned adjacent to each implant opening 1068. The third plate member 1080, as shown in FIGS. 116 and 119, may include a top surface 1082 and a bottom surface 1084. The third plate member 1080 may also include at least one alignment hole 1086 for receiving the at least one alignment pin 1030. The at least one alignment hole 1086 may extend from the top surface 1082 through to the bottom surface 1084 of the third plate member 1080. The at least one alignment hole 1086 may be aligned with the at least one opening 1022 of the base portion 1010. The third plate member 1080 may further include at least one implant opening 1088 for receiving the bone graft portions for making a second or final cut of the recesses into the implants 680, 850. The at least one implant opening 1088 may include a plurality of teeth along the edges of the at least one implant opening 1088 to cut the bone graft portions as the bone graft portions pass through the at least one implant opening 1088. The plurality of teeth may be spaced to correspond to the grooves in the implants 680, 850. The at least one implant opening 1088 may be aligned with the at least one implant opening 1024 of the base portion 1010, the at least one implant opening 1058 of the first plate member 1050, and the at least one implant opening 1068 of the second plate member 1060. The at least one implant opening 1088 may extend from the top surface 1082 through to the bottom surface 1084 of the third plate member 1080. The third plate member 1080 may also include grooves 1090 inset into the top surface 1082 of the third plate member 1080. The grooves 1090 may be positioned adjacent to each implant opening 1088.

The cutting guide 1000 may be assembled by inserting the alignment pins 1030 into the openings 1022 in the base portion 1010. The alignment holes 1086 of the third plate member 1080 may then be aligned with the alignment pins 1030 and the third plate member 1080 may be placed onto the base portion 1010. Next, the alignment holes 1066 of the second plate member 1060 may be aligned with the alignment pins 1030 and the second plate member 1060 may be placed onto the third plate member 1080. Finally, the alignment holes 1056 of the first plate member 1050 may be aligned with the alignment pins 1030 and the first plate member 1050 may be placed onto the second plate member 1060.

The cutting guide 1000 may be used once assembled to create an implant, for example, implant 680, 850. Initially, at least one bone graft portion is obtained and cut to match the size of the implant opening 1058. Next, the bone graft portion may be placed into the implant opening 1058 and a press may be used to push the bone graft portion through the first plate member 1050. The bone graft portion may then be pushed through the second plate member 1060 to make initial recess cuts into two sides of the implants 680, 850. Then, the bone graft portion may be pushed through the third plate member 1080 to make final recess cuts into the two sides of the implants 680, 850. Finally, the bone graft portion is pushed to pass through the implant opening 1024 of the base portion 1010. For the implant 900, the bone graft portions may then be rotated and pushed through the cutting guide 1000 again to cut the recesses into the other two sides of the implant 900. Although the implant openings 1024, 1058, 1068, 1088 shown in FIGS. 112-120 are straight openings, it is also contemplated that the implant openings 1024, 1058, 1068, 1088 may be angled to match the angled implant 680, to allow for the cutting guide 1000 to be used to cut the recesses into the angled sides of the implant 680.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. An implant insertion and removal system, comprising:
   at least one trocar tip guide wire, comprising:
      a coupling member including at least one engagement member extending from the coupling member;
   at least one trephine including an opening for receiving the at least one trocar tip guide wire and a trephine coupling member for removably coupling to the coupling member of the at least one trocar tip guide wire;
   at least one reamer including an opening for receiving the at least one trocar tip guide wire and a reamer coupling member for removably coupling to the coupling member of the at least one trocar tip guide wire; and
   at least one drill bit including an opening for receiving the at least one trocar tip guide wire and drill bit coupling member for removably coupling to the coupling member of the at least one trocar tip guide wire.

2. The implant insertion and removal system of claim 1, further comprising:
   a connector end including an opening, wherein the at least one trocar tip guide wire is received within the opening of the connector end.

3. The implant insertion and removal system of claim 1, wherein the trephine:
   coupling member comprises:
      at least one protrusion extending from the trephine coupling member, and wherein the at least one protrusion of the at least one trephine engages the at least one engagement member of the at least one trocar tip guide wire.

4. The implant insertion and removal system of claim 1, wherein the reamer:
   coupling member comprises:
      at least one lip extending from the reamer coupling member, and wherein the at least one lip of the at least one reamer engages the at least one engagement member of the at least one trocar tip guide wire.

5. The implant insertion and removal system of claim 1, wherein the drill bit:
   coupling member comprises:
      at least one snap member extending from the drill bit coupling member, and wherein the at least one snap member of the at least one drill bit engages the at least one engagement member of the at least one trocar tip guide wire.

6. The implant insertion and removal system of claim 1, further comprising:
   an implant, wherein the implant comprises:
      a first body portion; and
      a second body portion;
      wherein the first body portion extends from a first end toward the second body portion, the second body portion extends from a second end toward the first body portion, and the first body portion engages the second body portion at a coupling portion.

7. The implant insertion and removal system of claim 6, wherein the implant further comprises:
   a plurality of first grooves recessed into a dorsal surface and a plantar surface; and
   a plurality of second grooves recessed into a medial surface and a lateral surface.

8. The implant insertion and removal system of claim 7, wherein the implant further comprises:
   a plurality of first ribs positioned between adjacent first grooves of the plurality of first grooves; and
   a plurality of second ribs positioned between adjacent second grooves of the plurality of second grooves.

9. The implant insertion and removal system of claim 6, wherein the first body portion is at least one of aligned along a longitudinal axis with the second body portion and angled relative to the second body portion, wherein the first body portion has a polygonal shape, and wherein the second body portion has a polygonal shape.

10. The implant insertion and removal system of claim 9, wherein the polygonal shape of the first body portion is a quadrilateral shape and wherein the polygonal shape of the second body portion is a quadrilateral shape.

11. The implant insertion and removal system of claim 1, further comprising:
   an implant, wherein the implant comprises:
      a body portion with a first end and a second end;
      a first protrusion extending circumferentially away from the body portion, the first protrusion extending between the first end and a central member of the body portion; and
      a second protrusion extending circumferentially away from the body portion, the second protrusion extending between the central member and the second end of the body portion.

12. The implant insertion and removal system of claim 11, wherein the implant further comprises:
   an opening extending through the body from the first end to the second end.

13. The implant insertion and removal system of claim 1, further comprising:
   an insertion instrument with an opening for receiving a portion of an implant.

14. The implant insertion and removal system of claim 13, wherein the insertion instrument comprises:
   a handle portion; and
   a coupling member coupled to and extending away from an end of the handle portion.

15. The implant insertion and removal system of claim 14, wherein the opening extends from an end of the insertion instrument into the coupling member.

16. The implant insertion and removal system of claim 15, wherein the coupling member of the insertion instrument further comprises:
   alignment markings positioned on at least one side of the coupling member, wherein the alignment markings correspond to a longitudinal axis of the opening.

17. The implant insertion and removal system of claim 16, wherein the coupling member of the insertion instrument further comprises:
   at least one planar section positioned on the at least one side of the coupling member, wherein the alignment markings are positioned on the at least one planar section.

18. The implant insertion and removal system of claim 13, wherein the opening is at least one of aligned with a longitudinal axis of the insertion instrument and angled relative to the longitudinal axis of the insertion instrument.

19. A surgical method, comprising:
   exposing a patient's joint;
   inserting a first k-wire into a base of the middle phalanx proximally;
   retrograding the first k-wire from a tip of a toe, across a distal phalanx and a middle phalanx;
   inserting the first k-wire into a proximal phalanx;
   pulling the first k-wire to position a tip of the first k-wire in the joint;
   inserting a second k-wire into the proximal phalanx;
   driving a drill across the second k-wire and into the proximal phalanx;
   removing the second k-wire from the patient's joint;
   driving the drill and the first k-wire into the middle phalanx;
   inserting an implant into the proximal phalanx and the middle phalanx, wherein the implant comprises:
      a dorsal surface, a plantar surface, a medial surface and a lateral surface;
      a first body portion with a plurality of grooves inset into each of the dorsal surface, the plantar surface, the medial surface, and the lateral surface; and
      a second body portion with a plurality of grooves inset into each of the dorsal surface, the plantar surface, the medial surface, and the lateral surface,
      wherein the second body portion is angled relative to the first body portion, wherein the first body portion has a polygonal shape, and wherein the second body portion has a polygonal shape; and
   completing the procedure.

20. A surgical method, comprising:
   exposing a patient's joint;
   coupling a guide wire to a reamer by securing at least one engagement member extending away from a coupling member of the guide wire to at least one lip extending away from a reamer coupling member of the reamer;
   inserting the coupled guide wire and reamer into a middle phalanx;
   removing the coupled guide wire and reamer after cartilage resection is complete;
   coupling the guide wire to a drill by securing the at least one engagement member of the coupling member of the guide wire to at least one snap member extending away from a drill coupling member of the drill;
   inserting the coupled guide wire and drill into a proximal phalanx;
   removing the coupled guide wire and drill from the proximal phalanx;
   inserting the coupled guide wire and drill into the middle phalanx;
   removing the coupled guide wire and drill from the middle phalanx;
   inserting an implant into the proximal phalanx and the middle phalanx; and
   completing the procedure.

* * * * *

UNITED STATES PATENT AND TRADEMARK OFFICE
CERTIFICATE OF CORRECTION

PATENT NO. : 10,660,676 B2
APPLICATION NO. : 15/900528
DATED : May 26, 2020
INVENTOR(S) : Lintula et al.

Page 1 of 1

It is certified that error appears in the above-identified patent and that said Letters Patent is hereby corrected as shown below:

In the Claims

Column 22, Line 16: Claim 3, Delete "wherein the trephine:" and insert -- wherein the trephine --

Column 22, Line 24: Claim 4, Delete "wherein the reamer:" and insert -- wherein the reamer --

Column 22, Line 31: Claim 5, Delete "wherein the drill bit:" and insert -- wherein the drill bit --

Signed and Sealed this
Seventh Day of July, 2020

Andrei Iancu
*Director of the United States Patent and Trademark Office*